(12) United States Patent
Lippard et al.

(10) Patent No.: US 8,883,962 B2
(45) Date of Patent: Nov. 11, 2014

(54) ZINC-RESPONSIVE PEPTIDES, AND METHODS OF USE THEREOF

(71) Applicant: Massachusetts Institute of Technology, Cambridge, MA (US)

(72) Inventors: Stephen J. Lippard, Cambridge, MA (US); Robert J. Radford, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/740,604

(22) Filed: Jan. 14, 2013

(65) Prior Publication Data

US 2013/0224760 A1    Aug. 29, 2013

Related U.S. Application Data

(60) Provisional application No. 61/586,424, filed on Jan. 13, 2012.

(51) Int. Cl.
| | |
|---|---|
| *A61K 38/28* | (2006.01) |
| *C07K 5/00* | (2006.01) |
| *C07K 7/00* | (2006.01) |
| *C07K 16/00* | (2006.01) |
| *C07K 17/00* | (2006.01) |
| *G01N 33/84* | (2006.01) |
| *A61K 49/00* | (2006.01) |
| *C07K 14/00* | (2006.01) |
| *C07K 7/06* | (2006.01) |
| *C07D 311/82* | (2006.01) |
| *G01N 33/50* | (2006.01) |
| *C07K 5/10* | (2006.01) |
| *C07D 405/14* | (2006.01) |
| *C07D 215/40* | (2006.01) |
| *C07D 409/14* | (2006.01) |

(52) U.S. Cl.
CPC ............ *G01N 33/5005* (2013.01); *G01N 33/84* (2013.01); *A61K 49/0043* (2013.01); *C07K 14/00* (2013.01); *C07K 7/06* (2013.01); *C07D 311/82* (2013.01); *A61K 49/0052* (2013.01); *C07K 5/10* (2013.01); *C07D 405/14* (2013.01); *C07D 215/40* (2013.01); *A61K 49/0041* (2013.01); *C07D 409/14* (2013.01)
USPC ........................................................ 530/304

(58) Field of Classification Search
CPC ........... A61K 49/0004; A61K 49/0019; A61K 49/0021
See application file for complete search history.

(56) References Cited

U.S. PATENT DOCUMENTS 6,013,802 A    1/2000    Hoyland et al.

US008883962B2

| 2004/0224420 | A1* | 11/2004 | Lippard et al. .................. 436/74 |
|---|---|---|---|
| 2008/0182971 | A1* | 7/2008 | McAuliffe et al. ............ 530/345 |
| 2011/0086341 | A1 | 4/2011 | Batchelor et al. |
| 2012/0271100 | A1 | 10/2012 | Woodruff et al. |

FOREIGN PATENT DOCUMENTS

| WO | WO-03/091689 | 11/2003 |
|---|---|---|
| WO | WO-2011/019864 | 2/2011 |

OTHER PUBLICATIONS

Kruger et al., Chem. Commun., 2002, 2092-2093.*
International Search Report dated Jun. 19, 2013, from PCT/US13/21424.
Blaquiere et al., "Decarboxylative Ketone aldol reactions: development and mechanistic evaluation under metal-free conditions," J Org Chem, 74(16):6190-6198 (2009).
Bozym et al., "Measuring picomolar intracellular exchangeable zinc in PC-12 cells using a ratiometric fluorescence biosensor," ACS Chem Biol., 1(2):103-111 (2006).
Burdette et al., "Fluorescent sensors for Zn(2+) based on a fluorescein platform: synthesis, properties and intracellular distribution," J Am Chem Soc, 123(32):7831-7841 (2001).
Dean et al., "Visualizing metal ions in cells: an overview of analytical techniques, approaches, and probes," Biochim Biophys Acta, 1823(9):1406-1415 (2012).
Dittmer et al., "Genetically Encoded Sensors to Elucidate Spatial Distribution of Cellular Zinc," J. Am. Chem. Soc. 284(16289-16297 (2009).
Domaille et al., "Synthetic fluorescent sensors for studying the cell biology of metals," Nat Chem Biol., 4(3):168-175 (2008).
Fahrni et al., "Aqueous Coordination Chemistry of Quinoline-Based Fluorescence Probes for the Biological Chemistry of Zinc," J. Am. Chem. Soc., 121(49):11448-11458 (1999).
Frederickson, C., "Imaging zinc: old and new tools," Sci STKE, 2003(182):pe18 (2003).
Godwin et al., "A Fluorescent Zinc Probe Based on Metal-Induced Peptide Folding," J. Am. Chem. Soc., 118(27):6514-6515 (1996).
Hendrickson et al., "Coordination and Fluorescence of the Intracellular $Zn^{2+}$ Probe [2-methyl-8- (4-Toluenesulfonamido)-6-quinolyloxy]acetic Acid (Zinquin A) in Ternary $Zn^{2+}$ Complexes," J. Am. Chem. Soc., 125(13):3889-3895 (2003).
Horton et al., "Mitochondria-penetrating peptides," Chem Biol., 15(4):375-382 (2008).
Iyoshi et al., "Development of a cholesterol-conjugated fluorescent sensor for site-specific detection of zinc ion at the plasma membrane," Org. Lett., 13(17):4558-4561 (2011).

(Continued)

*Primary Examiner* — Marcela M Cordero Garcia
*Assistant Examiner* — Kaipeen Yang
(74) *Attorney, Agent, or Firm* — Foley Hoag LLP

(57) ABSTRACT

Described herein are compounds and methods useful in the detection of, e.g., $Zn^{2+}$, in vitro and in vivo. The compounds include amino acids and peptides functionalized with a moiety that binds, e.g., $Zn^{2+}$. The peptides may be further functionalized with a detectable moiety. The peptides may also comprise amino acid sequences known to localize extracellularly or in specific areas within a cell.

28 Claims, 22 Drawing Sheets

(56) References Cited

OTHER PUBLICATIONS

Kay, AR, "Imaging synaptic zinc: promises and perils," Trends Neurosci, 29(4):200-206 (2006).
Kay et al., "Influence of Location of a Fluorescent Zinc Probe in Brain Slices on Its Response to Synaptic Activation," J Neurophysiol, 95:1949-1956 (2006).
Kratz et al., "Prodrug strategies in anticancer chemotherapy," ChemMedChem, 3(1):20-53 (2008).
Kvach et al., "Practical synthesis of isomerically pure 5- and 6-carboxytetramethylrhodamines, useful dyes for DNA probes," Bioconjugate Chemistry, 20(8):1673-1682 (2009).
Li et al., "Imaging dynamic insulin release using a fluorescent zinc indicator for monitoring induced exocytotic release (ZIMIR)," PNAS, 108(52):21063-21068 (2011).
Martin et al., "Peptide-guided Gene Delivery," The AAPS Journal, 9(1):E18 (2007).
Nolan et al., "QZ1 and QZ2: Rapid, Reversible Quinoline-Derivaatized Fluoresceins for Sensing Biological Zn(II)," J Am Chem Soc., 127(48):16812-16823 (2005).
Nolan et al., "Small-Molecule Fluorescent Sensors for Investigating Zinc Metalloneurochemistry," Acc Chem Res, 42(1):193-203 (2009).
Nowakowski et al., "Sensor Specific Imaging of Proteomic $Zn^{2+}$ with Zinquin and TSQ after Cellular Exposure to N-ethylmaleimide," Metallomics, 4(5):448-456 (2012).
Pan et al., "Vesicular zinc promotes presynaptic and inhibits postsynaptic long term potentiation of mossy fiber-CA3 synapse," Neuron, 71(6):1116-1126 (2011).
Pap et al., "Peptide-based targeting of fluorophores to organelles in living cells," Exp Cell Res., 265(2):288-293 (2001).
Pazos et al., "Peptide-based fluorescent biosensors," Chem Soc Rev., 38(12):3348-3359 (2009).
Pluth et al., "Biochemistry of Mobile Zinc and Nitric Oxide Revealed by Fluorescent Sensors," Annu Rev Biochem., 80:333-355 (2011).
Qin et al., "Measuring steady-state and dynamic endoplasmic reticulum and Golgi $Zn^{2+}$ with genetically encoded sensors," PNAS, 108(18):7351-7356 (2011).
Que et al., "Metals in nurobiology: probing their chemistry and biology with molecular imaging," Chem Rev., 108(5):1517-1549 (2008).
Sahoo et al., "A 10-Å Spectroscopic Ruler Applied to Short Polyprolines," J. Am. Chem. Soc., 129(31):9762-9772 (2007).
Shults et al., "Modular and Tunable Chemosensor Scaffold for Divalent Zinc," J. Am. Chem. Soc., 125(35):10591-10597 (2003).
Smotrys et al., "Palmitoylation of intracellular signaling proteins: regulation and function," Annu Rev Biochem., 73:559-587 (2004).
Stewart et al., "Cell-penetrating peptides as delivery vehicles for biology and medicine," Org Biomol Chem., 6(13):2242-2255 (2008).
Stryer et al., "Energy Transfer: A Spectroscopic Ruler," PNAS, 58:719-726 (1967).
Togashi et al., "Investigating tryptophan quenching of fluorescein fluorescence under protolytic equilibrium," J Phys Chem A., 113(2):2757-2767 (2009).
Tomat et al., "Imaging Mobile Zinc in Biology," Curr Opin Chem Biol., 14(2):225-230 (2010).
Tomat et al., "Organelle-Specific Zinc Detection Using Zinpyr-Labeled Fusion Proteins in Live Cells," J. Am. Chem. Soc., 130(47):15776-15777 (2008).
Varkouhi et al., "Endosomal escape pathways for delivery of biologicals," J Control Release, 151(3):220-228 (2011).
Vinkenborg et al., "Genetically encoded FRET sensors to monitor intracellular Zn2+ homeostasis," Nat Methods, 6(10):737-740 (2009).
Walkup et al., "A New Cell-Permeable Fluorescent Probe for $Zn^{2+}$," J. Am. Chem. Soc., 122(23):5644-5645 (2000).
Walkup et al., "Design and Evaluation of a Peptidyl Fluorescent Chemosensor for Divalent Zinc," J. Am. Chem. Soc., 118(12):3053-3054 (1996).
Walkup et al., "Fluorescent Chemosensors for Divalent Zinc Based on Zinc Finger Domains, Enhanced Oxidative Stability, Metal Binding Affinity, and Structural and Functional Characterization," J. Am. Chem. Soc., 119(15):3443-3450 (1997).
Weber et al., "A fast and inexpensive method for N-terminal fluorescein-labeling of peptides," Bioorg Med Chem Lett., 8(6):597-600 (1998).
Woodroofe et al., "Membrane-permeable and -impermeable sensors of the Zinpyr family and their application to imaging of hippocampal zinc in vivo," Chem Biol., 11(12):1659-1666 (2004).
Yousif et al., "Mitochondria-penetrating peptides: sequence effects and model cargo transport," Chembiochem, 10(12):2081-2088 (2009).

* cited by examiner

Figure 8

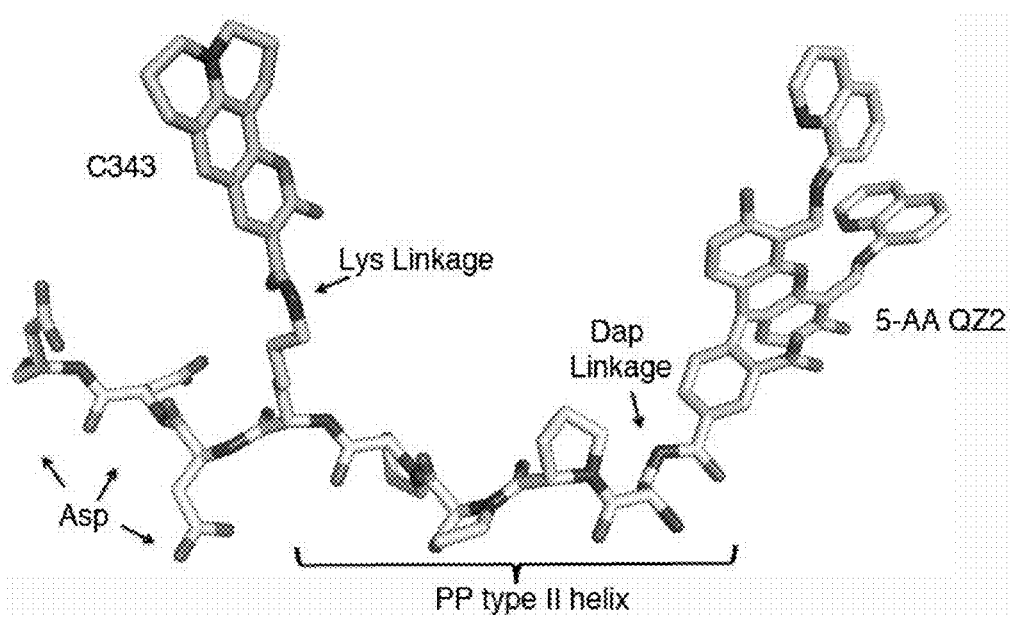

Figure 9

| Amino Acid Sequence* | Location of ZRP | Biological Destination |
|---|---|---|
| KALAKALAKALA | N-terminus | Cell internalization |
| RQIKIWFQNRRMKWKK | N-terminus | Cell internalization |
| GRKKRRQRRRPQ | C-terminus | Cell internalization |
| DDD | N or C-terminus | Extracellular localization |
| SDYQRL | N-terminus | TGN localization |
| KDEL | N-terminus | ER localization |
| KQEGAAVLLPVLLAAPG | N-terminus | Mitochondrial Matrix localization |

Figure 29

| Sensor | $\lambda_{abs}$ (nm), $\varepsilon \times 10^4$ (M$^{-1}$cm$^{-1}$) | | $\phi_{apo}$ | $\phi_{Zn}$ | $K_{d\text{-}Zn}$ (M)$^c$ | Normalized $K_{d\text{-}Zn}$ |
|---|---|---|---|---|---|---|
| | Apo | Zn(II) | | | | |
| Palm-P$_3$D$_2$K(ZP1)$^a$ | 519, 6.6 | 508, 7.4 | 0.16±0.053 | 0.79±0.049 | 8.2(3) × 10$^{-11}$ | 1.15 |
| ZP1$^b$ | 515, 7.9 | 507, 8.4 | 0.38 | 0.87 | 7.1(3) × 10$^{-11}$ | 1 |

Figure 30

| Sensor | $\lambda_{abs}$ (nm), $\varepsilon \times 10^3$ (M$^{-1}$cm$^{-1}$) | | $\phi_{apo}$ | $\phi_{Zn}$ | $K_{d\text{-}Zn}$ (M)$^c$ | Normalized $K_{d\text{-}Zn}$ |
|---|---|---|---|---|---|---|
| | Apo | Zn(II) | | | | |
| ZQ-MPP | 336, 5.3 | 360, 5.8 | ≤ 0.002 | 0.36±0.01 | 1.75 (1) × 10$^{-8}$ | 0.875 |
| TSQ | 336, 3.5 | 360, 3.5 | ≤ 0.002 | 0.34±0.03 | 2.00 (2) × 10$^{-8}$ | 1 |

ZINC-RESPONSIVE PEPTIDES, AND METHODS OF USE THEREOF

RELATED APPLICATIONS

This application claims the benefit of priority to U.S. Provisional Patent Application Ser. No. 61/586,424, filed Jan. 13, 2012, the contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Feb. 21, 2013, is named MTV-127.25 SL.txt and is 17,974 bytes in size.

GOVERNMENT SUPPORT

This invention was made with Government support under Grant No. R01 GM065519 awarded by the National Institutes of Health. The government has certain rights in this invention.

BACKGROUND OF THE INVENTION

Role of Mobile Zinc in Neurobiology

Zinc is the second most abundant metal ion in living systems. Its biological importance is accentuated by the fact that approximately 10% of the human genome is dedicated to the zinc proteome. Whereas the majority of zinc is highly regulated and tightly bound within protein scaffolds, a growing body of evidence suggests the presence of readily exchangeable or "mobile" zinc ("mZn") located within the pancreas, prostate, and brain. The importance of mZn in human health has been extensively documented, but knowledge of its physiology and pathology is incomplete. Taylor, C. G. *Biometals* 2005, 18, 305; et al. *Mol Cancer* 2006, 5, 17; Frederickson, C. J. et al. *Nat Rev Neurosci* 2005, 6, 449.

Fluorescent-based probes are the most common agents utilized to image mobile zinc within cellular environments. Que, E. L. et al. *Chem Rev* 2008, 108, 1517. Broadly speaking, zinc probes are divided into two categories: small molecule ("SM") sensors; and genetically encoded ("GE") sensors. SM-based probes offer a scaffold that is readily modified, providing sensors with chemical and physical properties that can be tuned for specific applications. On occasion SM probes can also display unpredictable subcellular distribution, which has led to controversy and confusion in biological communities. Kay, A. R. *Trends Neurosci* 2006, 29, 200. Conversely, GE sensors offer impressive control over the subcellular localization of the probe and are inherently biocompatible. Yet, GE probes suffer from the limited tunability of their metal-binding motifs, large sizes, and requirement of complex procedures for their incorporation into mammalian cells.

Metal ions are essential reactive cofactors, obligatory for carrying out complex chemical processes vital to cell metabolism. Yet, the reactive nature of metal ions requires tight regulation of their concentrations and cellular distribution. When unregulated, mobile metal ions have been implicated in multiple neurological disorders including Alzheimer's disease and amyotrophic lateral sclerosis (ALS). Frederickson, C. J. et al. *Nat Rev Neurosci* 2005, 6, 449.

In this context, it is surprising that large concentrations of mZn (~0.5 mM) occur in regions of the brain containing neuron cell bodies. Que, E. L. et al. *Chem Rev* 2008, 108, 1517. Although most of this zinc is "static"—i.e., tightly associated with a protein scaffold and serving both as structural and functional components in protein biochemistry—the existence of pools of mZn implies a functional role in neurological biochemistry. Bush, A. I. *Curr Opin Chem Biol* 2000, 4, 184. Zinc levels in the brain are non-uniformly distributed, with high concentrations occurring in the hippocampus, amygdala, and olfactory bulb. Id.

Recently, observations from the mossy fiber (mf) axons in the CA3 region of the hippocampus—an area of the brain responsible for learning and memory—suggested that the underlying mechanism behind zinc neurochemistry is both complex and nuanced. Zinc released from glutamatergic synaptic vesicles has been proposed to associate with zinc permeable gated channels, including N-methyl-D-aspartate (NMDA) receptors, voltage-gated calcium channels, and the calcium-permeable AMPA (α-amino-3-hydroxy-5-methyl-4-isoxazole propionic)/kainite channel ($Ca^{2+}$-A/K), where it can enter postsynaptic axons and/or function to inhibit postsynaptic mossy fiber long-term potentiation (mf-LTP). Frederickson, C. J. et al. *Nat Rev Neurosci* 2005, 6, 449; Pan, E. et al. *Neuron* 2011, 71, 1116. Portions of the released zinc have also been proposed to "re-enter" presynaptic termini through calcium-gated ion channels. Upon re-entry, zinc can transactivate the tyrosine kinase receptor (TrkB), independent of neurotrophins, initializing a chain of molecular events critical to both presynaptic mf-LTP and neuronal plasticity. Pan, E. et al. *Neuron* 2011, 71, 1116; Huang, Y. Z. et al. *Neuron* 2008, 57, 546. This "dual action" of vesicular zinc appears to be critical in regulating the effectiveness of mf-CA3 synapses and ensuring proper hippocampal function in health and disease, but the mechanistic details of its actions remain incomplete and highly debated.

Imaging Mobile Zinc

Divalent zinc is a good Lewis acid, redox inactive under physiological conditions, and able to adopt multiple binding geometries. Its $d^{10}$ closed-shell electronic structure renders zinc spectroscopically silent, complicating noninvasive in vivo imaging. Currently, fluorescent probes provide the most facile way to image zinc within a cellular environment. Tomat, E. et al. *Curr Opin Chem Biol* 2010, 14, 225.

One such family of zinc probes is the ZinPyr (ZP) family of sensors first reported by in 2000. Walkup, G. K. et al. *J Am Chem Soc* 2000, 122, 5644. ZP1 is based on a fluorescein platform that is further modified with two dipicolylamine (DPA) "metal-binding arms", which function to quench fluorescein emissions via photoinduced electron transfer (PET) in the metal-free form. Upon coordination to zinc, the electronic configuration of ZP1 changes, resulting in an attenuation of the PET effect and recovery of fluorescein emissive properties. ZP1 has several attributes that make it a model probe: (1) it is formed in a high yielding, "one-pot", Mannich reaction between 2',7'-dichlorofluorescein and the iminium ion condensation product of formaldehyde and DPA; (2) it is a zinc selective "turn on" sensor, meaning it is non-responsive to the presence of other biologically relevant metal ions such as $Ca^{2+}$, $Mg^{2+}$, $Mn^{2+}$, $Cu^{2+}$, or $Fe^{2+}$; and (3) it is excitable with visible (~500 nm) light, making it compatible with the 488 nm argon line of most fluorescence microscopes, as well as reducing background fluorescence attributed to biological auto-fluorescence. To date, a library of sensors in the ZP family, and an extensive group of related ZS, QZ and ZPP derivatives have been synthesized, allowing access to probes with a wide range of zinc-binding affinities and dynamic ranges. Nolan, E. M. et al. *Acc Chem Res* 2009, 42, 193; Pluth, M. D. et al. *Annu Rev Biochem* 2011, 80, 333. The ZP family of probes has been well documented to function in cellular systems, such as HeLa, hippocampal slices, and pancreatic β-insulinoma cells, and even in live animals (TRAMP—a mouse model of prostate cancer), demonstrating their practical utility in addressing biological questions. Nolan, E. M. et al. *Acc Chem Res* 2009, 42, 193; Ghosh, S. K. et al. *Cancer Res* 2010, 70, 6119.

Proteins and Peptides as Zinc Sensor Scaffolds

Proteins are among the most versatile biomolecules. Their ability to arrange chemically diverse functional groups in a three dimensional architecture enables them to carry out complex chemical transformations with a reactivity and selectivity unparalleled in synthetic systems. Moreover, the large and relatively featureless surface of most proteins necessitated the evolution of numerous weak but additive interactions conferring the ability to form tight and specific connections with other biomolecules, such as cell receptors, nucleic acids, and cofactors, even within the crowded cellular environment. This biological specificity has led to the use of proteins and peptides as therapeutics, drug delivery vehicles, and metal sensors. Previously, development of peptide-based zinc sensors mainly involved the reengineering of small metal-binding proteins, most notably the zinc finger fold. Godwin, H. A. et al. *J Am Chem Soc* 1996, 118, 6514; Shults, M. D. et al. *J Am Chem Soc* 2003, 125, 10591; Walkup, G. K. et al. *J Am Chem Soc* 1996, 118, 3053; Walkup, G. K.; Imperiali, B. *J Am Chem Soc* 1997, 119, 3443. This seminal work invigorated the nascent field of peptide-based biosensors by highlighting the way natural and/or non-natural components could be "mixed-and-matched," achieving sensors that retained biological activity and specificity while reporting on targeted analytes. From a zinc sensor perspective, these probes were limited by the UV excitation of the fluorophores, narrow range of metal-binding affinities, or metal-induced self-assembly/aggregation of the sensor. In other words, these characteristics prevented their wider use and acceptance in biological communities.

The introduction of green fluorescent protein (GFP) variants has led to the creation of GE metal-sensor proteins. Metal-sensor proteins can readily be made ratiometric by joining photophysically complementary GFP variants together with a short peptide sequence that mimics the metal-binding region of a natural metal-binding protein (e.g., Atox1, MTIIa, and Zif268). GE sensors have been successfully applied intracellularly to measure the concentration and spatial distribution of mZn, as well as subcellularly, to determine mZn levels in the ER and Golgi. Dittmer, P. J. et al. *J Biol Chem* 2009, 284, 16289; Vinkenborg, J. L. et al. *Nat Methods* 2009, 6, 737; Qin, Y. et al. *Proc Natl Acad Sci USA* 2011, 108, 7351. Although GE probes obviate complications surrounding probe internalization, subcellular localization, and biological compatibility, they have narrow wavelength availability, relatively low photochemical stability, and limited chemical diversity. Pazos, E. et al. *Chem Soc Rev* 2009, 38, 3348.

There exists a need for a new class of zinc sensors that couple the chemical and physical characteristics of small-molecule based probes with the biological specificity of peptide scaffolds.

SUMMARY OF THE INVENTION

In certain embodiments, the invention relates to an amino acid compound, comprising a sensor moiety, a first linker, and a first amino acid, wherein the first amino acid is a natural amino acid or a non-natural amino acid.

In certain embodiments, the invention relates to any one of the aforementioned amino acid compounds, wherein the sensor moiety is a fluorophore.

In certain embodiments, the invention relates to any one of the aforementioned amino acid compounds, wherein the sensor moiety is a derivative of any one of the sensors described in U.S. Pat. Nos. 7,160,732; 7,018,840; 7,399,639; 7,615,377; 7,488,820; and 7,494,821; all of which are incorporated by reference in their entireties.

In certain embodiments, the invention relates to any one of the aforementioned amino acid compounds, wherein the sensor moiety is a fluorescein derivative.

In certain embodiments, the invention relates to any one of the aforementioned amino acid compounds, wherein the sensor moiety is selected from the group consisting of

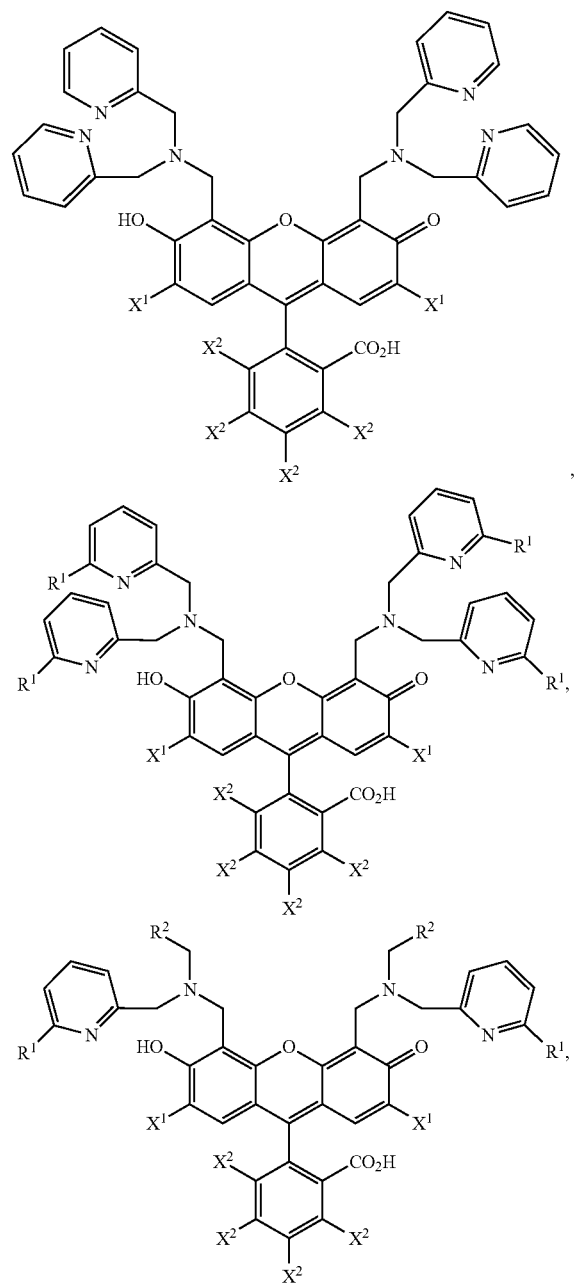

5
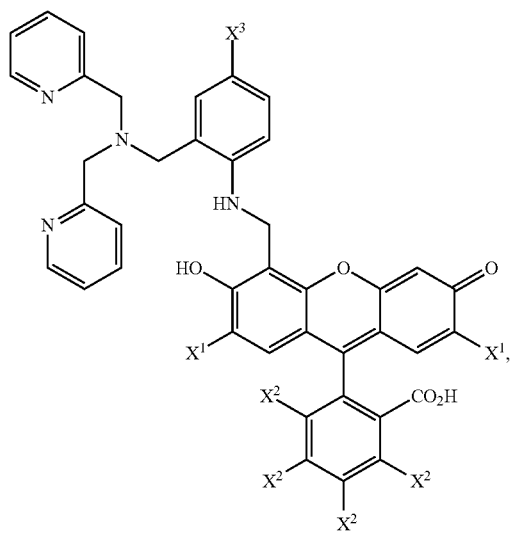
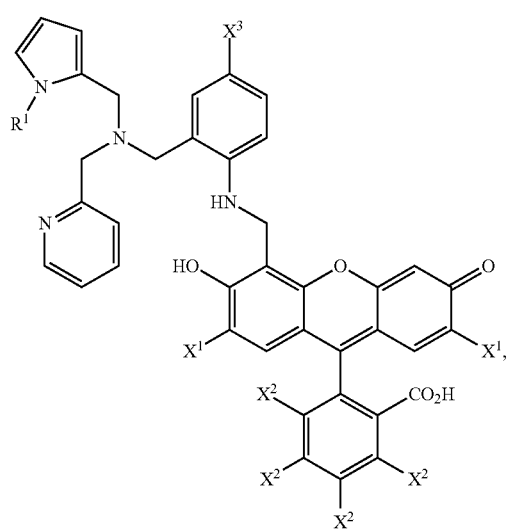
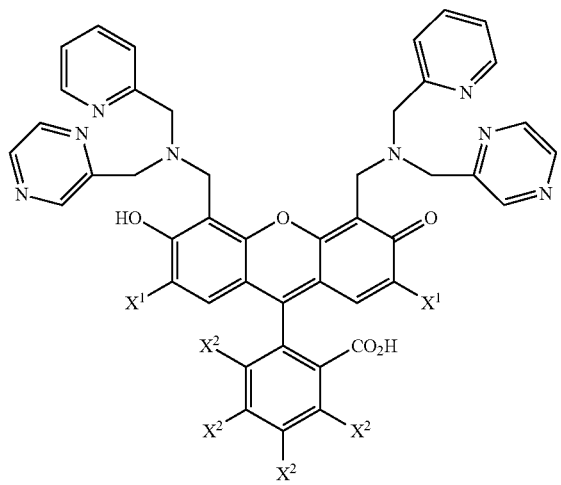
6
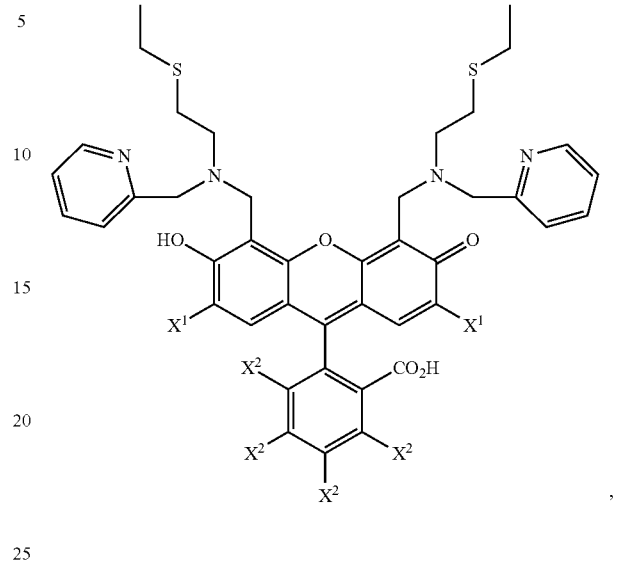
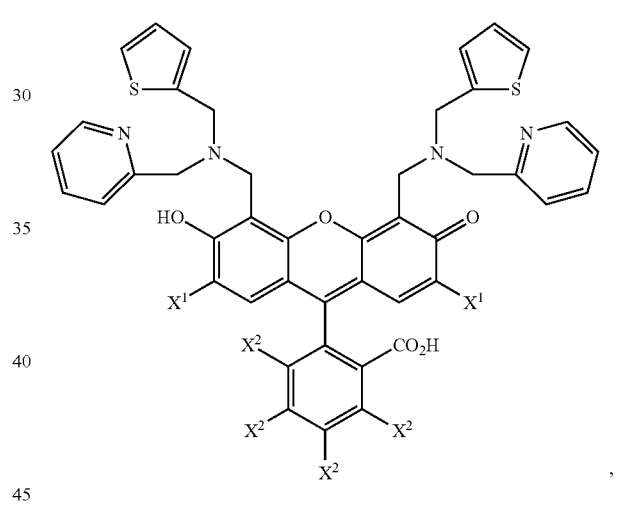
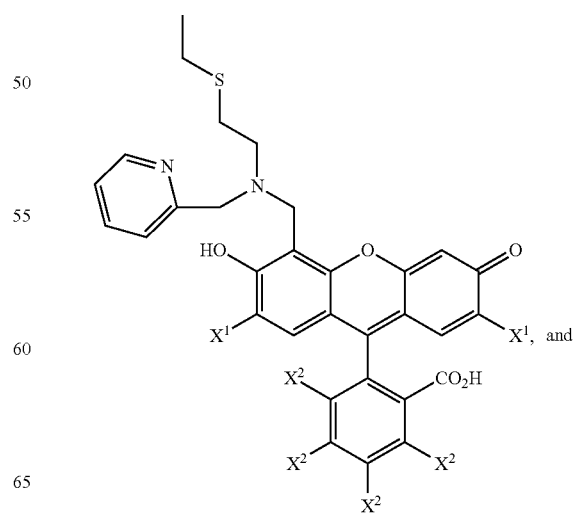

-continued

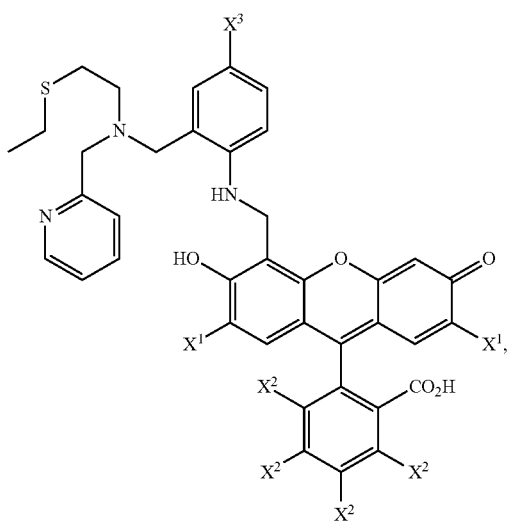

wherein, independently for each occurrence, $X^1$ is —H, —F, or —Cl;

$X^2$ is —H, —F, —Cl, —CO$_2$R', —C(O)-linker, -linker, —NR$^1$-linker, or —S-linker, wherein at least one instance of $X^2$ is —C(O)-linker, -linker, —NR$^1$-linker, or —S-linker;

$X^3$ is —H, —F, —Cl, or —OR$^1$;

$R^1$ is —H or alkyl; and $R^2$ is —H or phenyl.

In certain embodiments, the invention relates to an amino acid compound selected from the group consisting of

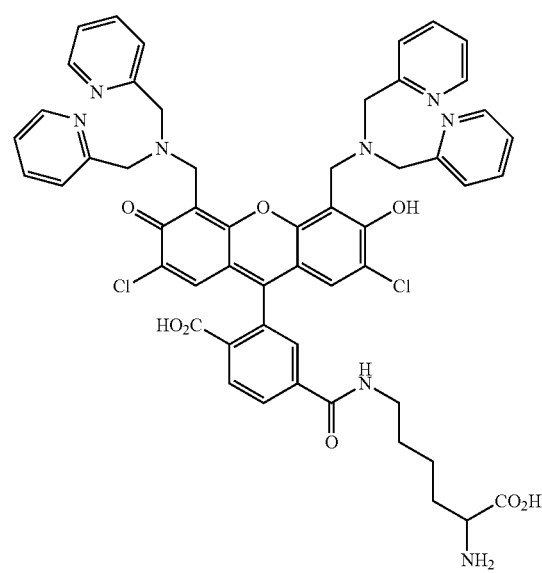

and

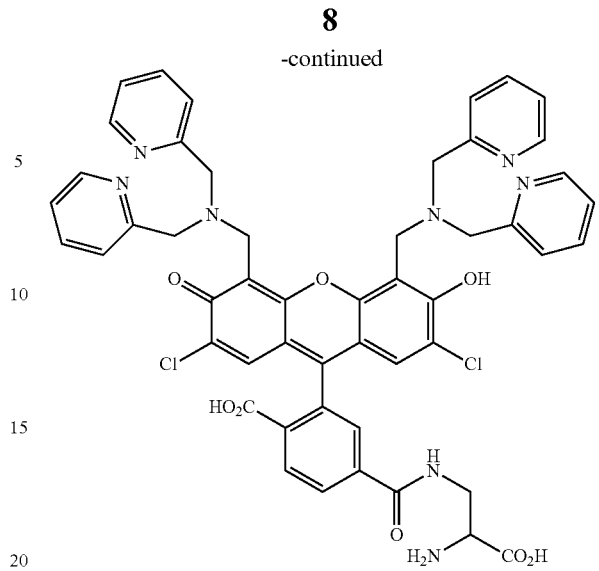

In certain embodiments, the invention relates to any one of the aforementioned amino acid compounds, wherein the sensor moiety is a zinquin derivative.

In certain embodiments, the invention relates to any one of the aforementioned amino acid compounds, wherein the sensor moiety is

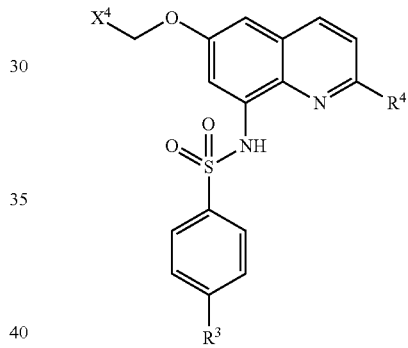

wherein $R^3$ is H, alkyl, or —CO$_2$H;

$R^4$ is H or alkyl;

$X^4$ is —C(O)-linker, -linker, —NR$^1$-linker, or —S-linker; and $R^1$ is —H or alkyl.

In certain embodiments, the invention relates to any one of the aforementioned amino acid compounds, wherein the amino acid compound has the following formula:

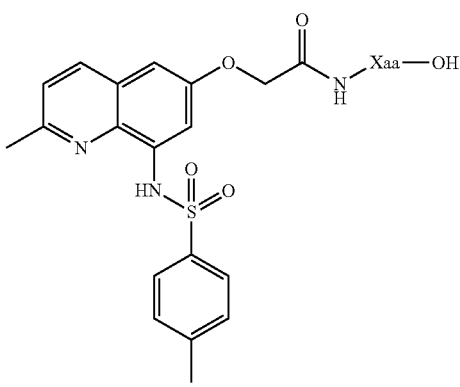

wherein Xaa is a natural amino acid or a non-natural amino acid.

In certain embodiments, the invention relates to a peptide, wherein the peptide comprises at least one of the aforementioned amino acid compounds; and a second amino acid, wherein the second amino acid is a natural amino acid or a non-natural amino acid.

In certain embodiments, the invention relates to a peptide, wherein the peptide comprises at least one of the aforementioned amino acid compounds, a second amino acid, and a detectable moiety, wherein the second amino acid is a natural amino acid or a non-natural amino acid.

In certain embodiments, the invention relates to any one of the aforementioned peptides, wherein the detectable moiety is a donor chromophore or an acceptor chromophore.

In certain embodiments, the invention relates to any one of the aforementioned peptides, wherein the detectable moiety is a phosphorescent moiety or a fluorescent moiety.

In certain embodiments, the invention relates to a method of quantifying an amount of a substance in a cell, comprising the steps of:
  contacting the cell with any one of the aforementioned peptides; and
  detecting a signal, wherein the signal emitted by the peptide in the presence of the substance is different than the signal emitted by the peptide in the absence of the substance.

In certain embodiments, the invention relates to a method of quantifying an amount of a substance in a specific locale of a cell, comprising the steps of:
  contacting the cell with any one of the aforementioned peptides; and
  detecting a signal from a specific locale of a cell, wherein the signal emitted by the peptide in the presence of the substance is different than the signal emitted by the peptide in the absence of the substance.

In certain embodiments, the invention relates to a method of quantifying an amount or determining a location of a substance in a subject, comprising the steps of:
  administering to the subject any one of the aforementioned peptides; and
  detecting a signal, wherein the signal emitted by the peptide in the presence of the substance is different than the signal emitted by the peptide in the absence of the substance.

BRIEF DESCRIPTION OF THE FIGURES

FIG. 8 depicts a computer model of ratio-ZRP-2, which has zinc binding and photophysical properties specifically tuned to investigate zinc metalloneurochemistry in the hippocampus.

FIG. 9 tabulates proposed sequences for intra-, extra-, and subcellular localization of ZRPs. $^a$Amino acid sequences are given using single-letter abbreviations (SEQ ID NOS 1-6, respectively, in order of appearance).

FIG. 29 tabulates the photophysical and zinc-binding properties of Palm-ZP1 and ZP1. [a]Spectroscopic data and apparent zinc dissociation constants ($D_{d-Zn}$) were determined in 25 mM PIPES buffer (pH 7) with 50 mM KCl and 50% (v/v) acetonitrile. [b]Quantum yield, absorption, and extinction coefficient values were taken from literature (Nolan, E. M.; et al. Acc. Chem. Res. 2009, 42, 193). [c]For comparison, the for ZP1 was determined under identical conditions. ZP1 has a known $K_{d-Zn}$ of 0.7 nM, in 50 mM PIPES buffer (pH 7), 100 mM KCl.

FIG. 30 tabulates the photophysical and zinc-binding properties of ZQ-MPP and TSQ. [a]Spectroscopic data and apparent zinc dissociation constants ($K_{d-Zn}$) were determined in 25 mM PIPES buffer (pH 7) with 50 mM KCl and 50% (v/v) acetonitrile. [b]Quantum yield, absorption, and extinction coefficient values were taken from literature. [c]For comparison, the for TSQ was determined under identical conditions.

DETAILED DESCRIPTION OF THE INVENTION

Overview

Figure 1:
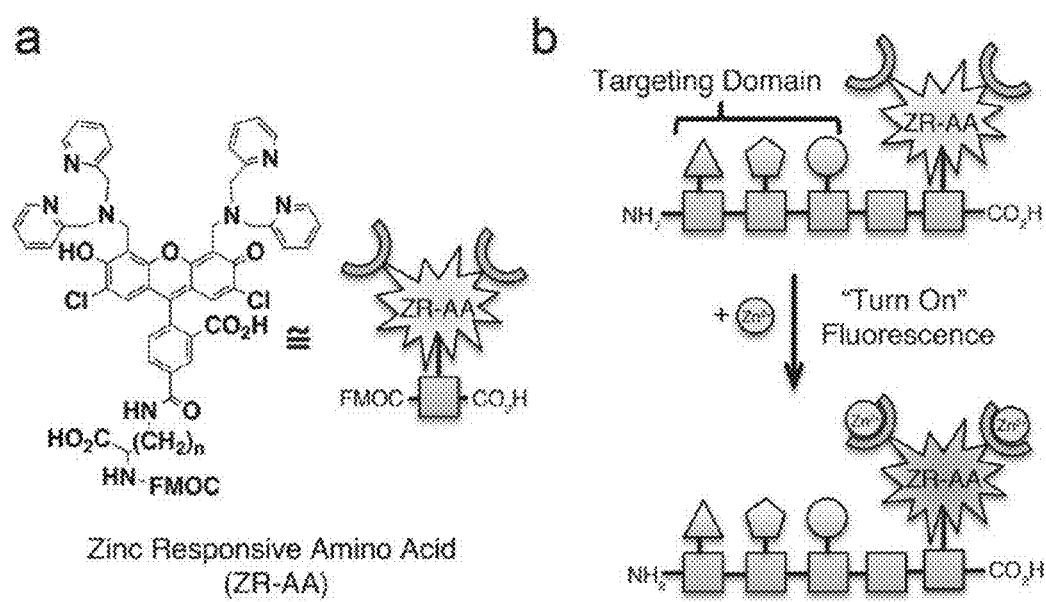
FIG. 1 is (a) a line drawing and a cartoon representation of a ZR-AA based on ZinPyr-1; and (b) a cartoon schematic of a zinc responsive peptide (ZRP) that couples the metal sensing capability of small-molecule sensors with the biological targeting ability of peptides.

In certain embodiments, the invention relates to a zinc-responsive peptide (ZRP). In certain embodiments, the invention relates to a method of preparing a ZRP. In certain embodiments, ZRPs are prepared by solid phase peptide synthesis (SPPS), through any one of three parallel routes: (i) independent synthesis of a non-natural zinc responsive amino acid (ZR-AA) that features a member of the ZinPyr (ZP) family of sensors, as a zinc-responsive sidechain (FIG. 1a); (ii) incorporation of the ZP group onto the N-terminus of the peptide backbone; or (iii) coupling the ZP group to the primary amine sidechain of an amino acid (e.g., Lys, Orn, or Dap) by selective deprotection on the resin of the amine protecting group.

Figure 2:
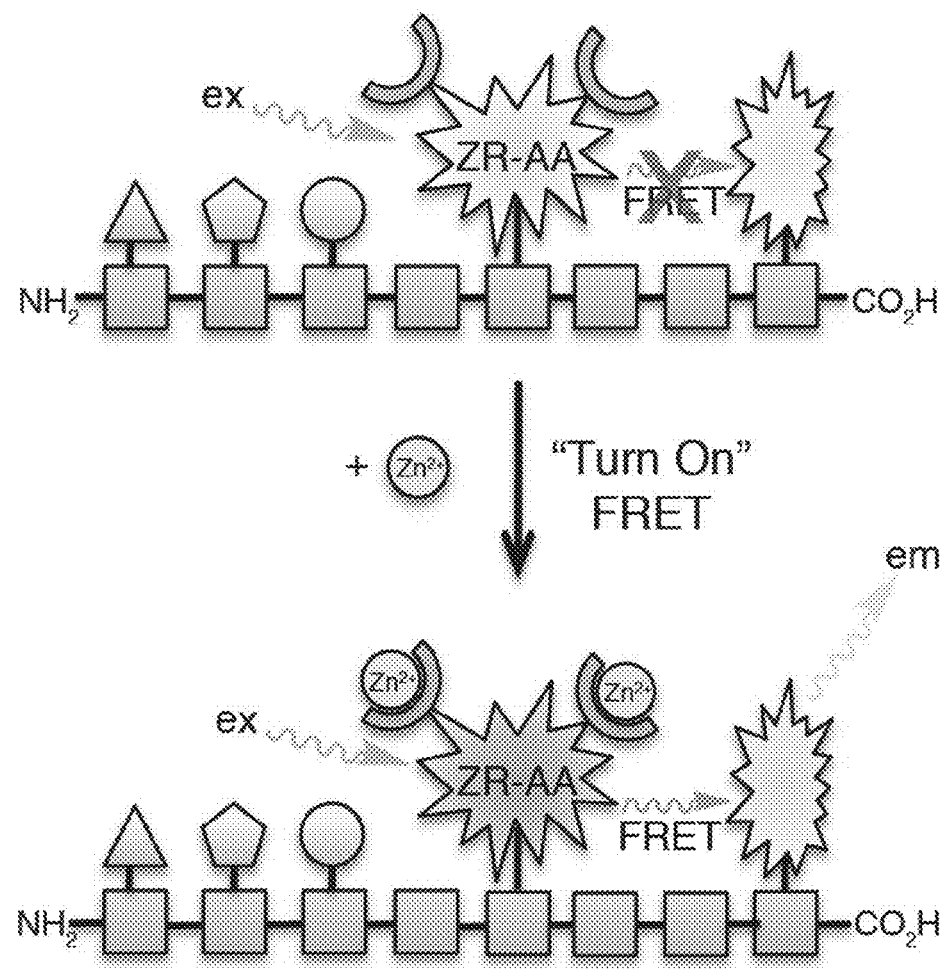
FIG. 2 is an illustration depicting how ZRPs can be made ratiometric by incorporating a FRET partner into the peptide along with the ZR-AA.

In certain embodiments, the invention relates to a ratiometric ZRP, wherein the ratiometric ZRP comprises a fluorophore and a ZR-AA. In certain embodiments, the fluorophore is compatible with the fluorescein base of the ZR-AA. In certain embodiments, the fluorophore is coumarin or a coumarin derivative. In certain embodiments, the fluorophore is rhodamine or a rhodamine derivative. See, for example, FIG. 2. In certain embodiments, the ratiometric ZRP comprises a plurality of fluorescent probes.

In certain embodiments, the invention relates to a method of quantifying an amount of mZn in a cell. In certain embodiments, the invention relates to a method of quantifying an amount of mZn in a specific cellular locale. In certain embodiments, the specific cellular locale is an intracellular probe, an extracellular probe, a trans-Golgi network, a mitochondrion, or an endoplasmic reticulum. In certain embodiments, the cell is a HeLa cell, HEK, or a neuron.

In certain embodiments, the invention relates to a method of quantifying an amount of mZn in a subject. In certain embodiments, the invention relates to a method of quantifying the amount of mZn released from the hippocampus. In certain embodiments, the mZn is released from the CA3 region of the hippocampus. In certain embodiments, the mZn is released from presynaptic mossy fibers in the CA3 region of the hippocampus.

In certain embodiments, the invention relates to a method of determining the destination of mZn. In certain embodiments, the invention relates to a method of determining the destination of mZn released from the hippocampus. In certain embodiments, the mZn is released from the CA3 region of the hippocampus. In certain embodiments, the mZn is released from presynaptic mossy fibers in the CA3 region of the hippocampus.

In certain embodiments, the invention relates to a method of determining the role of mZn in glutamatergic synaptic vesicles in hippocampal mossy fibers (mf).

In certain embodiments, the invention relates to any one of the aforementioned methods, comprising the step of: contacting any one of the aforementioned ZRPs with a hippocampus. In certain embodiments, the ZRP has the ability to quantify mZn. In certain embodiments, the hippocampus is a mouse hippocampus or a rat hippocampus. In certain embodiments, the ZRP is directed to the synaptic cleft. In certain embodiments, the ZRP is directed to a specific intracellular locale. In certain embodiments, the specific intracellular locales are mf buttons.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

Exemplary Responsive Amino Acids

In certain embodiments, the invention relates to an amino acid compound, comprising a sensor moiety, a first linker, and a first amino acid, wherein the first amino acid is a natural amino acid or a non-natural amino acid.

In certain embodiments, the invention relates to any one of the aforementioned amino acid compounds, wherein the sensor moiety is a fluorophore.

In certain embodiments, the invention relates to any one of the aforementioned amino acid compounds, wherein the sensor moiety is a derivative of any one of the sensors described in U.S. Pat. Nos. 7,160,732, 7,018,840, 7,399,639, 7,615,377, 7,488,820, or 7,494,821, all of which are incorporated by reference in their entireties.

In certain embodiments, the invention relates to any one of the aforementioned amino acid compounds, wherein the sensor moiety is a derivative of a compound represented by Formula 1A or Formula 2A:

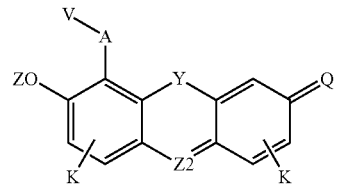

Formula 1A

-continued

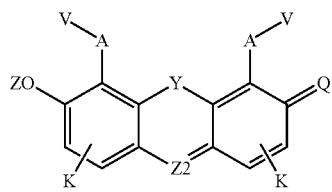

Formula 2A wherein

A is a diradical having one or more carbon atoms;

Z is hydrogen or a hydroxyl-protecting group;

Q is O, S, or Se;

K is optionally one or more substituents of the indicated aromatic ring;

V is a Lewis base;

Y is O, S, Se, $NR^1$, or $C(R^1)_2$;

Z2 is N, $HOOCCH_2CH_2C-$, $HOOC-CH=CH-C-$, (2-carboxyphenyl)-C—, (2-sulfophenyl)-C—, (2-carboxy-3,4,5,6-tetrachlorophenyl)-C—, (2-carboxy-4-nitrophenyl)-C—, (2-carboxy-5-nitrophenyl)-C—, (2-carboxy-4-aminophenyl)-C—, (2-carboxy-5-aminophenyl)-C—, (2,4-dicarboxyphenyl)-C—, (2,5-dicarboxylphenyl)-C—, (2,4,5-tricarboxyphenyl)-C—, and other substituted (2-carboxyphenyl)-C— moieties; and $R^1$ is —H or alkyl.

In certain embodiments, the invention relates to any one of the aforementioned amino acid compounds, wherein the sensor moiety is a fluorescein derivative.

In certain embodiments, the invention relates to any one of the aforementioned amino acid compounds, wherein the sensor moiety is selected from the group consisting of

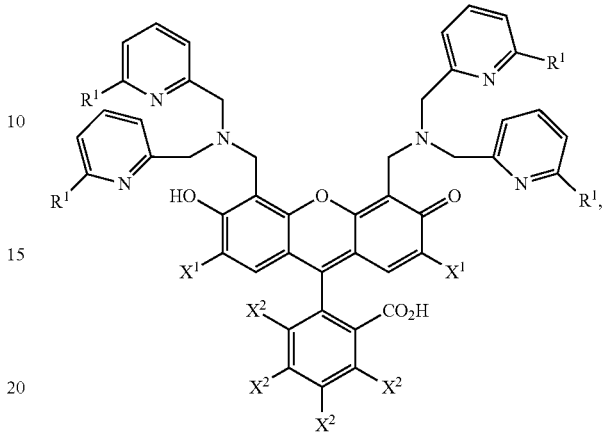

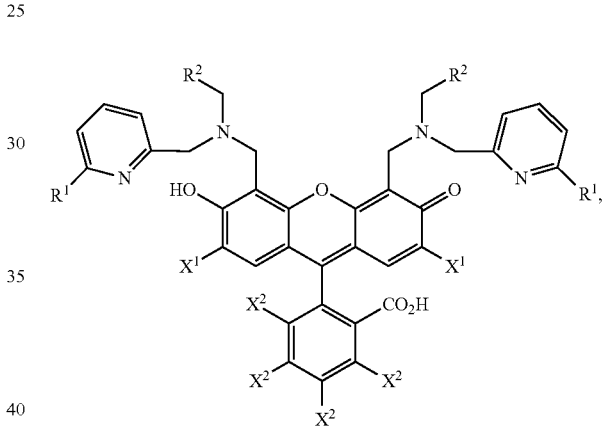

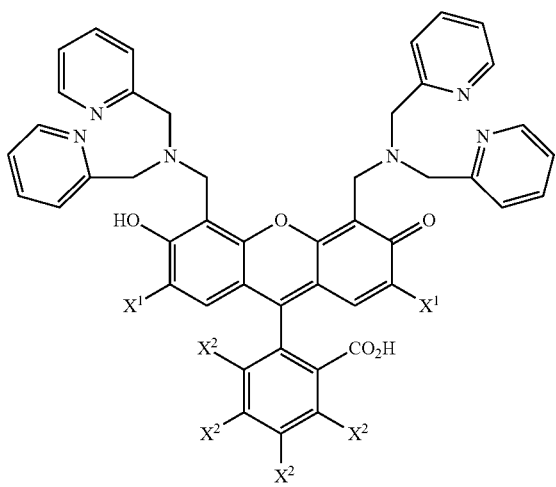

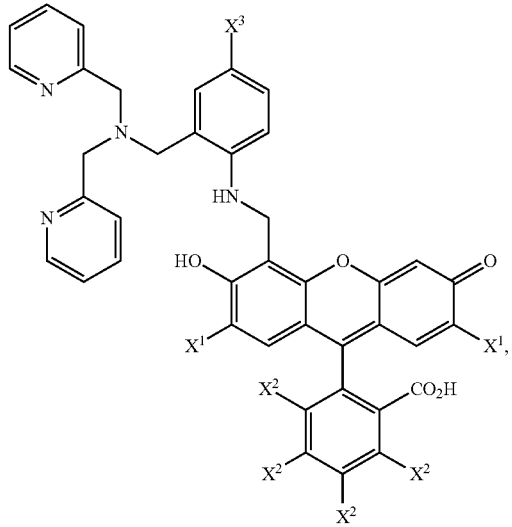

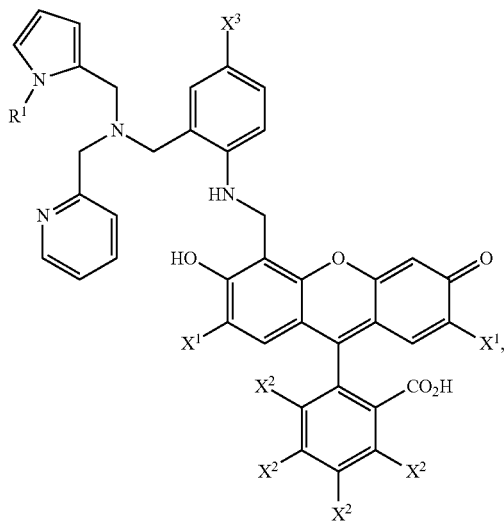
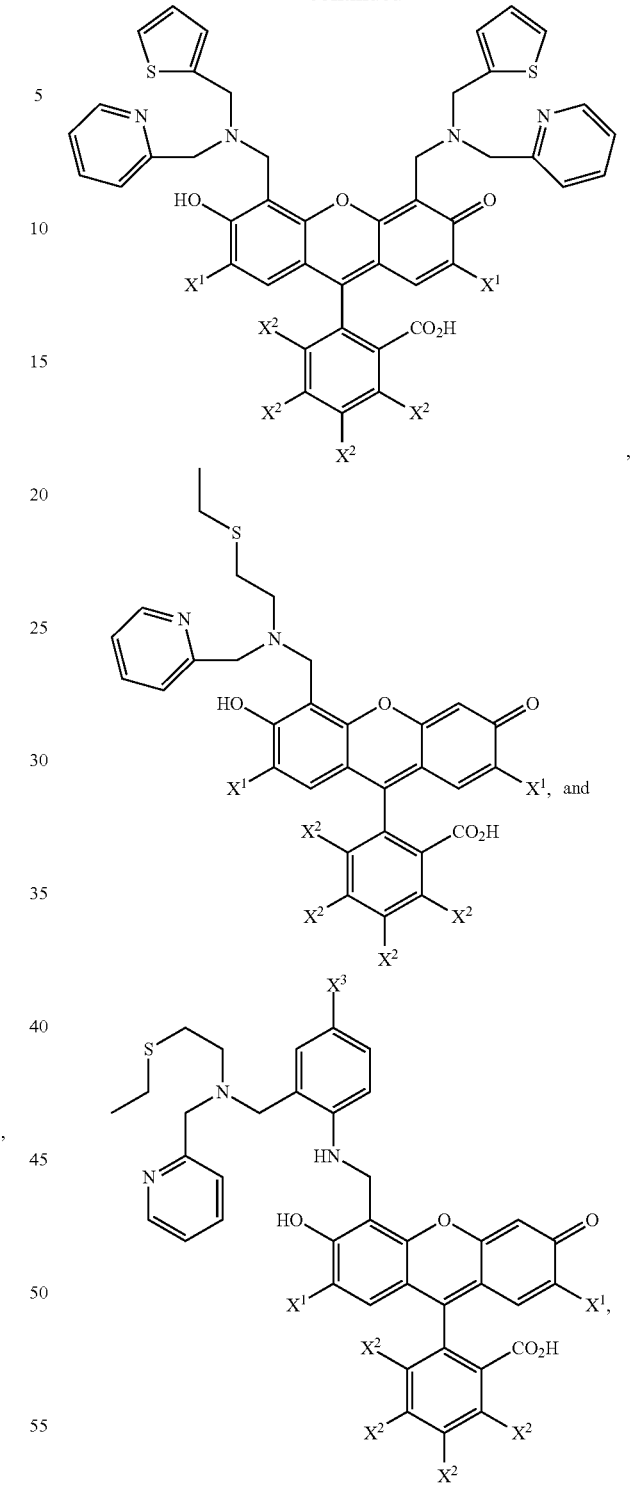
wherein, independently for each occurrence,
X[1] is —H, —F, or —Cl;
X[2] is —H, —F, —Cl, —CO$_2$R[1], —C(O)-linker, -linker, —NR[1]-linker, or —S-linker, wherein at least one instance of X[2] is —C(O)-linker, -linker, —NR[1]-linker, or —S-linker;
X[3] is —H, —F, —Cl, or —OR[1];
R[1] is —H or alkyl; and
R[2] is —H or phenyl.

In certain embodiments, the invention relates to any one of the aforementioned amino acid compounds, wherein the sensor moiety is selected from the group consisting of

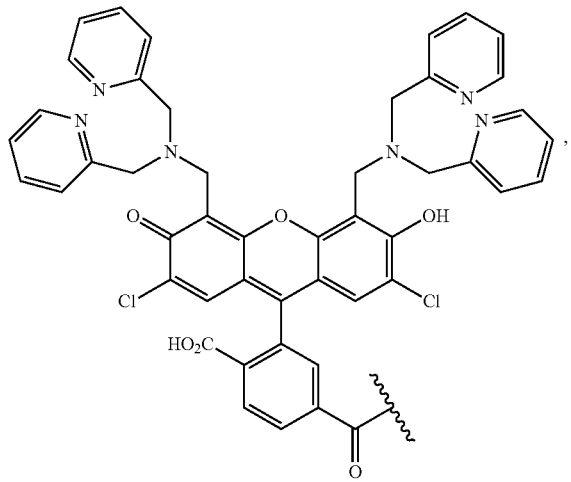

,

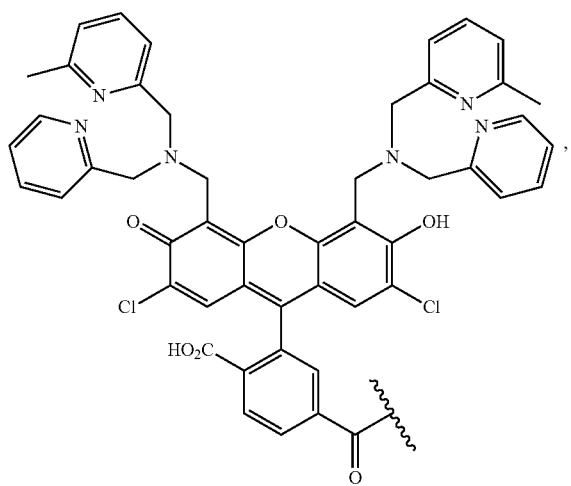

,

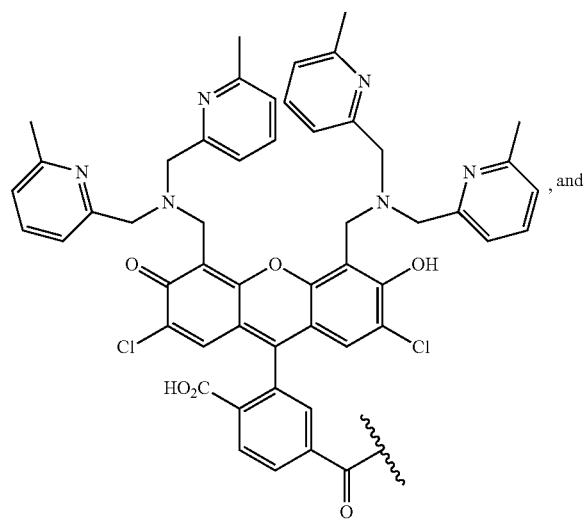

, and

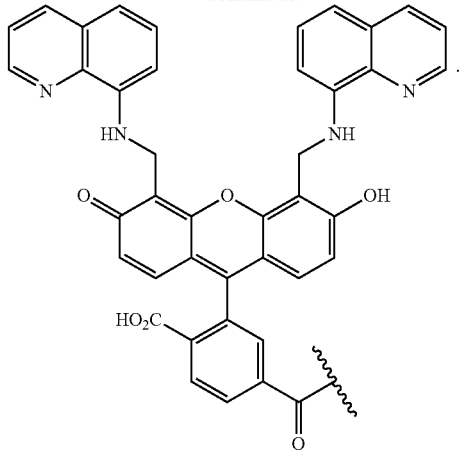 [SMILES: *C(=O)c1ccc(C(=O)O)c(-c2c3ccc(=O)c(CNc4cccc5cccnc45)c-3oc3c(CNc4cccc5cccnc45)c(O)ccc23)c1]

.

In certain embodiments, the invention relates to any one of the aforementioned amino acid compounds, wherein the sensor moiety is a derivative of a compound represented by Formula 3:

Formula 3

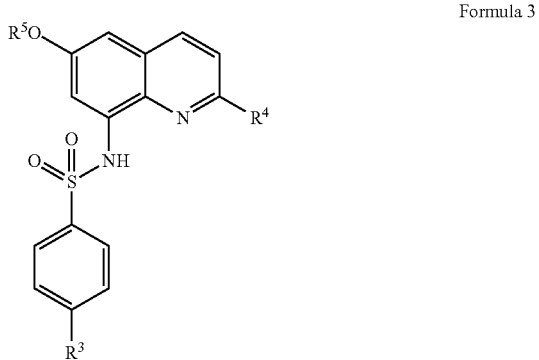

wherein
$R^3$ is H, alkyl, or —$CO_2H$;
$R^4$ is H or alkyl; and
$R^5$ is H, alkyl, or -alkyl-$CO_2H$.

In certain embodiments, the invention relates to any one of the aforementioned amino acid compounds, wherein the sensor moiety is a zinquin derivative.

In certain embodiments, the invention relates to any one of the aforementioned amino acid compounds, wherein the sensor moiety is

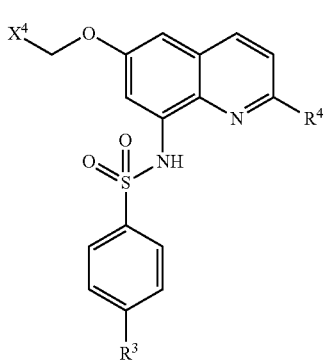

wherein
$R^3$ is H, alkyl, or —$CO_2H$;
$R^4$ is H or alkyl;

$X^4$ is —C(O)-linker, -linker, —NR$^1$-linker, or —S-linker; and $R^1$ is —H or alkyl.

In certain embodiments, the invention relates to any one of the aforementioned amino acid compounds, wherein the sensor moiety is

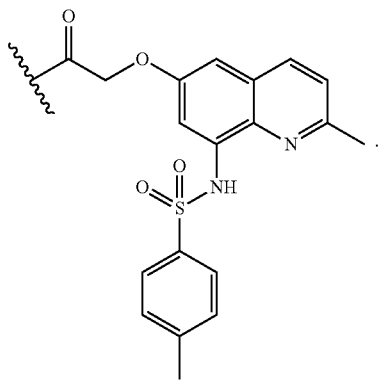 [SMILES: *C(=O)COc1cc(NS(=O)(=O)c2ccc(C)cc2)c2nc(C)ccc2c1]

In certain embodiments, the invention relates to any one of the aforementioned amino acid compounds, wherein the first amino acid is a natural α-amino acid or a non-natural α-amino acid.

In certain embodiments, the invention relates to any one of the aforementioned amino acid compounds, wherein the first amino acid is a natural α-amino acid.

In certain embodiments, the invention relates to any one of the aforementioned amino acid compounds, wherein the first amino acid is a non-natural α-amino acid.

In certain embodiments, the invention relates to any one of the aforementioned amino acid compounds, wherein the first amino acid is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, or 2,3-diaminopropionic acid (DAP).

In certain embodiments, the invention relates to any one of the aforementioned amino acid compounds, wherein the first amino acid is lysine, 2,3-diaminopropionic acid, or glycine.

In certain embodiments, the invention relates to any one of the aforementioned amino acid compounds, wherein the first linker is an amide bond, a disulfide bond, a thioether bond, a thiourea, or a triazole.

In certain embodiments, the invention relates to any one of the aforementioned amino acid compounds, wherein the first linker is an amide bond.

In certain embodiments, the invention relates to any one of the aforementioned amino acid compounds, wherein the amino acid compound has the following formula:

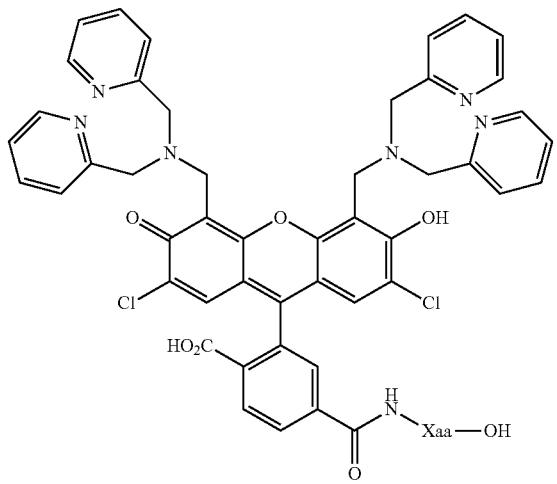

wherein Xaa is a natural amino acid or a non-natural amino acid.

In certain embodiments, the invention relates to any one of the aforementioned amino acid compounds, wherein Xaa is a natural α-amino acid or a non-natural α-amino acid.

In certain embodiments, the invention relates to any one of the aforementioned amino acid compounds, wherein Xaa is a natural α-amino acid.

In certain embodiments, the invention relates to any one of the aforementioned amino acid compounds, wherein Xaa is a non-natural α-amino acid.

In certain embodiments, the invention relates to any one of the aforementioned amino acid compounds, wherein Xaa is glycine.

In certain embodiments, the invention relates to any one of the aforementioned amino acid compounds, wherein the amino acid compound has the following formula:

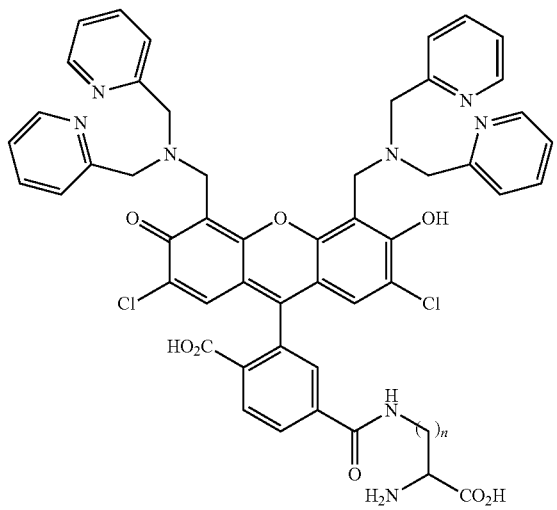

wherein n is 1, 2, 3, 4, 5, or 6.

In certain embodiments, the invention relates to any one of the aforementioned amino acid compounds, wherein the amino acid compound has the following formula:

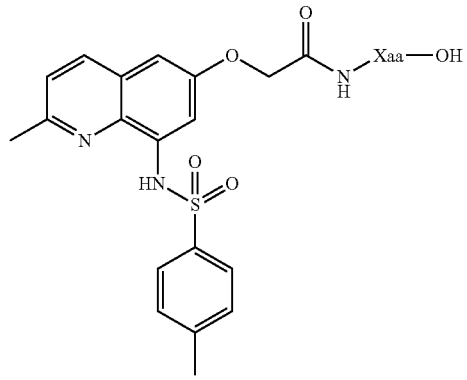

wherein Xaa is a natural amino acid or a non-natural amino acid.

In certain embodiments, the invention relates to any one of the aforementioned amino acid compounds, wherein Xaa is cyclohexylalanine.

In certain embodiments, the invention relates to an amino acid compound selected from the group consisting of

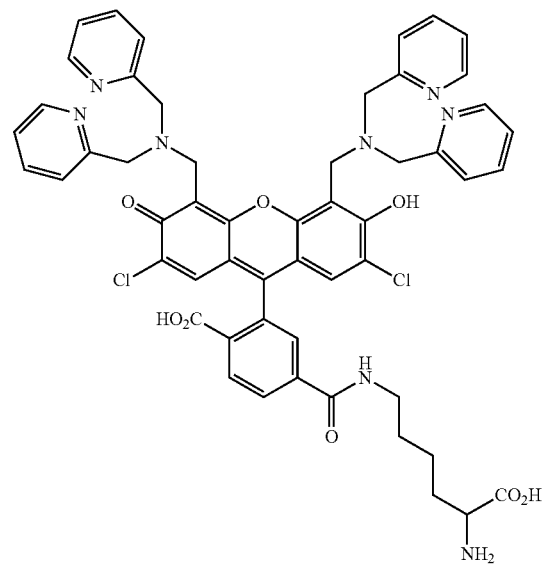

and

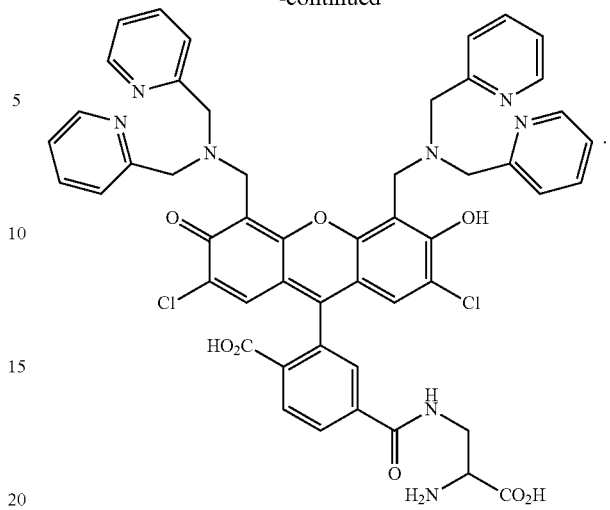

Exemplary Responsive Peptides

In certain embodiments, the invention relates to a peptide, wherein the peptide comprises at least one of the aforementioned amino acid compounds; and a second amino acid, wherein the second amino acid is a natural amino acid or a non-natural amino acid.

In certain embodiments, the invention relates to any one of the aforementioned peptides, wherein the second amino acid is a natural α-amino acid or a non-natural α-amino acid.

In certain embodiments, the invention relates to any one of the aforementioned peptides, wherein the second amino acid is a natural α-amino acid.

In certain embodiments, the invention relates to any one of the aforementioned peptides, wherein the second amino acid is a non-natural α-amino acid.

In certain embodiments, the invention relates to any one of the aforementioned peptides, wherein the peptide comprises the following formula (N-terminus→C-terminus):

$(Xaa)_p$-first amino acid-$(Xaa)_p$     (SEQ ID NO: 9)

wherein, independently for each occurrence,
the sensor moiety is covalently bonded to the side chain of the first amino acid via the first linker;
p is 0-10 inclusive;
at least one occurrence of p is not zero; and
Xaa is a natural amino acid or a non-natural amino acid.

In certain embodiments, the invention relates to any one of the aforementioned peptides, wherein Xaa is a natural α-amino acid or a non-natural α-amino acid.

In certain embodiments, the invention relates to any one of the aforementioned peptides, wherein Xaa is a natural α-amino acid.

In certain embodiments, the invention relates to any one of the aforementioned peptides, wherein Xaa is a non-natural α-amino acid.

In certain embodiments, the invention relates to any one of the aforementioned peptides, wherein the second amino acid or Xaa is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, or 2,3-diaminopropionic acid (DAP).

In certain embodiments, the invention relates to any one of the aforementioned peptides, wherein the second amino acid or Xaa is lysine, 2,3-diaminopropionic acid, or glycine.

In certain embodiments, the invention relates to any one of the aforementioned peptides, wherein the peptide comprises the following formula:

RGD-first amino acid-first linker-sensor moiety    (SEQ ID NO: 10)

wherein
the sensor moiety is covalently bonded to the side chain of the first amino acid via the first linker;
the first amino acid is 2,3-diaminopropionic acid;
the first linker is an amide; and the sensor moiety is

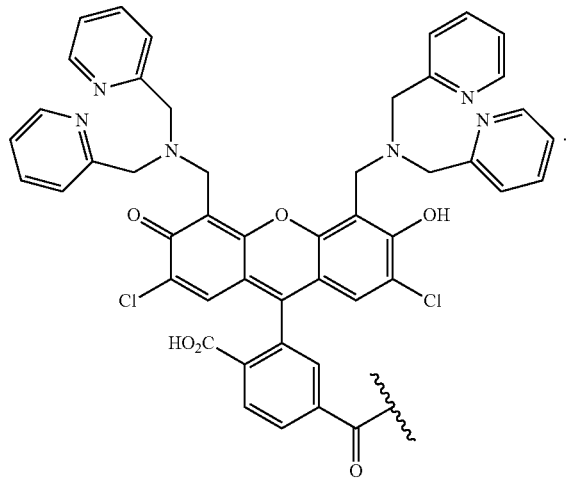 [SMILES: *C(=O)c1ccc(C(=O)O)c(-c2c3cc(Cl)c(=O)c(CN(Cc4ccccn4)Cc4ccccn4)c-3oc3c(CN(Cc4ccccn4)Cc4ccccn4)c(O)c(Cl)cc23)c1]

In certain embodiments, the invention relates to any one of the aforementioned peptides, wherein the peptide comprises the following formula (N-terminus→C-terminus):

H$_3$C—(CH$_2$)$_{14}$—C(O)-(Xaa)$_p$-first amino acid-NH$_2$    (SEQ ID NO: 11)

wherein
p is 0-10 inclusive;
the sensor moiety is covalently bonded to the side chain of the first amino acid via the first linker;
the first amino acid is lysine;
the first linker is an amide; and
the sensor moiety is

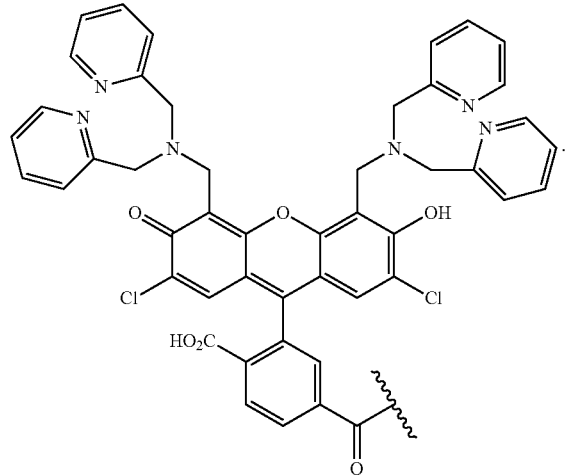 [SMILES: *C(=O)c1ccc(C(=O)O)c(-c2c3cc(Cl)c(=O)c(CN(Cc4ccccn4)Cc4ccccn4)c-3oc3c(CN(Cc4ccccn4)Cc4ccccn4)c(O)c(Cl)cc23)c1]

In certain embodiments, the invention relates to any one of the aforementioned peptides, wherein the peptide comprises the following formula (N-terminus→C-terminus):

sensor moiety-first linker-first amino acid-(Xaa)$_p$-NH$_2$    (SEQ ID NO: 12)

wherein
p is 0-10 inclusive;
the sensor moiety is covalently bonded to the N-terminus of the first amino acid via the first linker;
the first amino acid is cyclohexylamine;
the first linker is an amide; and
the sensor moiety is

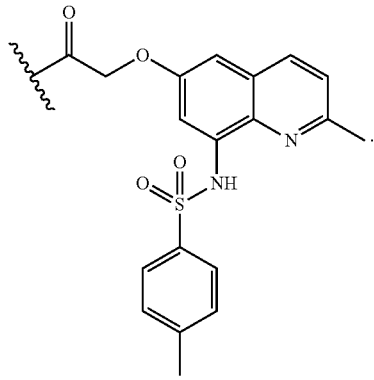 [SMILES: *C(=O)COc1cc(NS(=O)(=O)c2ccc(C)cc2)c2nc(C)ccc2c1]

In certain embodiments, the invention relates to a peptide, wherein the peptide comprises at least one of the aforementioned amino acid compounds, a second amino acid, and a detectable moiety, wherein the second amino acid is a natural amino acid or a non-natural amino acid.

In certain embodiments, the invention relates to any one of the aforementioned peptides, wherein the second amino acid is a natural α-amino acid or a non-natural α-amino acid.

In certain embodiments, the invention relates to any one of the aforementioned peptides, wherein the second amino acid is a natural α-amino acid.

In certain embodiments, the invention relates to any one of the aforementioned peptides, wherein the second amino acid is a non-natural α-amino acid.

In certain embodiments, the invention relates to any one of the aforementioned peptides, wherein the second amino acid is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, or 2,3-diaminopropionic acid (DAP).

In certain embodiments, the invention relates to any one of the aforementioned peptides, wherein the second amino acid is lysine, 2,3-diaminopropionic acid, or glycine.

In certain embodiments, the invention relates to any one of the aforementioned peptides, wherein the detectable moiety is a donor chromophore or an acceptor chromophore.

In certain embodiments, the invention relates to any one of the aforementioned peptides, wherein the detectable moiety is an acceptor chromophore.

In certain embodiments, the invention relates to any one of the aforementioned peptides, wherein the detectable moiety is a phosphorescent moiety or a fluorescent moiety.

In certain embodiments, the invention relates to any one of the aforementioned peptides, wherein the detectable moiety is a fluorescent moiety.

In certain embodiments, the invention relates to any one of the aforementioned peptides, wherein the detectable moiety is dansyl, umbelliferone, coumarin, pyran, cyanine, croconium, squarylium, oxobenzanthracene, fluorescein, rhodamine, pyrylium, perylene, stilbene, or polythiophene, or a derivative of dansyl, umbelliferone, coumarin, pyran, cyanine, croconium, squarylium, oxobenzanthracene, fluorescein, rhodamine, pyrylium, perylene, stilbene, or polythiophene.

In certain embodiments, the invention relates to any one of the aforementioned peptides, wherein the detectable moiety is coumarin or a coumarin derivative.

In certain embodiments, the invention relates to any one of the aforementioned peptides, wherein the detectable moiety is rhodamine or a rhodamine derivative.

In certain embodiments, the invention relates to any one of the aforementioned peptides, wherein the detectable moiety is benzimidazole, imidazopyridine, pyridine, pyrimidine, or triazine, or a derivative of benzimidazole, imidazopyridine, pyridine, pyrimidine, or triazine.

In certain embodiments, the invention relates to any one of the aforementioned peptides, wherein the detectable moiety is covalently bonded to the second amino acid via a second linker.

In certain embodiments, the invention relates to any one of the aforementioned peptides, wherein the detectable moiety is covalently bonded to the side chain of the second amino acid via a second linker.

wherein the second linker is an amide bond, a disulfide bond, a thioether bond, a thiourea, or a triazole.

In certain embodiments, the invention relates to any one of the aforementioned peptides, wherein the second linker is an amide bond.

In certain embodiments, the invention relates to any one of the aforementioned peptides, wherein the amino acid compound and the second amino acid are separated by PPP.

In certain embodiments, the invention relates to any one of the aforementioned peptides, wherein the peptide comprises the following formula:

sensor moiety-first linker-first amino acid-(Xaa)$_p$-
second amino acid-(Xaa)$_p$      (SEQ ID NO: 13)

wherein, independently for each occurrence,
the sensor moiety is covalently bonded to the N-terminus of the first amino acid via the first linker, or the sensor moiety is covalently bonded to the side chain of the first amino acid via the first linker;
the detectable moiety is covalently bonded to the side chain of the second amino acid via a second linker;
p is 0-10 inclusive; and
Xaa is a natural amino acid or a non-natural amino acid.

In certain embodiments, the invention relates to any one of the aforementioned peptides, wherein Xaa is a natural α-amino acid or a non-natural α-amino acid.

In certain embodiments, the invention relates to any one of the aforementioned peptides, wherein Xaa is a natural α-amino acid.

In certain embodiments, the invention relates to any one of the aforementioned peptides, wherein Xaa is a non-natural α-amino acid.

In certain embodiments, the invention relates to any one of the aforementioned peptides, wherein the peptide comprises the following formula:

detectable moiety-second linker-second amino acid-
(Xaa)$_p$-first amino acid-(Xaa)$_p$      (SEQ ID NO: 14)

wherein, independently for each occurrence,
the detectable moiety is covalently bonded to the N-terminus of the second amino acid via the second linker, or the detectable moiety is covalently bonded to the side chain of the second amino acid via the second linker;
the sensor moiety is covalently bonded to the side chain of the first amino acid via the first linker;
p is 0-10 inclusive; and
Xaa is a natural amino acid or a non-natural amino acid.

In certain embodiments, the invention relates to any one of the aforementioned peptides, wherein Xaa is a natural α-amino acid or a non-natural α-amino acid.

In certain embodiments, the invention relates to any one of the aforementioned peptides, wherein Xaa is a natural α-amino acid.

In certain embodiments, the invention relates to any one of the aforementioned peptides, wherein Xaa is a non-natural α-amino acid.

In certain embodiments, the invention relates to any one of the aforementioned peptides, wherein the peptide comprises the following formula:

(Xaa)$_p$-first amino acid-(Xaa)$_p$-second amino acid-
(Xaa)$_p$      (SEQ ID NO: 15)

Or (Xaa)$_p$-second amino acid-(Xaa)$_p$-first amino acid-
(Xaa)$_p$      (SEQ ID NO: 16)

wherein, independently for each occurrence,
the sensor moiety is covalently bonded to the side chain of the first amino acid via the first linker;
the detectable moiety is covalently bonded to the side chain of the second amino acid via a second linker;
p is 0-10 inclusive; and
Xaa is a natural amino acid or a non-natural amino acid.

In certain embodiments, the invention relates to any one of the aforementioned peptides, wherein Xaa is a natural α-amino acid or a non-natural α-amino acid.

In certain embodiments, the invention relates to any one of the aforementioned peptides, wherein Xaa is a natural α-amino acid.

In certain embodiments, the invention relates to any one of the aforementioned peptides, wherein Xaa is a non-natural α-amino acid.

In certain embodiments, the invention relates to any one of the aforementioned peptides, wherein the peptide comprises the following formula:

sensor moiety-first linker-first amino acid-PPP-second
amino acid-Xaa      (SEQ ID NO: 17)

wherein
the sensor moiety is the first linker is an amide;
the first amino acid is glycine;
the second amino acid is lysine;

the detectable moiety is covalently bonded to the side chain of the second amino acid via a second linker;
the detectable moiety is a coumarin derivative;
the second linker is an amide; and
Xaa is a natural amino acid or a non-natural amino acid.

In certain embodiments, the invention relates to any one of the aforementioned peptides, wherein Xaa is a natural α-amino acid or a non-natural α-amino acid.

In certain embodiments, the invention relates to any one of the aforementioned peptides, wherein Xaa is a natural α-amino acid.

In certain embodiments, the invention relates to any one of the aforementioned peptides, wherein Xaa is a non-natural α-amino acid.

In certain embodiments, the invention relates to any one of the aforementioned peptides, wherein the peptide comprises the following formula:

sensor moiety-first linker-first amino acid-PPP-second amino acid-DDD        (SEQ ID NO: 18)

wherein
the sensor moiety is

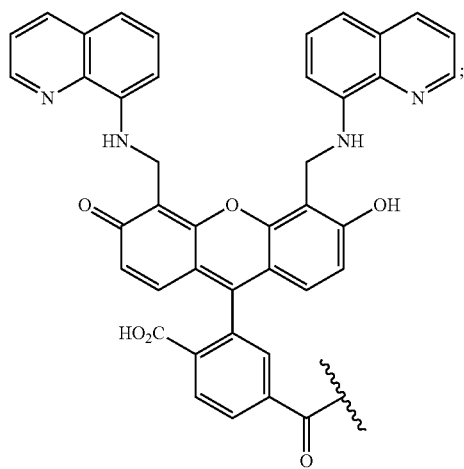 [SMILES: *C(=O)c1ccc(C(=O)O)c(-c2c3ccc(=O)c(CNc4cccc5cccnc45)c-3oc3c(CNc4cccc5cccnc45)c(O)ccc23)c1]

the first linker is an amide;
the first amino acid is 2,3-diaminopropionic acid;
the second amino acid is lysine;
the detectable moiety is covalently bonded to the side chain of the second amino acid via a second linker;
the detectable moiety is a coumarin derivative; and
the second linker is an amide.

In certain embodiments (SEQ ID NOS 19-23), the invention relates to any one of the aforementioned peptides, wherein Xaa is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, or 2,3-diaminopropionic acid (DAP).

In certain embodiments, the invention relates to any one of the aforementioned peptides, wherein the peptide further comprises a sequence selected from the group consisting of KALAKALAKALA (SEQ ID NO: 1), RQIKIWFQNR-RMKWKK (SEQ ID NO: 2), GRKKRRQRRRPQ (SEQ ID NO: 3), DDD, SDYQRL (SEQ ID NO: 4), KDEL (SEQ ID NO: 5), KGEGAAVLLPVLLAAPG (SEQ ID NO: 6), (D-Arg)-cyclohexylalanine-(D-Arg)-cyclohexylalanine-(D-Arg), and PPPDD (SEQ ID NO: 7).

In certain embodiments, the invention relates to any one of the aforementioned peptides, wherein the peptide further comprises a sequence selected from the group consisting of KALAKALAKALA (SEQ ID NO: 1), RQIKIWFQNR-RMKWKK (SEQ ID NO: 2), GRKKRRQRRRPQ (SEQ ID NO: 3), DDD, SDYQRL (SEQ ID NO: 4), KDEL (SEQ ID NO: 5), and KGEGAAVLLPVLLAAPG (SEQ ID NO: 6); and the sequence is covalently bonded to the N-terminus of the peptide or the C-terminus of the peptide.

In certain embodiments, the invention relates to any one of the aforementioned peptides, wherein the peptide further comprises a sequence selected from the group consisting of KALAKALAKALA (SEQ ID NO: 1), RQIKIWFQNR-RMKWKK (SEQ ID NO: 2), DDD, SDYQRL (SEQ ID NO: 4), KDEL (SEQ ID NO: 5), and KGEGAAVLLPVLLAAPG (SEQ ID NO: 6); and said sequence is covalently bonded to the N-terminus of the peptide.

In certain embodiments, the invention relates to any one of the aforementioned peptides, wherein the peptide further comprises a sequence selected from the group consisting of GRKKRRQRRRPQ (SEQ ID NO: 3) and DDD; and said sequence is covalently bonded to the C-terminus of the peptide.

In certain embodiments, the invention relates to any one of the aforementioned peptides, wherein the peptide further comprises a sequence selected from the group consisting of KALAKALAKALA (SEQ ID NO: 1), RQIKIWFQNR-RMKWKK (SEQ ID NO: 2), DDD, SDYQRL (SEQ ID NO: 4), KDEL (SEQ ID NO: 5), and KGEGAAVLLPVLLAAPG (SEQ ID NO: 6); and said sequence is covalently bonded to the C-terminus of the peptide.

In certain embodiments, the invention relates to any one of the aforementioned peptides, wherein the peptide further comprises a sequence selected from the group consisting of GRKKRRQRRRPQ (SEQ ID NO: 3) and DDD; and said sequence is covalently bonded to the N-terminus of the peptide.

Exemplary Methods of Use

In certain embodiments, the invention relates to a method of quantifying an amount of a substance in a cell, comprising the steps of:
contacting the cell with a detectable amount of any one of the aforementioned peptides; and
detecting a signal, wherein the signal emitted by the peptide in the presence of the substance is different than the signal emitted by the peptide in the absence of the substance.

In certain embodiments, the invention relates to a method of quantifying an amount of a substance in a specific locale of a cell, comprising the steps of:
contacting the cell with a detectable amount of any one of the aforementioned peptides; and
detecting a signal from a specific locale of the cell, wherein the signal emitted by the peptide in the presence of the substance is different than the signal emitted by the peptide in the absence of the substance.

In certain embodiments, the invention relates to any one of the aforementioned methods, further comprising the step of:
irradiating the cell in the presence of the peptide at a wavelength for a period of time.

In certain embodiments, the invention relates to any one of the aforementioned methods, further comprising the steps of:
exposing to a first magnetic field the cell in the presence of the peptide for a first period of time; and exposing to an electromagnetic field the cell in the presence of the peptide at a second frequency for a second period of time, wherein the second frequency is a radio frequency.

In certain embodiments, the invention relates to any one of the aforementioned methods, wherein the specific locale in the cell is an intracellular probe, an extracellular probe, a trans-Golgi network, a mitochondrion, or an endoplasmic reticulum.

In certain embodiments, the invention relates to any one of the aforementioned methods, wherein the cell is a HeLa cell, a HEK cell, or a neuron.

In certain embodiments, the invention relates to any one of the aforementioned methods, wherein the signal is detected using ratiometric fluorescence microscopy.

In certain embodiments, the invention relates to a method of quantifying an amount or determining a location of a substance in a subject, comprising the steps of:
    administering to the subject a detectable amount of any one of the aforementioned peptides; and
    detecting a signal, wherein the signal emitted by the peptide in the presence of the substance is different than the signal emitted by the peptide in the absence of the substance.

In certain embodiments, the invention relates to any one of the aforementioned methods, wherein the method is a method of quantifying the amount or determining the location of a substance released from the hippocampus; and the substance is $Zn^{2+}$.

In certain embodiments, the invention relates to any one of the aforementioned methods, wherein the method is a method of quantifying the amount or determining the location of a substance released from the CA3 region of the hippocampus; and the substance is $Zn^{2+}$.

In certain embodiments, the invention relates to any one of the aforementioned methods, wherein the method is a method of quantifying the amount or determining the location of a substance released from presynaptic mossy fibers (mf) in the CA3 region of the hippocampus; and the substance is $Zn^{2+}$.

In certain embodiments, the invention relates to any one of the aforementioned methods, wherein the location of the substance is the synaptic cleft.

In certain embodiments, the invention relates to any one of the aforementioned methods, wherein the location of the substance is the intracellular space of the hippocampus.

In certain embodiments, the invention relates to any one of the aforementioned methods, wherein the location of the substance is in mossy fiber buttons of the hippocampus.

In certain embodiments, the invention relates to any one of the aforementioned methods, wherein the location of the substance is the pancreas.

In certain embodiments, the invention relates to any one of the aforementioned methods, wherein the location of the substance is the prostate.

In certain embodiments, the invention relates to any one of the aforementioned methods, wherein the location of the substance is the prostatic fluid.

In certain embodiments, the invention relates to any one of the aforementioned methods, wherein the subject is a mammal.

In certain embodiments, the invention relates to any one of the aforementioned methods, wherein the subject is a mouse or a rat.

In certain embodiments, the invention relates to any one of the aforementioned methods, wherein the signal is fluorescence, phosphorescence, or a radio frequency (via magnetic resonance imaging, or MRI).

In certain embodiments, the invention relates to any one of the aforementioned methods, wherein the signal is fluorescence.

In certain embodiments, the invention relates to any one of the aforementioned methods, wherein the signal is detected using ratiometric fluorescence microscopy.

In certain embodiments, the invention relates to any one of the aforementioned methods, wherein the substance is selected from the group consisting of $Zn^{2+}$, nitric oxide, $Ca^{2+}$, $Cu^+$, $Cu^{2+}$. $H^+$, hydrogen peroxide, hydrogen sulfide, and reactive oxygen species (ROS).

In certain embodiments, the invention relates to any one of the aforementioned methods, wherein the substance is $Zn^{2+}$.

EXEMPLIFICATION

The invention now being generally described, it will be more readily understood by reference to the following examples, which are included merely for purposes of illustration of certain aspects and embodiments of the invention, and are not intended to limit the invention.

Example 1

Development of ZRPs

Figure 3:
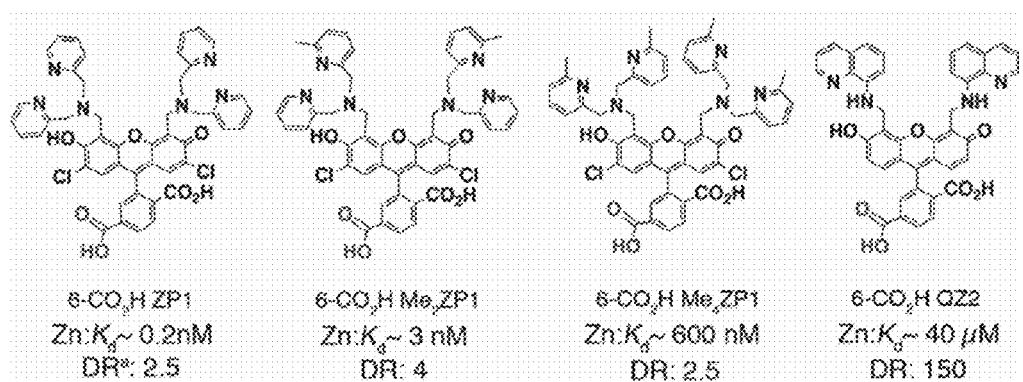
FIG. 3 depicts line drawings for representative 6-$CO_2H$ ZP sensors. $^a$DR is the dynamic range, or the increase in brightness (•×ε), that results from Zn(II) coordination.

Development of ZRPs requires the site-specific incorporation of zinc binding units, such as those in the well-established ZP and QZ families of zinc sensors. ZP and QZ sensors were chosen because they afford a library of molecules with varying zinc affinities and photophysical properties. Nolan, E. M.; Lippard, S. J. *Acc Chem Res* 2009, 42, 193. The 5- or 6-carboxy derivatives of the ZP and QZ sensors can be readily synthesized in high yields using established protocols, providing a convenient route for sensor incorporation (FIG. 3). To date, 6-$CO_2H$ ZP1 has been integrated into a peptide scaffold through three parallel approaches: (i) independent synthesis of an FMOC protected zinc responsive amino acid (ZR-AA) that features ZP1 as a zinc-responsive sidechain; (ii) incorporation of the ZP group onto the N-terminus of the peptide backbone; and (iii) coupling the ZP group to the primary amine sidechain of a lysine residue after selective deprotection of the 8-amino protecting group on the resin.

Approach (i)

Figure 4:
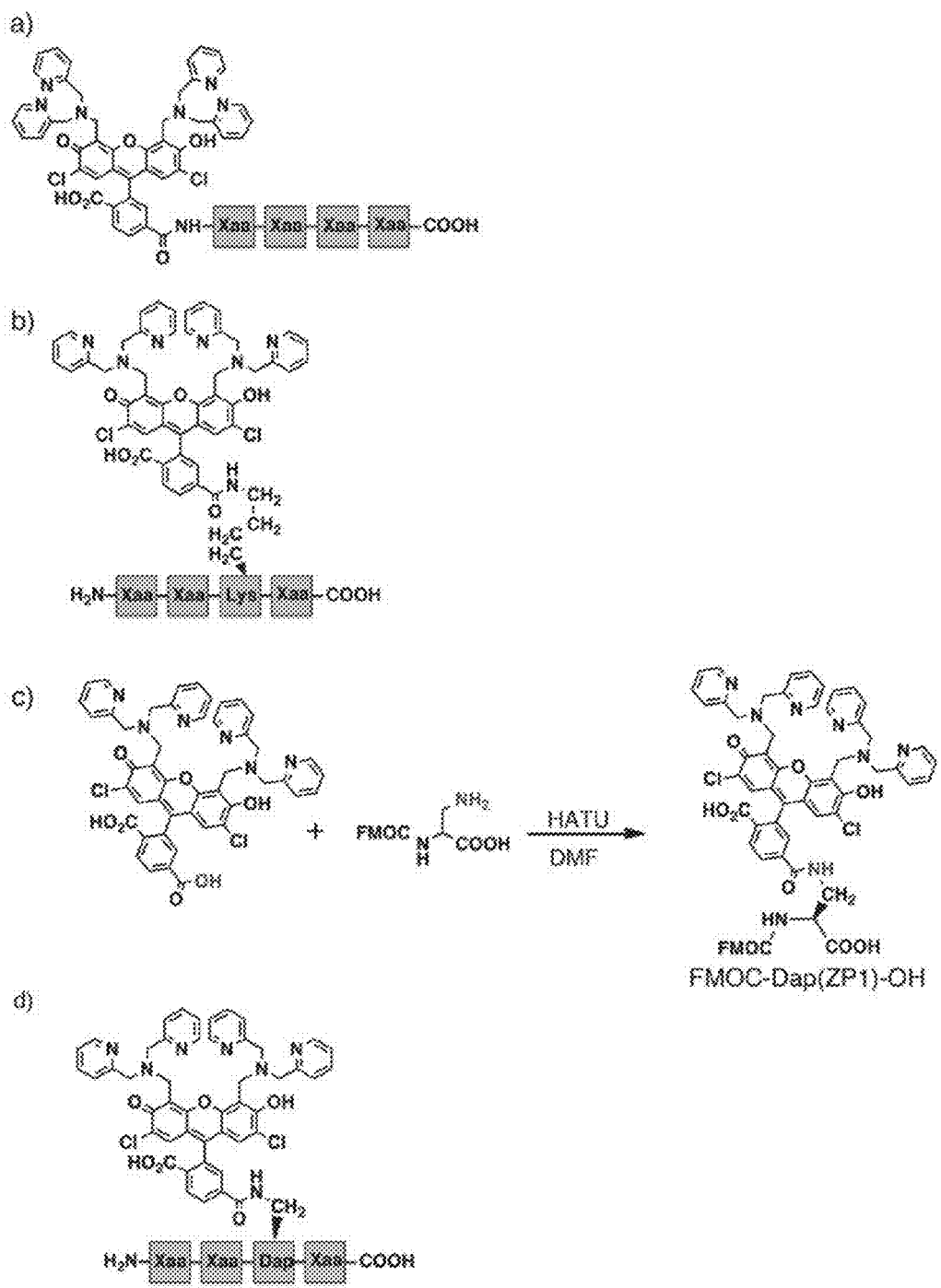
FIG. 4 depicts schematics detailing different avenues by which members of the ZP family of zinc sensors can be incorporated into peptide scaffolds. Methodologies include coupling (6-COOH)ZP1 to (a) the N-terminus of a peptide or (b) a nucleophilic side-chain, such as the primary amine of a lysine residue. Additionally, a non-natural amino acid derivative of the ZP sensor (c) can be independently synthesized, allowing for facile incorporation of the zinc sensors during solid phase peptide synthesis (d).
Figure 5:
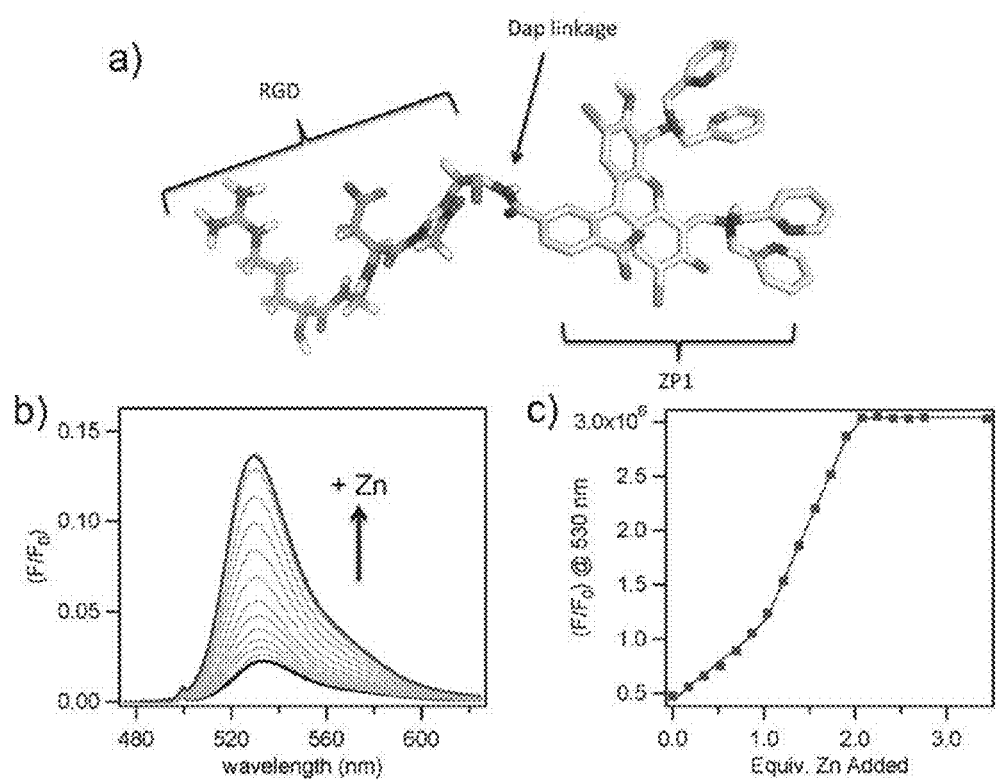
FIG. 5 depicts (a) a computer model of ZRP-1, which features the ZR-AA, Dap(ZP1), at the C-terminus of a short model peptide; (b) the change in the fluorescence spectrum of ZRP-1 with increasing $Zn^{2+}$ concentration; and (c) the binding isotherm for ZRP-1 plotted as a function of equivalents of $Zn^{2+}$ ions added.

The ZR-AA, FMOC-Dap(ZP1)-OH was prepared in good yields (75%) by coupling 6-$CO_2H$ ZP1 to the primary amine sidechain of the amino acid analog, N-alpha-(9-fluorenylmethyloxycarbonyl)-L-2,3-diaminopropionic acid, FMOC-Dap-OH, using standard peptide coupling reagents (FIG. 4). The identity of FMOC-Dap(ZP1)-OH was confirmed by ESI-MS and $^1$H-NMR spectroscopy. FMOC-Dap(ZP1)-OH was subsequently incorporated into a short model peptide (ZRP-1) using standard SPPS methodologies. ZRP-1 was readily purified (>99.5%) by HPLC and identified with ESI-MS. Spectroscopic characterization of the peptide revealed that the ZRP-1 has photophysical and zinc binding properties analogous to those of the parent 6-$CO_2H$ ZP1 sensor (FIG. 5 and FIG. 6a), with a dynamic range (DR) of ~7.5 and a $K_{d-Zn}$<1 nM.

Approach (ii)

Figure 6:
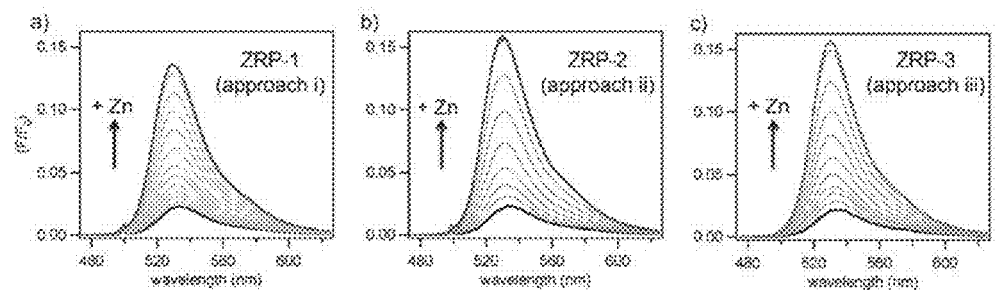
FIG. 6 depicts the observed changes in the normalized fluorescence spectra of ZRP-1 (a), ZRP-2 (b), and ZRP-3 (c) upon the addition of increasing amount of zinc.

As an alternative method to synthesizing ZR-AAs, 6-$CO_2H$ ZP1 was coupled directly to the reactive N-terminus of the peptide backbone. The 5- or 6-carboxy group on the benzoate ring of the fluorescein platform reacts specifically with the N-terminus of peptide scaffolds, providing a convenient route for direct incorporation of fluorescent probes. As a proof-of-concept, 6-$CO_2H$ ZP1 was incorporated into another short model peptide, ZRP-2. As in approach (i), the conditions required for peptide synthesis and isolation of ZRP-2 have a negligible effect on both the photophysics and the zinc binding properties of the ZP sensor (FIG. 6b).

Approach (iii)

The third route employed to introduce 6-$CO_2H$ ZP1 into a model peptide required the selective deprotection of a lysine residue during the solid phase synthesis. FMOC-Lys(4-methyltrityl, MTT)-OH is a commercially available amino acid that utilizes the 4-methyltrityl moiety as the protecting group for the lysine primary amine sidechain. The MTT group is readily cleaved in a mildly acidic solution (1% Trifluoroacetic acid in dichloromethane) allowing for selective deprotection of the nucleophilic ε-amino functional group. Using this chemistry, 6-$CO_2H$ ZP1 was coupled to the lysine sidechain of a short model peptide, ZRP-3. As for compounds obtained by methods (i) and (ii), ZRP-3 displays a responsiveness to $Zn^{2+}$ ions that is analogous to that of the parent ZP sensor (FIG. 6c).

Example 2

Engineering a Ratiometric ZRP for the Quantification of mZn

Ratiometric zinc probes provide the distinct advantage of being able to quantify mZn concentration independent of sensor concentration. The modular nature of the peptide scaffold readily allows ZRPs to be rendered ratiometric by incorporating a FRET donor or acceptor together with the ZR-AA. Since both the ZP and QZ derivatives are based on a fluorescein platform, molecules known to be donor or acceptor partners with fluorescein will similarly be introduced into the peptide scaffold. Coumarin-343 (C343), an energy donor to fluorescein, and 5(6)-carboxytetramethylrhodamine (5(6)-TAMRA), an energy acceptor from fluorescein, both feature a reactive carboxylic acid group and can be incorporated into a peptide framework using methodologies similar to those applied in Example 1. Both C343 and 5(6)-TAMRA are commercially available or can readily be prepared on the gram scale using known literature procedures. Initial studies will be conducted utilizing a polyproline (PP) helix as the peptide scaffold. PP peptides have a rigid secondary structure, mandated by their dihedral angles, which form a left-handed helix with a rise of ~3.1 Å per residue and pseudo-three fold symmetry. PP peptides have long been considered "molecular rulers," and were used by Stryer and Haugland in the first demonstration of energy transfer over 50 years ago. Stryer, L.; Haugland, R. P. *Proc Natl Acad Sci USA* 1967, 58, 719.

Figure 7:
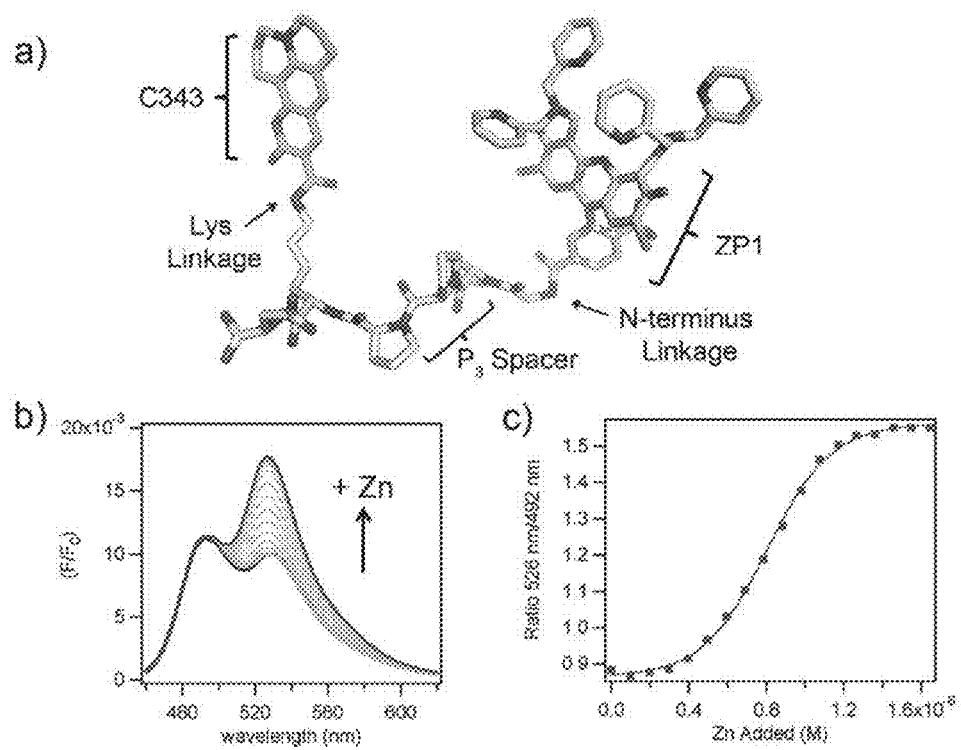
FIG. 7 depicts (a) a computer model of ratio-ZRP-1, which features a coumarin derivative (C343) coupled to a lysine residue and ZP1 linked to the N-terminus of the peptide; (b) the change in the normalized fluorescence spectrum of ratio-ZRP-1 upon addition of $Zn^{2+}$; and (c) the binding isotherm for ratio-ZRP-1 plotting the change in the (526 nm:492 nm) ratio as a function of the molar concentration of added zinc.
Figure 10:
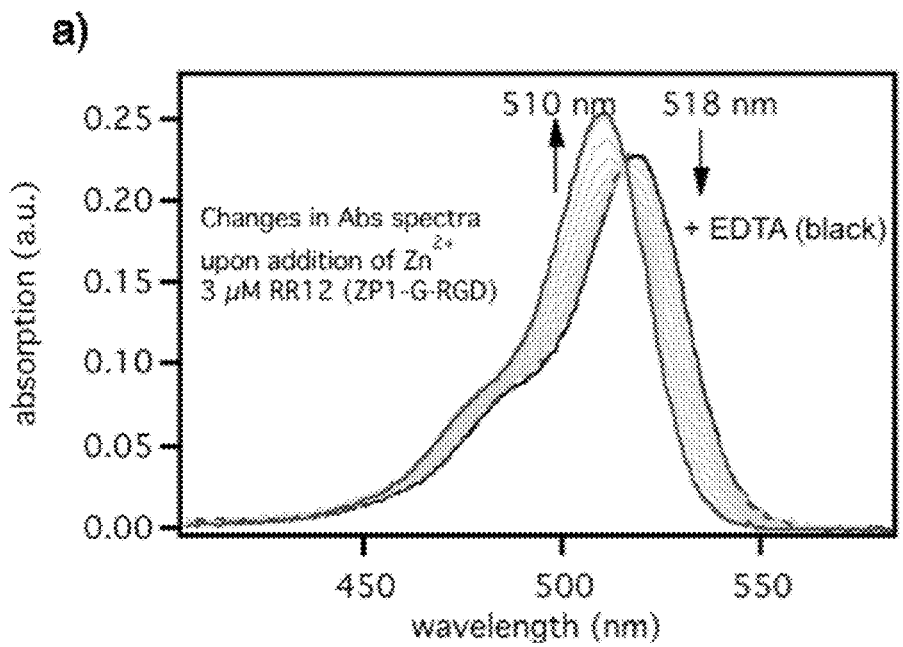
FIG. 10 depicts changes in the UV-visible spectrum of a representative ZRP (ZP1-G-RGD) upon addition of $ZnCl_2$.
Figure 11:
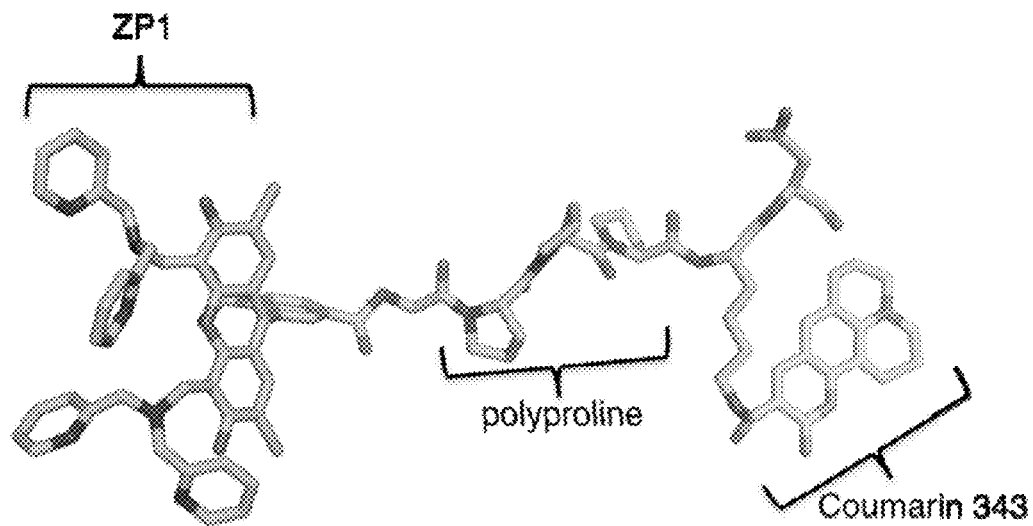
FIG. 11 depicts a computer model of the coumarin 343/ZP1 ratiometric ZRP, ratio-ZRP-1.
Figure 12:
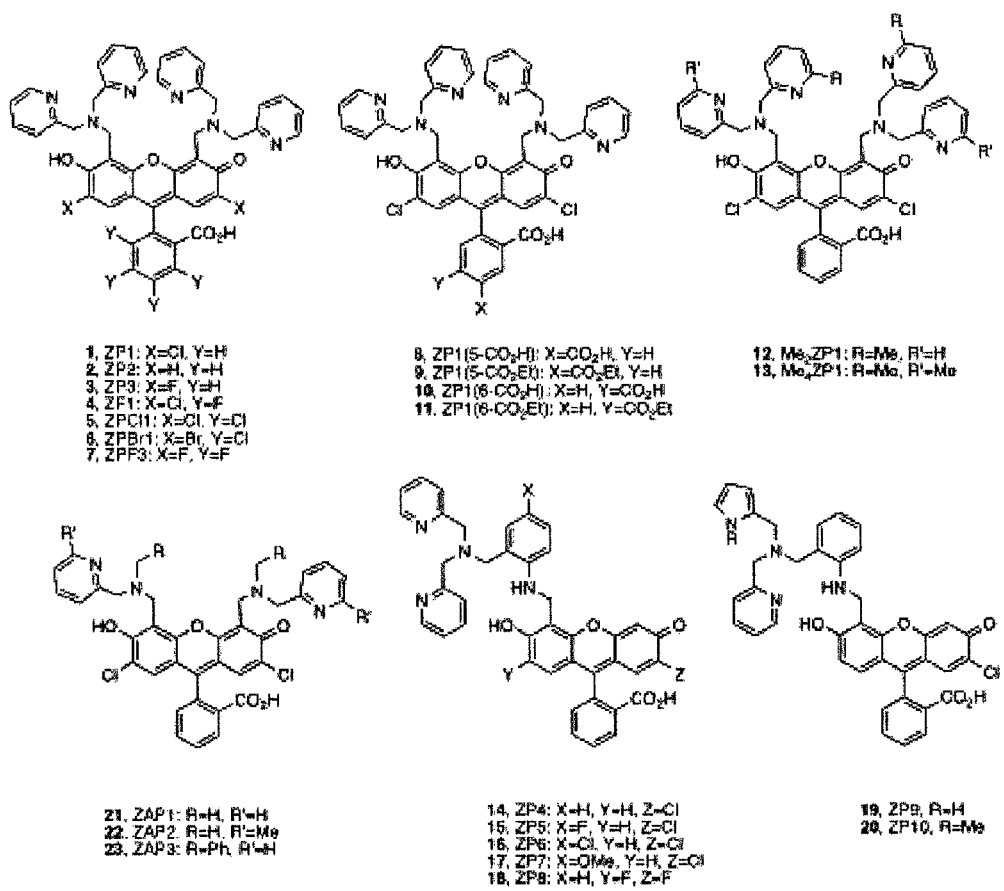
FIG. 12 depicts various fluorescein-based sensors that may be incorporated into the amino acid compounds and peptides of the invention.
Figure 13:
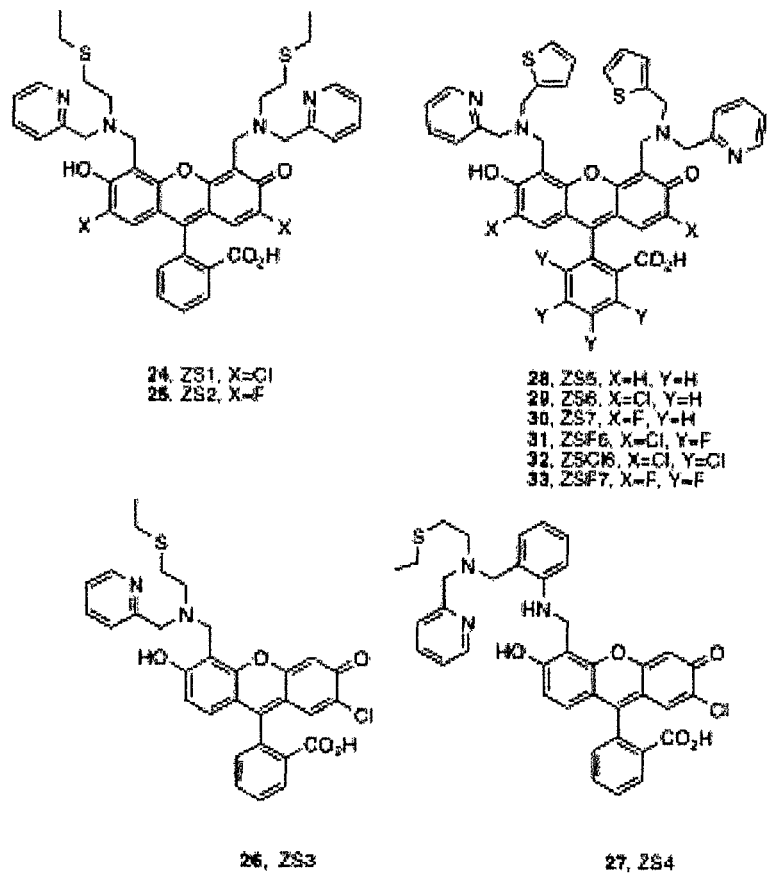
FIG. 13 depicts various fluorescein-based sensors that may be incorporated into the amino acid compounds and peptides of the invention.
Figure 14:
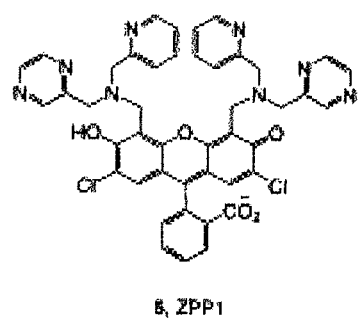
FIG. 14 depicts a fluorescein-based sensor that may be incorporated into the amino acid compounds and peptides of the invention.

A ratiometric ZRP, ratio-ZRP-1, was prepared. It features both C343 and ZP1 in a short (6 residue) peptide. The C343 fluorophore was site-specifically conjugated to a lysine sidechain (Example 1, approach (iii)) near the C-terminus of the peptide, while the 6-$CO_2H$ ZP1 was coupled to the N-terminus of a glycine residue (Example 1, approach (ii)). Ratio-ZRP-1 features a short 3-residue (~9.8 Å) rigid PP spacer that separates the two fluorophores (FIG. 7a). Ratio-ZRP-1 was readily synthesized on the 100 mg scale and determined to be >99.5% pure as judged by analytical HPLC and ESI mass spectroscopy. Initial spectroscopic characterization revealed that ratio-ZRP-1 displays a ratiometric turn-on in the presence on $Zn^{2+}$ (FIG. 7). Studies to evaluate the photophysical and biological properties of ratio-ZRP-1 are currently underway.

As an alternative, if PP peptides prove to be problematic, peptides with alternative secondary structures, primarily peptides with α-helical or β-sheet configurations will be examined. For examples, see Scholtz, J. M. et al. *Annu Rev Biophys Biomol Struct* 1992, 21, 95; Lacroix, E. et al. *Curr Opin Struct Biol* 1999, 9, 487.

Example 3

Creating and Evaluating a Family of ZRPs Capable of Targeting and Quantifying mZn in Specific Cellular Locales (Prophetic)

To achieve precision in subcellular and extracellular localization, short amino acid sequences with known targeting capabilities will be incorporated into ZRPs. Intensive investigation into the discovery and characterization of short (<30 AAs) targeting sequences has resulted in a library of peptides with the capability to specifically deliver payloads both inter- and extra-cellularly. Martin, M. E. et al. *AAPS J* 2007, 9, E18; Pap, E. H. et al. *Exp Cell Res* 2001, 265, 288. These targeting sequences can be used in conjunction with cell penetrating sequences to create a ZRP that both readily cross the cell membrane and target ZRPs to specific subcellular organelles. A potential hazard of this approach is the high variability in the efficacy of a single cell penetrating sequence in differing cell types. Therefore, a small library of cell penetrating sequences (FIG. 9) will be used and their efficacy tested in cell lines that most closely mimic neuronal cell slices (e.g., HEK cells). Penetrating sequences were chosen based on their ability to delivery small-molecule cargoes via a non-endosomal pathway. Varkouhi, A. K. et al. *J Control Release* 2011, 151, 220. Sample targeting sequences for organelles implicated in mZn biochemistry are similarly illustrated in FIG. 9. Because of the water solubility of ZRPs, no organic solvents, such as dimethyl sulfoxide (DMSO), will be used. Recent reports have implicated DMSO as a possible membrane-permeabilizing agent, leading to apparent discrepancies in the cell permeability of small molecule sensors. ZRPs will be synthesized based on the given sequences (Table 1) with the cell penetrating sequence appended to the C-terminus of the ZRP and the organelle targeting domain on the N-terminus. Purity and characterization of ZRPs will be carried out using analytical HPLC and mass spectroscopy. In addition, the zinc binding and fluorescent properties of ZRPs will be characterized using fluorescence and UV-visible spectroscopy. The cellular distribution patterns of ZRPs will be tested primarily in HEK and HeLa cell lines using fluorescence microscopy.

Example 4

Use of ZRPs to Quantify the Amount and Destination of mZn Released from Presynaptic Mossy Fibers in the CA3 Region of the Hippocampus The use of zinc-responsive probes in cell cultures and live hippocampal slices has greatly advanced our understanding of zinc metalloneurochemistry. Pluth, M. D. et al. *Annu Rev Biochem* 2011, 80, 333. Recent issues regarding the cellular distribution of these probes, as well as a more intricate proposal for presynaptic mf zinc, requires a new class of sensors with better chemical, photophysical, and biological properties. Kay, A. R. *Trends Neurosci* 2006, 29, 200; Kay, A. R.; Toth, K. *J Neurophysiol* 2006, 95, 1949. The ZRPs described herein attempt to address these concerns by combining the chemical and physical characteristics of SM probes with the biological localization capabilities of targeting peptide sequences. In particular, a portion of presynaptic mf zinc "re-enters" the presynaptic terminal after release into the extracellular space. Pan, E. et al. *Neuron* 2011, 71, 1116. As a follow-up to this study, the time-dependence of zinc in the synaptic cleft will be investigated; it should first increase and then diminish as the zinc re-enters the presynaptic termini. To approach the problem, a ratiometric ZRP, ratio-ZRP-2, will be used (FIG. 8). This peptide was designed with three Asp residues at the C-terminus, resulting in a peptide that is predicted to stay in the extracellular space as a result of its overall (3-) charge. For ratio-ZRP-2, the QZ2 sensor will be utilized because it has a zinc affinity (~40 µM) that matches closely the estimated concentration of zinc released from glutamatergic vesicles (~100 µM). In addition, the kinetic parameters of QZ2 provide reversibility that should enable a direct visualization of zinc entering and leaving the extracellular space. Nolan, E. M. et al. *J. J Am Chem Soc* 2005, 127, 16812. The addition of C343 to the lysine residue near the C-terminus will enable us to quantify ratiometrically the released zinc based on its energy transfer to QZ2, as well to verify independently probe location. The cell-impermeable chelator ZX1 will be used to verify that the visualized zinc is in the extracellular space. Initially, the ability of ratio-ZRP-2 to quantify mZn will be investigated in dissociated cultures and organotypic slices from mouse and rat hippocampus. Direct time-dependent investigation of mZn during mf-LTP will be executed.

Example 5

Palm-ZP1 and the Extracellular Matrix

Zinc release is essential for the physiology of specialized secretory tissues. Investigating the mechanism of zinc-release, however, is challenging in part due to the difficulty of directing a zinc-binding probe specifically to the plasma membrane. To date, there are only two zinc sensors that localize here, both of which require complex, multi-step syntheses. For such targeting, we prepared a short peptide consisting of an N-terminal palmitoyl group, a 3-residue (~9.8 Å) polyproline helix, two sequential Asp residues, and a C-terminal Lys to serve as the point of attachment for the 6-$CO_2H$ ZP1 moiety (hereafter referred to as ZP1, FIG. 15*a*). Based on a modified fluorescein core, the ZP family has binding affinities that span 5 orders-of-magnitude, a well-documented record of zinc-induced turn-on in cells, and members that have carboxylates at the 5- or 6-position of the fluorescein, which make them amenable for peptide coupling.

The components of Palm-ZP1 were designed to work in concert to localize the zinc-sensing unit to the extracellular side of the plasma membrane. The palmitoyl moiety mimics a post-translational modification that directs proteins to the plasma membrane. The polyproline helix provides a rigid spacer, separating ZP1 from surface-bound proteins and biomolecules that might quench the ZP1 fluorescein core. The two sequential Asp residues provide two additional negative charges, which impede diffusion across the lipid bilayer. Finally, the ε-amino group on the Lys residue serves as a point of attachment for the ZP1 moiety.

Palm-ZP1 was manually synthesized on Rink amide AM resin by using standard FMOC coupling chemistry. First, the peptide scaffold was constructed by sequential addition of amino acids using published procedures. Next, palmitic acid was coupled to the N-terminus under analogous conditions. The acid-sensitive 4-methyltrityl (MTT) protecting group was then removed from the ε-amino moiety on the C-terminal Lys, providing a convenient route for "on-resin" incorporation of ZP1. Palm-ZP1 was subsequently cleaved from the resin and purified using standard procedures (see later examples).

Figure 16:
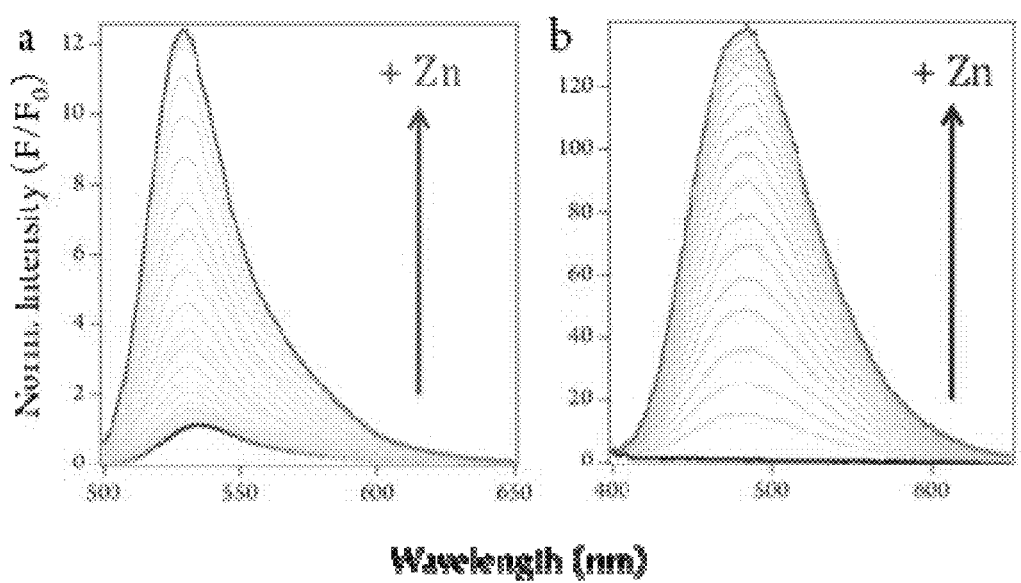
FIG. 16 depicts the observed changes in normalized fluorescence intensity of ~2.5 µM solutions of (a) Palm-ZP1 and (b) ZQ-MPP, in 25 mM PIPES buffer (pH 7) with 50 mM KCl and 50% acetonitrile (v/v), upon addition of $ZnCl_2$.
Figure 24:
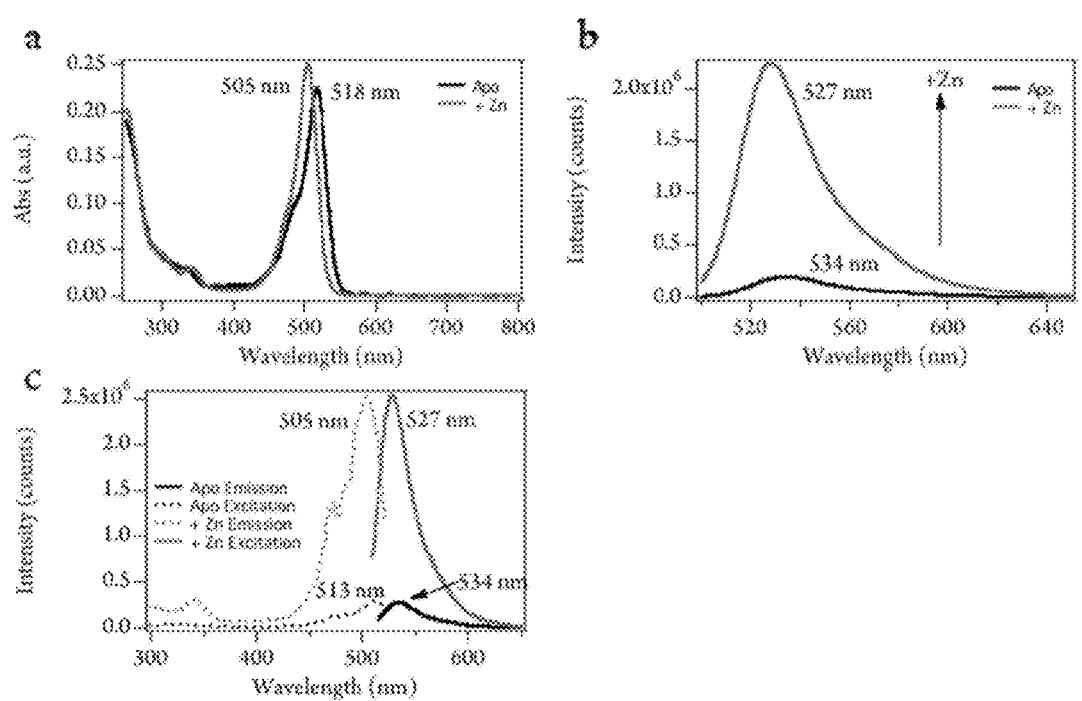
FIG. 24 depicts the results of a photophysical characterization of Palm-ZP1. The absorbance (a) and emission (b) spectra of a 5 μM solution of Palm-ZP1, in 25 mM PIPES (pH 7) with 50 mM KCl, and 50% (v/v) acetonitrile. Spectra were recorded in the presence of EDTA (100 μM) or $ZnCl_2$ (250 μM). The excitation and emission spectra (c) of Palm-ZP1 in the absence (apo) and presence of zinc (+Zn).
Figure 25:
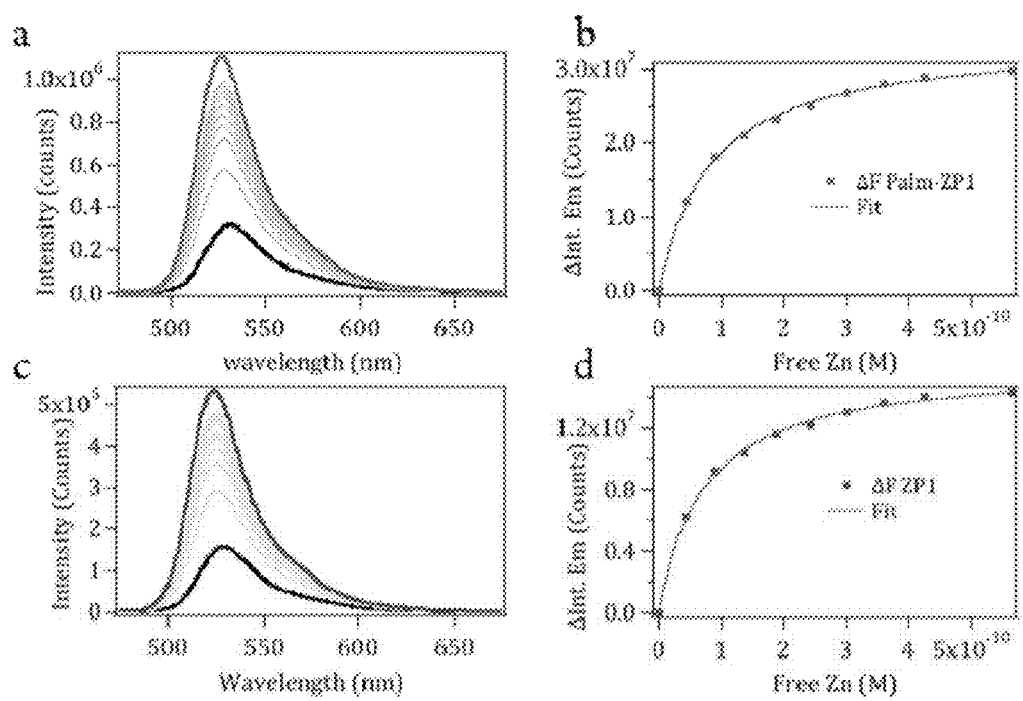
FIG. 25 depicts the results of a measurement of the zinc-binding affinities, by fluorescence spectroscopy, for 2.5 μM solutions of Palm-ZP1 (a) and ZP1 (c), in 25 mM PIPES buffer (pH 7) with 50 mM KCl, and 50% (v/v) acetonitrile. Observed changes in the emission spectra of Palm-ZP1 (a) and ZP1 (c) upon addition of increasing amounts of free zinc. The binding isotherms and fits for (b) Palm-ZP1 and (d) ZP1. Apparent $K_{d-Zn}$ values are given in FIG. 29. Samples were excited at 470 nm with an emission window of 475-675 nm.

To investigate whether the zinc-sensing properties of the ZP1 moiety withstood the conditions of SPPS, we studied the zinc-binding and photophysical properties of Palm-ZP1 in vitro. Due to the hydrophobic palmitoyl moiety, we used a mixed solvent system consisting of 25 mM PIPES buffer (pH 7) with 50 mM KCl and 50% acetonitrile (v/v). In the absence of zinc, Palm-ZP1 has spectral features that are similar to those of other ZP1 derivatives. Apo Palm-ZP1 has a $\lambda_{abs}$=518 nm and $\lambda_{em}$=534 nm ($\phi_{apo}$=0.16±0.05) (FIG. 24 and FIG. 29). Addition of $ZnCl_2$ to a solution of Palm-ZP1 produced a characteristic blue-shift in absorption and emission spectra ($\lambda_{abs}$=505 nm; $\lambda_{em}$=527 nm) and an enhancement of fluorescence ($\phi_{Zn}$=0.79±0.05) (FIG. 16*a*). Measurement of the zinc affinity in a CaEDTA buffered solution indicated that the $K_{d-Zn}$ of Palm-ZP1 closely approximates the $K_{d-Zn}$ of ZP1 (FIG. 25 and FIG. 29).

Figure 28:
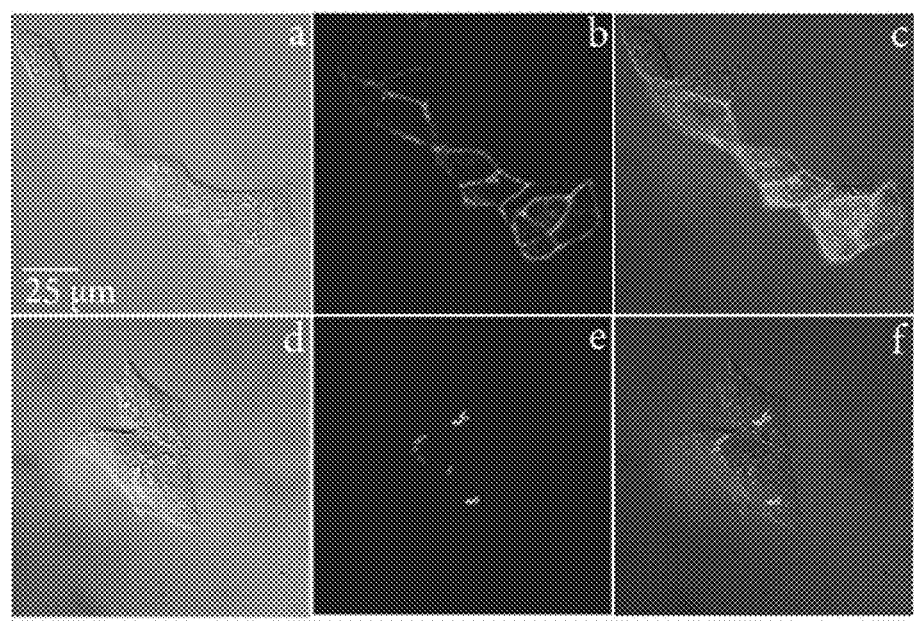
FIG. 28 depicts the observed localization of zinc-bound Palm-ZP1 and ZP1 in live HeLa cells. Top row: (a) DIC image of cells pretreated with a 10 μM solution of Palm-ZP1, (b) emission from zinc-bound Palm-ZP1, (c) overlay of (a) and (b). Bottom row: (d) DIC image of cells pretreated with 5 μM of ZP1 (e) emission from zinc-bound ZP1, (f) overlay of (d) and (e).

To assess the ability of Palm-ZP1 to function within a cellular environment, we conducted live cell imaging experiments. HeLa cells were incubated with a 10 µM solution of Palm-ZP1 in Dulbecco's Modified Eagle Medium (DMEM) for 30 min (37° C., 5% $CO_2$) prior to imaging. Initial cell images had minimal ZP1 emission, consistent with the low quantum yield for the apo form of the sensor. Upon addition of 50 µM $ZnCl_2$, a ~1.7-fold increase in ZP1 fluorescence intensity was observed at the peripheral membrane of the cell, in stark contrast to the localization of ZP1 without the peptide moiety (FIG. 28). It is noteworthy that no exogenous ionophore such as pyrithione was present, suggesting that Palm-ZP1 responds to changes in extracellular zinc concentration. Subsequent addition of 100 µM EDTA, a cell-impermeable chelator, attenuated the fluorescent signal to initial levels within 5 min, further confirming that the zinc-induced fluorescence increase occurs extracellularly.

Figure 17:
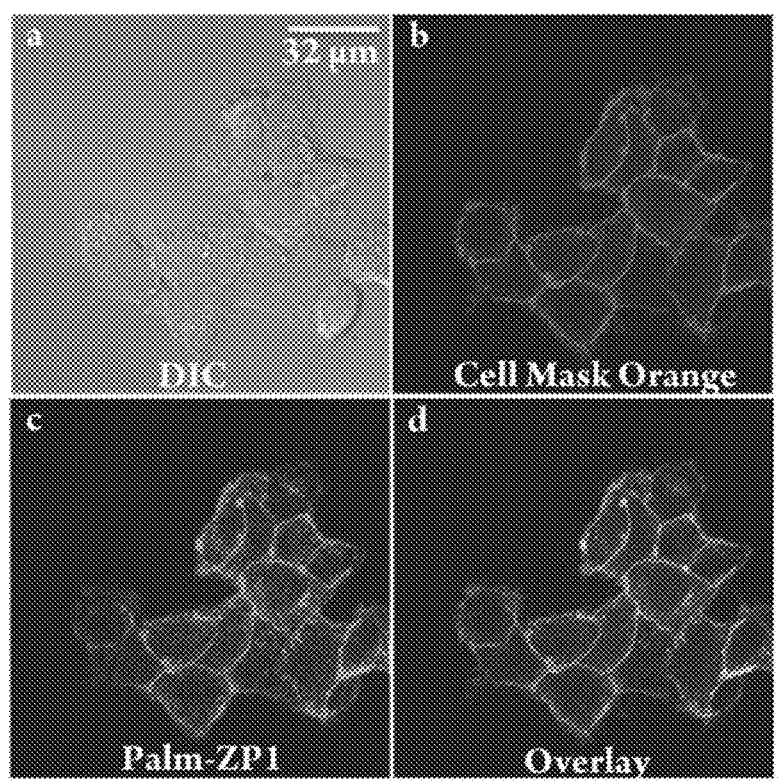
FIG. 17 depicts the results of a localization study of Palm-ZP1 in live HeLa cells. For the image series: (a) differential interference contrast (DIC) image; (b) signal from plasma membrane specific Cell Mask Orange; (c) signal from zinc-bound Palm-ZP1; and (d) an overlay of (b) and (c). Pearson's correlation coefficient r=0.70±0.05

We next explored whether Palm-ZP1 selective accumulates in the plasma membrane. For HeLa cells treated with both Palm-ZP1 and Cell Mask Orange, a commercially available dye specific for the plasma membrane, multichannel fluorescence microscopy qualitatively showed that both dyes preferentially localize to the plasma membrane (FIG. 17). Quantitative image analysis corroborated these findings: Palm-ZP1 and Cell Mask Orange strongly co-localize with a Pearson's correlation coefficient of r=0.70±0.05.

Example 6

ZQ-MPP and Intracellular Sensing

Figure 15:
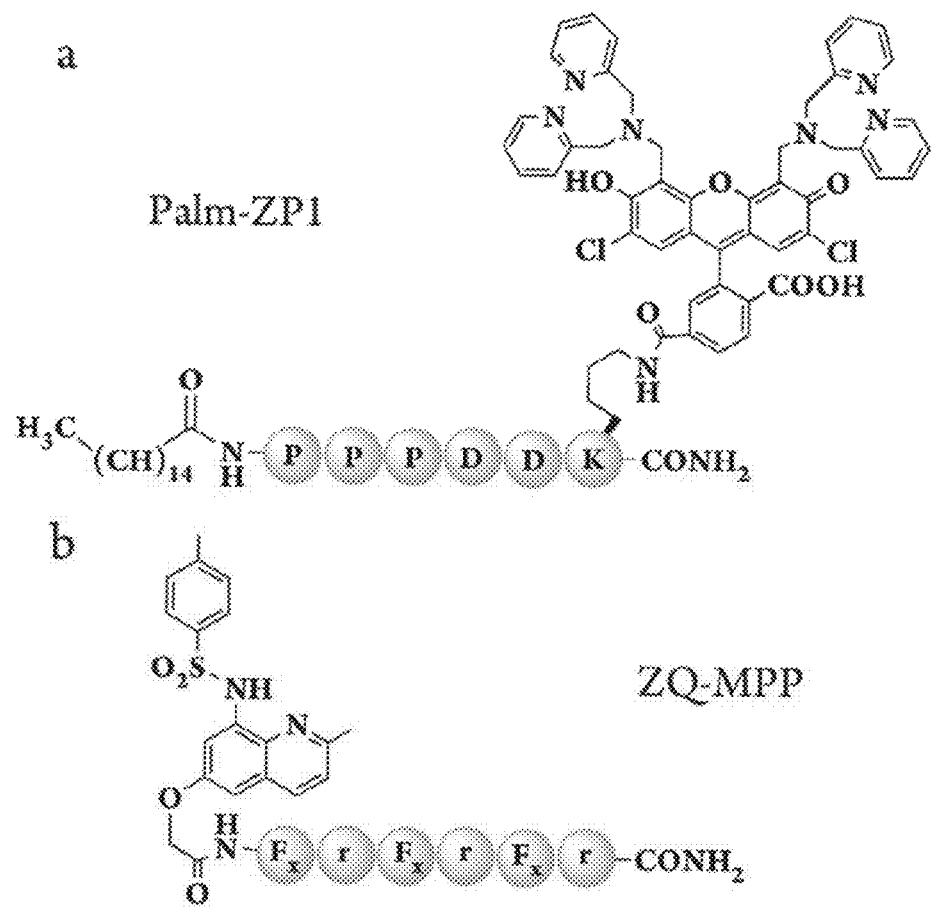
FIG. 15 depicts illustrations of two zinc-sensing peptides, (a) Palm-ZP1 (SEQ ID NO: 8) and (b) ZQ-MPP. $F_x$ and r represent non-natural amino acids cyclohexylalanine and D-Arg, respectively.

Intracellular delivery of a ZSP provides an important benchmark because, to the best of our knowledge, no peptide-based zinc sensor has ever been demonstrated to operate intracellularly. We therefore synthesized ZQ-MPP, which features zinquin appended to the N-terminus of a mitochondria-penetrating peptide (MPP) (FIG. 15*b*). Based on a tosylated quinaldine scaffold, zinquin has known zinc-binding and photophysical properties, and is widely applied in cellular imaging because of its large zinc-specific fluorescence response. Moreover, the free carboxylic acid on the quinaldine moiety provides a convenient synthetic handle for peptide conjugation, and the small hydrophobic nature of zinquin avoids the complications associated with intracellular delivery of peptide-fluorescein derivatives. The tendency of zinquin to compartmentalize within the cell, however, has dampened the enthusiasm for the probe. For an intracellular target, we chose the mitochondrion because zinc levels in this organelle are directly linked with numerous physiological and pathological processes, including serving as a biomarker for the progression of prostate cancer.

Figure 26:
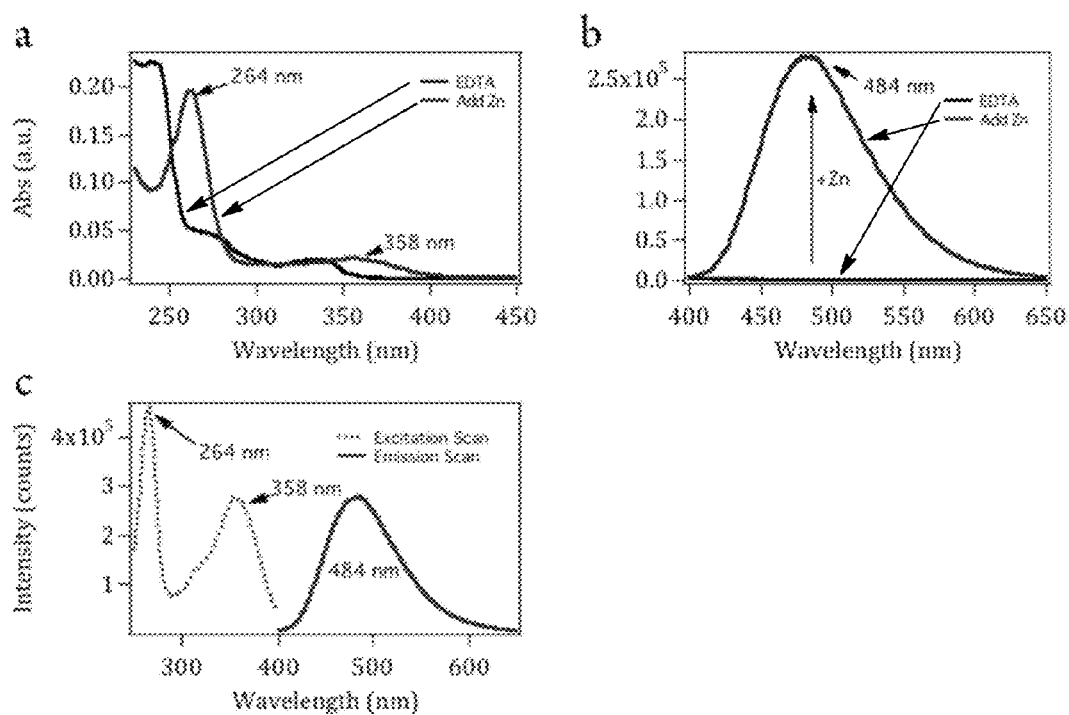
FIG. 26 depicts the results of a photophysical characterization of ZQ-MPP. The absorbance (a) and emission (b) spectra of a 5 μM solution of ZQ-MPP, in 25 mM PIPES (pH 7) with 50 mM KCl, and 50% (v/v) acetonitrile. Spectra were recorded in the presence of EDTA (100 μM) or $ZnCl_2$ (250 μM). The excitation spectra (c) of the zinc-bound ZQ-MPP.
Figure 27:
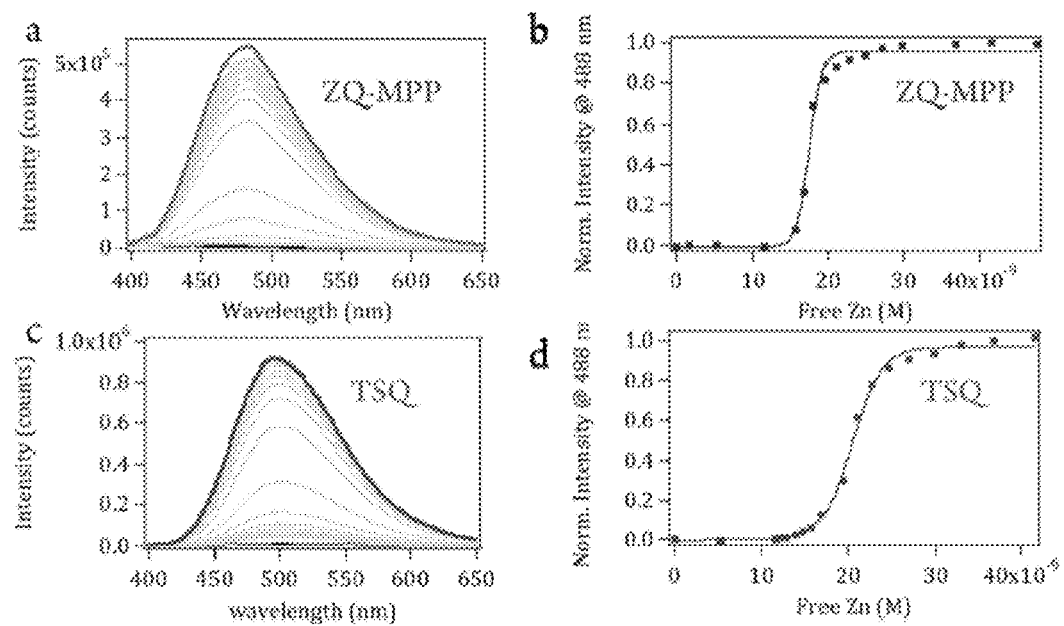
FIG. 27 depicts the results of a measurement of the zinc-binding affinities, by fluorescence spectroscopy, of ZQ-MPP (a) and TSQ (c) in 25 mM PIPES buffer (pH 7) with 50 mM KCl, and 50% (v/v) acetonitrile. Observed changes in the emission spectra of ZQ-MPP (a) and TSQ (c) upon addition of increasing amounts of free zinc. The normalized binding isotherms and corresponding fits for ZQ-MPP (b) and TSQ (d). Calculated apparent $K_{d-Zn}$ values are given in FIG. 30.

ZQ-MPP was prepared manually using standard solid phase methodology. The zinc-binding and photophysical properties of ZQ-MPP are similar to those of zinquin and TSQ (6-methoxy-(8-p-toluenesulfonamido)quinoline) (FIGS. 26, 27 and 30). In the absence of zinc, ZQ-MPP has two main absorption bands with maxima at $\lambda_{abs}$=243 and 336 nm (FIG. 26), and is essentially non-emissive ($\phi \leq 0.002$). Addition of $ZnCl_2$ gives rise to two new features in the absorption spectrum ($\lambda_{abs}$=264 and 358 nm), and a large increase (>100-fold; $\phi$=0.36±0.01) in fluorescence intensity ($\lambda_{em}$=484 nm, FIG. 16b, 26, and Table 30).

Figure 18:
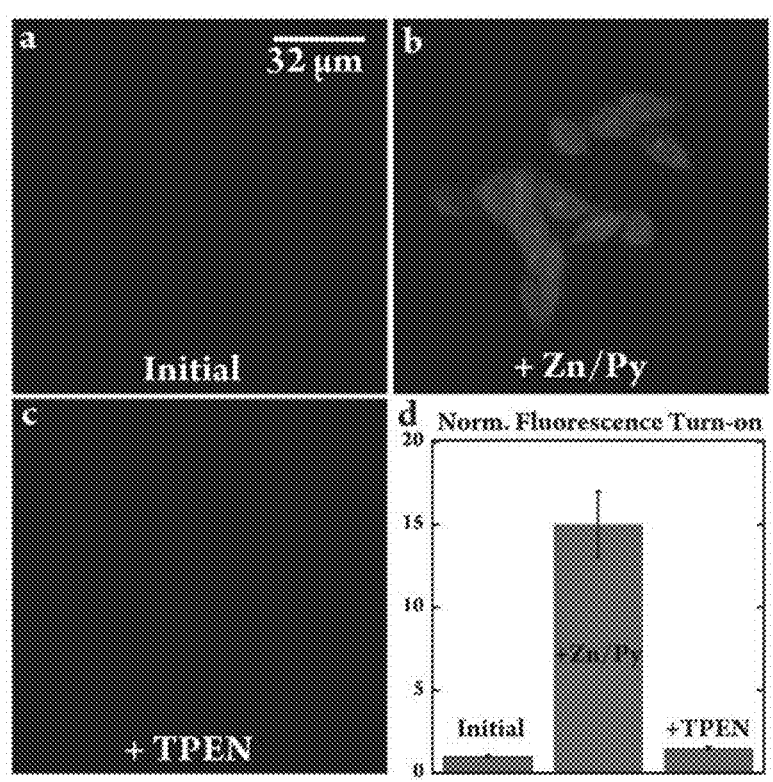
FIG. 18 depicts the change in fluorescence observed for live HeLa cells pretreated with 25 µM of ZQ-MPP. (a) Initial signal intensity. (b) Emission after addition of 50 µM Zn/Py. (c) Signal after addition of 100 µM TPEN. (d) Quantification of the average normalized fluorescence turn-on of ZQ-MPP during live cell imaging. (n=12)
Figure 19:
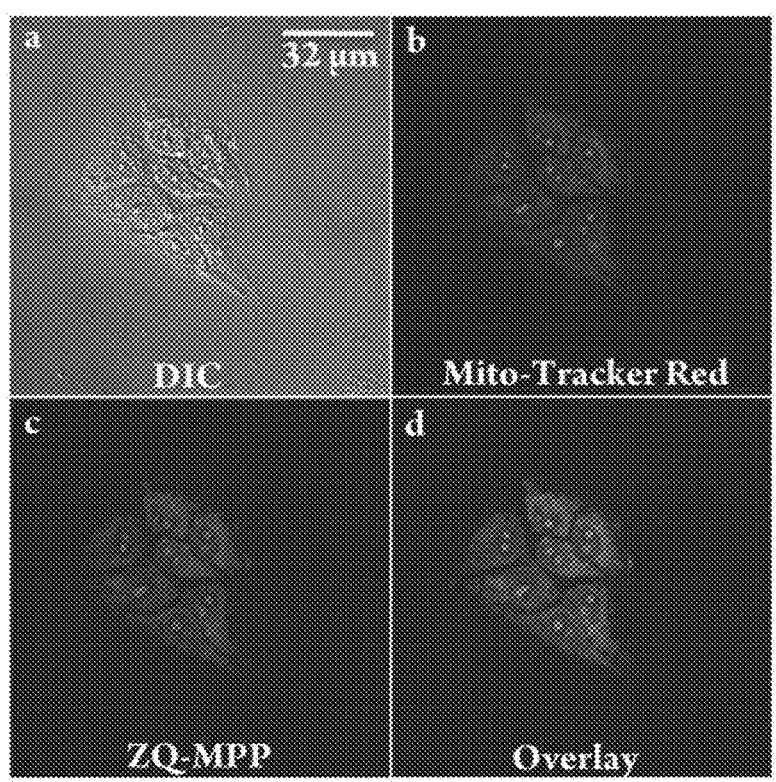
FIG. 19 depicts the results of a localization study of ZQ-MPP in live HeLa cells. For the image series: (a) differential interference contrast (DIC) image; (b) signal from MitoTracker Red; (c) signal from ZQ-MPP; and (d) an overlay of (b) and (c). Pearson's correlation coefficient r=0.71±0.01.

We carried out live cell imaging experiments to determine whether ZQ-MPP could target mitochondria and report on changes in zinc concentrations. HeLa cells were pretreated with a 25 μM solution of ZQ-MPP, which also contained MitoTracker Red as an internal mitochondria tracker (see later examples). Initial fluorescent images showed virtually no signal originating from the ZQ-MPP (FIG. 18a). Addition of 50 μM zinc/pyrithione (Zn/Py), a zinc ionophore, resulted in a ~15-fold increase in ZQ-MPP intensity (FIG. 18b). The signal returned to near baseline levels upon addition of 100 μM TPEN, an intracellular zinc chelator, demonstrating the metal-dependence and reversibility of the emission change (FIG. 18c, d). The localization of ZQ-MPP was investigated with multichannel fluorescence microscopy. Visually, the distribution of MitoTracker Red (FIG. 19b) and ZQ-MPP (FIG. 19c) appear nearly identical. Overlaying the images (FIG. 19d) and calculating the Pearson's correlation coefficient yields an r=0.71±0.01, indicating strong colocalization.

Example 7

General Materials and Methods

HPLC-grade acetonitrile, anhydrous N,N-dimethylformamide (DMF), dichloromethane, 4-methylpiperidine, N,N-diisopropylethylamine (DIPEA), trifluoroacetic acid (TFA), triisopropylsilane, and palmitic acid were purchased from Sigma-Aldrich. FMOC-Pro-OH, FMOC-Asp(OtBu)-OH, and Rink amide AM resin (0.61 mmol/g, 100-200 mesh) were obtained from Novabiochem. FMOC-Lys(MTT)-OH, FMOC-$F_x$-OH (FMOC-Cha-OH), and the D-isomer of FMOC-Arg(Pbf)-OH were purchased from Aapptec. 2-(7-Aza-1H-benzotriazole-1-yl)-1,1,3,3-tetramethyluronium hexafluorophosphate (HATU) was procured from Oakwood Chemicals. N-(6-Methoxy-8-quinolyl)-p-toluenesulfonamide (TSQ) was acquired from Enzo Life Sciences. Disposable 2.5-mL reaction vessels were ordered from Torviq. All solvents were reagent grade unless otherwise specified, and commercially available reagents were used as received. 6-$CO_2$H ZP1 and zinquin acid were prepared according to literature procedures. Woodroofe, C. C.; et al. Chem. Biol. 2004, 11, 1659; Nolan, E. M.; et al. Acc. Chem. Res. 2009, 42, 193; and Fahrni, C. J.; et al. J. Am. Chem. Soc. 1999, 121, 11448. Reverse-phase HPLC purifications were carried out on an Agilent Technologies 1200 Series HPLC system. Mass spectra were collected on an 1100-series Agilent LC/MSD ion trap. Aqueous solutions were prepared using Millipore water. Molecular biology grade piperazine-N,N'-bis(2-ethanesulfonic acid) (PIPES) and 99.999% KCl were purchased from Aldrich. In order to remove adventitious metal ions, buffered solutions were treated with Chelex resin (Bio-Rad) according to manufacturer specifications. A 50-mM zinc(II) stock solution was prepared using 99.999% $ZnCl_2$ (Aldrich). UV-vis spectra were recorded on a Varian Cary 50 Bio UV-visible spectrophotometer. Fluorescence spectra were recorded on a Quanta Master 4 L-format scanning spectrofluorimeter (Photon Technology International). The acquisition temperature was kept at 25±0.1° C. by circulating water bath. Sample solutions were placed in quartz cuvettes (Starna) with 1 cm path lengths. Stock solutions of Palm-ZP1 and ZQ-MPP were prepared in DMSO, partitioned in 50 μL aliquots and stored in the dark at −40° C.

Example 8

General Peptide Syntheses

Peptides were manually synthesized according to a modified literature protocol as outlined below. Kirin, S. I.; et al. J. Chem. Educ. 2007, 84, 108.

Palm-ZP1 (Palmitic acid-PPPDDK(ZPI)-$CONH_2$ ("PPP-DDK" disclosed as SEQ ID NO: 8))

Figure 20:
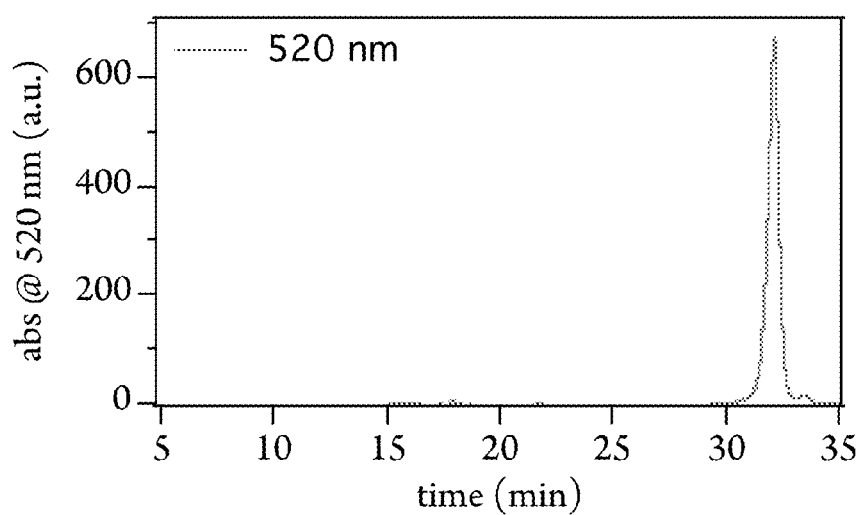
FIG. 20 depicts an analytical HPLC chromatogram of Palm-ZP1, monitoring at 520 nm. Palm-ZP1 was judged to be ≥95% pure based on the integrated absorbance signal.
Figure 21:
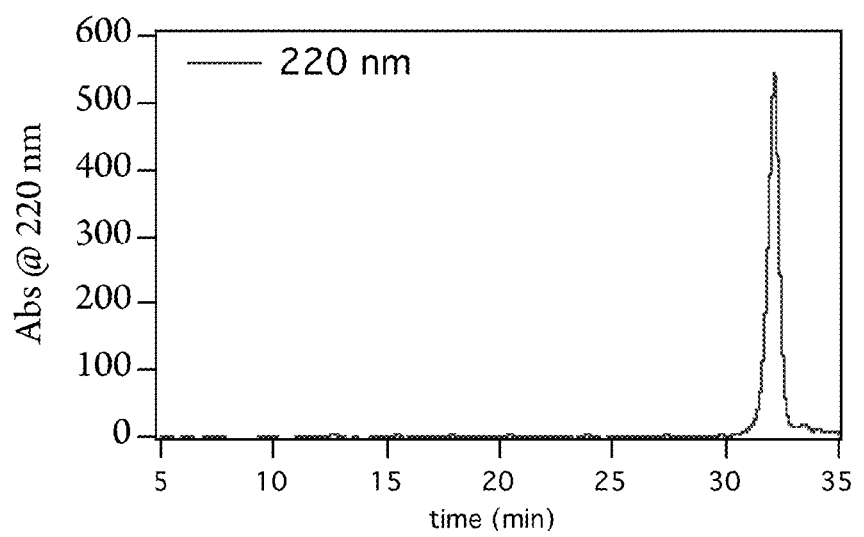
FIG. 21 depicts an analytical HPLC chromatogram of Palm-ZP1, monitoring at 220 nm. Palm-ZP1 was judged to be ≥95% pure based on the integrated absorbance signal.

Palm-ZP1 was synthesized on the 15-μmol scale using Rink amide AM resin. The resin was placed in a fritted 2.5-mL Torviq disposable syringe and swelled with 2 mL of anhydrous DMF for 1 hour prior to synthesis. N-terminal FMOC groups were removed by treating the resin with a solution of 20% 4-methylpiperidine in DMF (v/v) for a period of 10 min, followed by a 5×1.5 mL wash with DMF. For all coupling reactions, 60 μmol (4 equiv) of FMOC-protected amino acids, palmitic acid, or 6-$CO_2$H ZP1 were combined as solids with 60 μmol (23 mg) of HATU. Immediately prior to coupling, solids were dissolved in 1.5 mL of a freshly prepared 10% DIPEA/DMF (v/v) solution, placed in the reaction vessel and shaken for 25 min. After the allotted time, the resulting solution was expelled from the syringe and the resin was washed with 5×1.5 mL of DMF. Following addition of all amino acids and the N-terminal palmitic acid moiety, the 4-methyltrityl group was removed from the C-terminal Lys according to manufacturer specifications. Briefly, the resin was first exchanged into dichloromethane (DCM). A 3% TFA/DCM (v/v) solution was prepared, and the resin was mixed with the TFA/DCM mixture 2×1.5 mL for 10 min/ea. During equilibration, the TFA/DCM solution turned bright yellow, indicating that MTT was being liberated. After MTT deprotection, the resin was washed with 5×1.5 mL DCM followed by 5×1.5 mL DMF. The 6-$CO_2$H ZP1 was then coupled to the ε-amino group of the C-terminal Lys as described above. Following Palm-ZP1 synthesis, the resin was washed with 5×1.5 mL DCM and dried in vacuo for a period of ≥20 min prior to cleavage. Palm-ZP1 was cleaved from the resin by treating with a TFA/water/triisopropylsilane 95/2.5/2.5% (v/v) solution for 90 min. The resulting crude peptide was precipitated with cold ether and purified by HPLC on the semi-preparative scale using a C18 reverse-phase column (VYDAC, 9.5 mm×250 mm). A two-solvent system (A=0.1% (v/v) TFA in $H_2O$; B=0.1% TFA in acetonitrile (v/v)) was employed for purification according to the following protocol: isocratic flow, 20% B, 0-5 min; gradient #1, 10-50% B, 5-10 min; gradient #2, 50-95% B, 10-35 min. The flow-rate was kept constant at 3 mL $min^{-1}$ throughout the purification. Fractions from sequential runs containing Palm-ZP1 were pooled and lyophilized. The purity of the final product was assessed via analytical HPLC (Vydac, C18, 5 μm, 4.6 mm i.d.×250 mm). After a 5 min isocratic wash, a linear gradient of 10-75% B was run over 30 min (35 min total) at a flow rate of 1 mL $min^{-1}$. Palm-ZP1 (retention time=31.2 min) was judged to be ≥95% pure based on the integrated chromatogram (FIG. 20 and FIG. 21). Observed peaks (calculated) in ESI-MS (m/z, amu): 1755.8 (1755.9) [M+H]$^+$; 878.2 (878.5) [M+2H]$^{2+}$.

ZQ-MPP (zinquin-F$_x$rF$_x$rF$_x$r-CONH$_2$)

Figure 22:
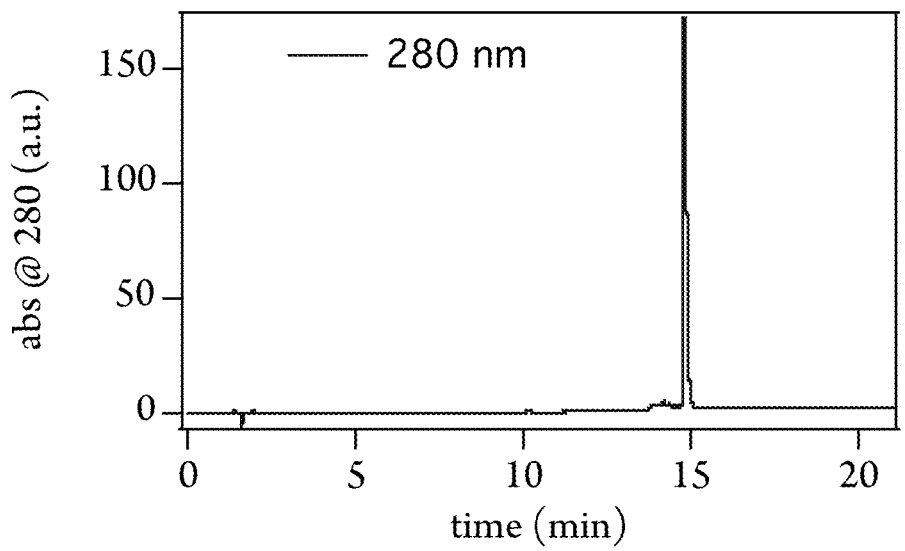
FIG. 22 depicts an analytical HPLC chromatogram of ZQ-MPP, monitoring at 280 nm. ZQ-MPP was judged to be ≥95% pure based on the integrated absorbance signal.
Figure 23:
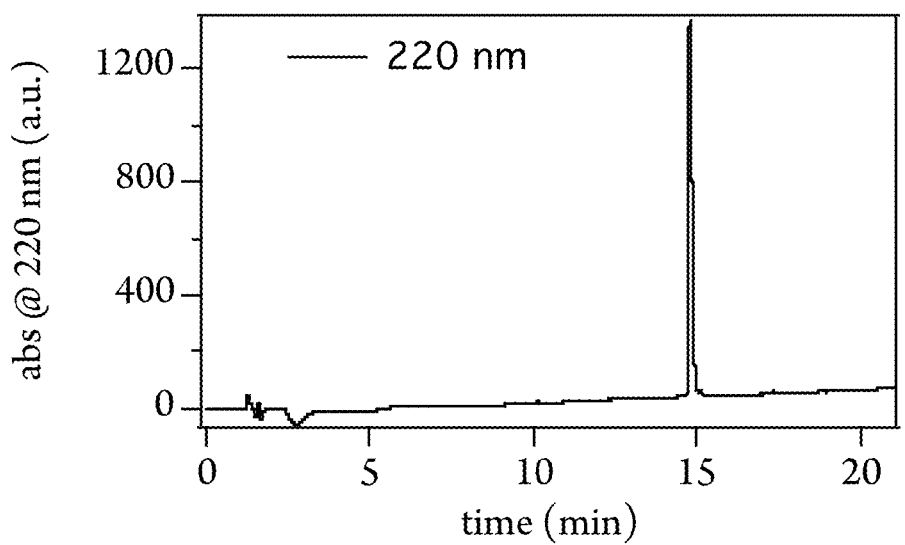
FIG. 23 depicts an analytical HPLC chromatogram of ZQ-MPP monitoring at 220 nm. ZQ-MPP was judged to be ≥95% pure based on the integrated absorbance signal.

ZQ-MPP was synthesized on the 15-μmol scale in a procedure similar to that used for Palm-ZP1. For conjugation of zinquin to the N-terminus of the peptide, 60 μmol (23 mg) of zinquin acid was mixed with 60 μmol (23 mg) of HATU in freshly prepared 10% DIPEA/DMF (v/v). The mixture was allowed to react with the resin for a period of 60 min, after which the resin was washed, cleaved, and purified. ZQ-MPP was purified via HPLC, using a two buffer system (vide supra), employing a linear gradient from 30-75% B over 20 min at a flow rate of 3 mL min$^{-1}$. Fractions containing ZQ-MPP from sequential runs were pooled and lyophilized. The purity of the final product was assessed via analytical HPLC (Vydac, C18, 5 μm, 4.6 mm i.d.×250 mm). A linear gradient of 30-60% B was run over 25 min at a flow rate of 1 mL min$^{-1}$. ZQ-MPP (retention time=14.7 min) was judged to be ≥95% pure based on the integrated chromatogram (FIG. 22 and FIG. 23). Observed peaks (calculated) in ESI-MS (m/z; amu): 1313.9 (1313.8) [M+H]$^+$; 657.7 (657.4) [M+2H]$^{2+}$, 438.8 (438.9) [M+3H]$^{3+}$.

Example 9

Zinc Binding

Photophyscial and Zinc-Binding Properties of Palm-ZP1

Spectroscopic measurements for Palm-ZP1 were carried out in a mixed solvent system consisting of 25 mM PIPES buffer (pH 7) with 50 mM KCl and 50% acetonitrile (v/v) (FIG. 24). Except where noted, all fluorescence data were obtained by exciting at 495 nm and observing from 500-650 nm, with 0.1 sec integration time and slit widths of 0.4 mm (1.6 nm). Emission spectra represent the average of three scans. The quantum yield of Palm-ZP1 was referenced to fluorescein in 0.1 M NaOH$_{(aq)}$, which has a known quantum yield of φ=0.95. Lakowicz, J. R. *Principles of fluorescence spectroscopy;* 2nd ed.; Kluwer Academic/Plenum: New York, 1999.

Apparent K$_{d-Zn}$ for Palm-ZP1:

Apparent zinc-binding affinities (K$_{d-Zn}$) were determined by a modified literature procedure. Walkup, G. K.; et al. *J. Am. Chem. Soc.* 2000, 122, 5644. For each zinc-binding titration, 1 mM EDTA and 2 mM CaCl$_2$ were added to the MeCN/PIPES buffered solution. Palm-ZP1 or ZP1 was added, and the system was allowed to reach equilibrium (30 min). Aliquots of ZnCl$_2$ were successively added, and the emission spectra recorded once the emission spectrum stabilized (~30 min). The amount of free zinc for a given concentration of total zinc was calculated using the maxchelator program (http://maxchelator.stanford.edu/webmaxc/webmaxcS.htm) based on initial values of 1 mM EDTA, 2 mM CaCl$_2$, an ionic strength of I=0.05 mol dm$^{-3}$, and a pH of 7.0. Due to the addition of acetonitrile to the buffered solution, we compared the apparent K$_{d-Zn}$ for Palm-ZP1 to ZP1 under identical conditions (FIG. 25 and FIG. 29).

Photophysical and Zinc-Binding Properties of ZQ-MPP

Characterization of ZQ-MPP (FIG. 26) was performed in 25 mM PIPES buffer (pH 7) with 50 mM KCl, and 50% (v/v) acetonitrile. Zinc affinities (K$_{d-Zn}$) were compared to TSQ under identical conditions (FIG. 27 and FIG. 30). Quantum yields for ZQ-MPP and TSQ were reference to quinine sulfate in 0.1 M H$_2$SO$_4$, which has a known quantum yield of (I)=0.58. Eastman, J. W. *Photochem. Photobio.* 1967, 6, 55.

Apparent K$_{d-Zn}$ for ZQ-MPP:

Apparent zinc-binding affinities (K$_{d-Zn}$) were determined using a modified literature procedure. Fahrni, C. J.; et al. *J. Am. Chem. Soc.* 1999, 121, 11448. For each zinc-binding titration, 2 mM EGTA was added to the MeCN/PIPES buffered solution. ZQ-MPP or TSQ was added and the system was allowed to reach equilibrium before beginning the titration (30 min). Aliquots of ZnCl$_2$ were successively added, and the emission spectra recorded once the emission spectrum stabilized (~30 min). The amount of free zinc for a given concentration of total zinc was calculated using the maxchelator program (http://maxchelator.stanford.edu/webmaxc/webmaxcS.htm) based on initial values of 2 mM EGTA at an ionic strength of I=0.05 mol dm$^{-3}$ and a pH of 7.0. Due to the addition of acetonitrile to the buffered solution, we compared the apparent K$_{d-Zn}$ for ZQ-MPP to TSQ under identical conditions (FIG. 27 and FIG. 30).

Example 10

Mammalian Cell Culture, Labeling, and Imaging Procedures

General

HeLa cells were cultured at 37° C. under a 5% CO$_2$ humidified atmosphere in Dulbecco's Modified Eagle Medium (High Glucose DMEM, Invitrogen) supplemented with 10% fetal bovine serum (FBS, HyClone), penicillin (100 μg/mL), and streptomycin (100 μg/mL). For live cell imaging, cells were seeded in 35-mm poly-D-Lys coated glass-bottom culture dishes (MatTek Corporation).

Palm-ZP1

Palm-ZP1 (10 μM) was incubated for 30 min at 37° C. and 5% CO$_2$ in DMEM. For multichannel imaging and co-localization studies, staining of the plasma membrane was accomplished by addition of Cell Mask Orange (Life Technologies, final concentration 2.5 μg/mL) for 15-20 min. Prior to imaging, cells were rinsed with warm dye- and serum-free DMEM (2×2 mL) and bathed in warm dye- and serum-free DMEM (2 mL). To assess the zinc responsiveness of Palm-ZP1, stock solutions of ZnCl$_2$ (10 mM) were diluted in warm dye- and serum-free DMEM to a final ZnCl$_2$ concentration of 50 μM. The zinc-enriched media was exchanged in the cell culture dish directly on the microscope stage. Similarly, a stock solution of ethylenediaminetetraacetic acid (EDTA, 100 mM) in water (pH 7) was diluted in warm dye- and serum-free DMEM to a concentration of 100 μM. Media containing EDTA was exchanged in the culture dishes on the microscope stage.

ZQ-MPP

ZQ-MPP (25 μM) was incubated for 1 h at 37° C. and 5% CO$_2$ in DMEM. For multi-channel imaging and colocalization studies, staining of the mitochondria was accomplished by addition of MitoTracker Red (Life Technologies, final concentration: 1 μM) for 30 min. Prior to imaging, cells were rinsed with warm dye- and serum-free DMEM (2×2 mL) and bathed in warm dye- and serum-free DMEM (2 mL). To assess the zinc responsiveness of ZQ-MPP, stock solutions of ZnCl$_2$ (10 mM) and sodium pyrithione (20 mM) in DMSO were combined in a 1:2 ratio (Zn:Py) and diluted in warm dye- and serum-free DMEM to a final Zn:Py complex concentration of 50 μM. The zinc-enriched media was exchanged in the cell culture dish directly on the microscope stage. Similarly, a stock solution of N,N,N',N'-tetrakis(2-pyridylmethyl)ethylenediamine (TPEN, 20 mM) in DMSO was diluted in warm dye- and serum-free DMEM to a 100 μM concentration. Media containing TPEN was exchanged in the culture dishes on the microscope stage.

Fluorescence Microscopy

The imaging experiments were performed using a Zeiss Axiovert 200M inverted epifluorescence microscope equipped with an EM-CCD digital camera (Hamamatsu) and a MS200 XY Piezo Z stage (Applied Scientific Instruments). The light source was an X-Cite 120 metal-halide lamp (EXFO) and the fluorescence images were obtained using an oil-immersion objective at 63× magnification. The microscope was operated using Volocity software (Perkin-Elmer).

Quantification of Zinc Turn-On

Images were processed using ImageJ. All settings (i.e., exposure time and sensitivity) were kept constant for each image series.

Pearson's Correlation Coefficients (r):

To calculate r, images were first deconvoluted using a calculated point-spread function (PSF) map based on emission wavelength, refractive index of the media (n=1.518), and the numerical aperture (1.4). Deconvoluted channels (i.e., sensor and organelle trackers) were merged and analyzed. For each image, a minimum of three regions-of-interest (ROI) were selected and the r-value calculated using an ImageJ plugin. French, A. P.; et al. *Nat. Protoc.* 2008, 3, 619. This process was repeated for 3-5 plates, which spanned multiple passage numbers (≤15) and days.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:
1. A compound, comprising a sensor moiety, a first linker, and a first amino acid, wherein the first amino acid is a natural amino acid or a non-natural α-amino acid; and the sensor moiety is selected from the group consisting of
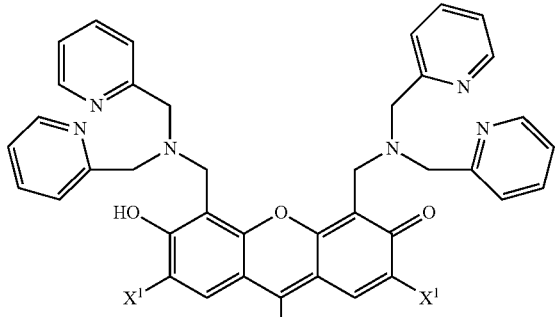
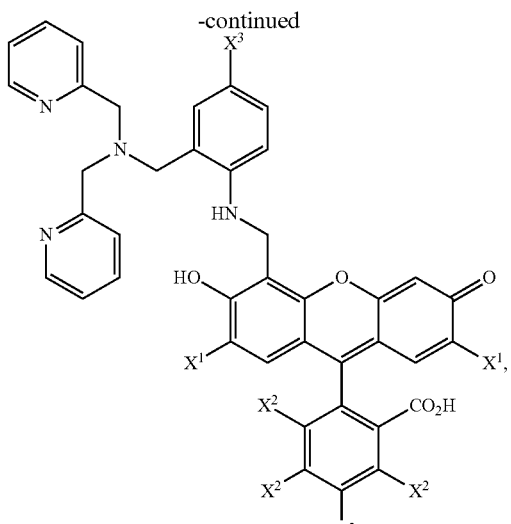
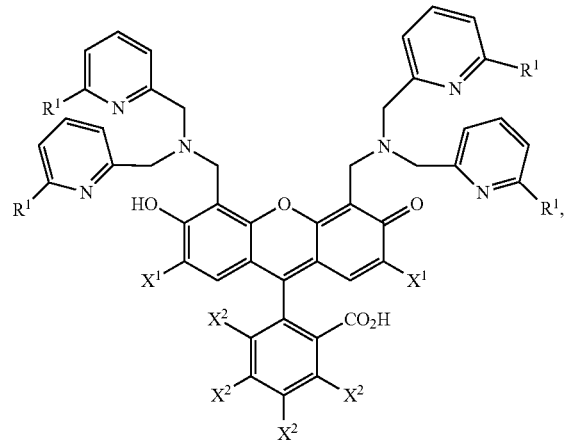
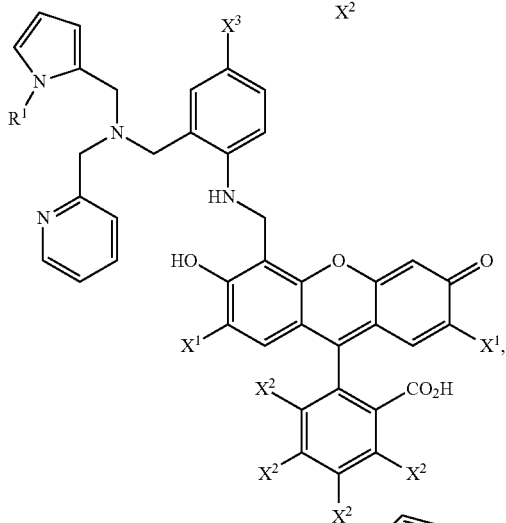
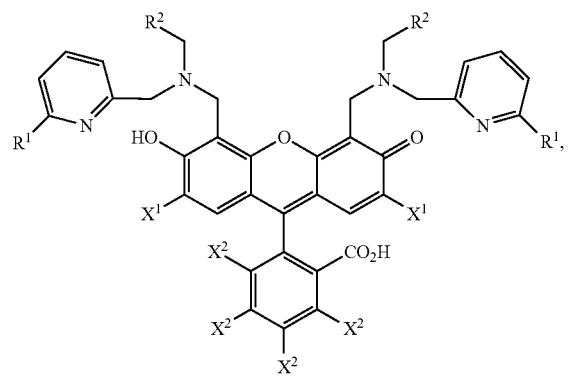
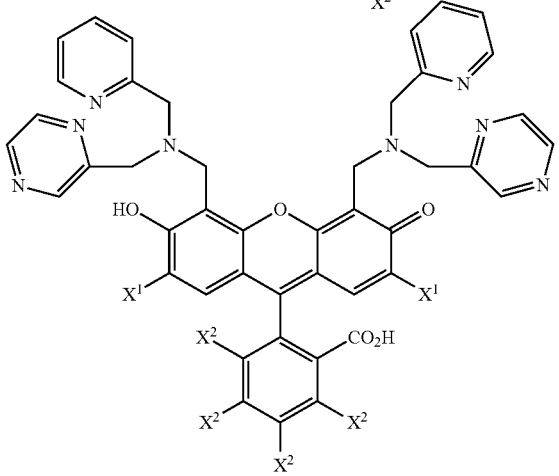

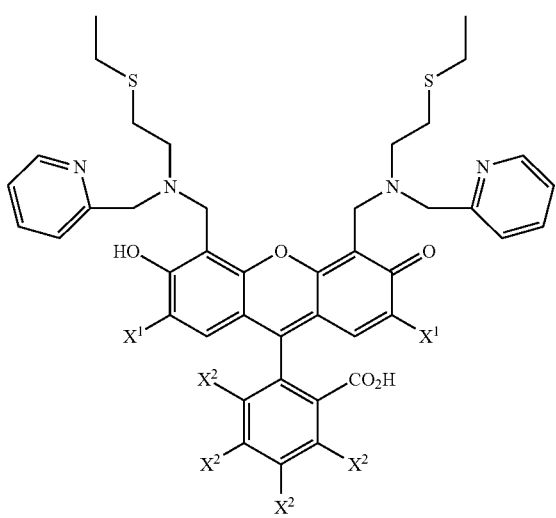

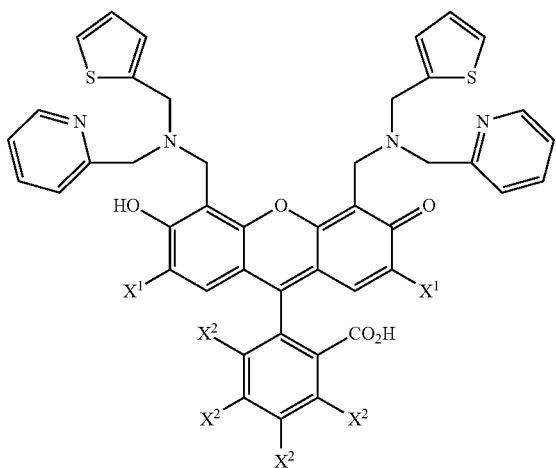

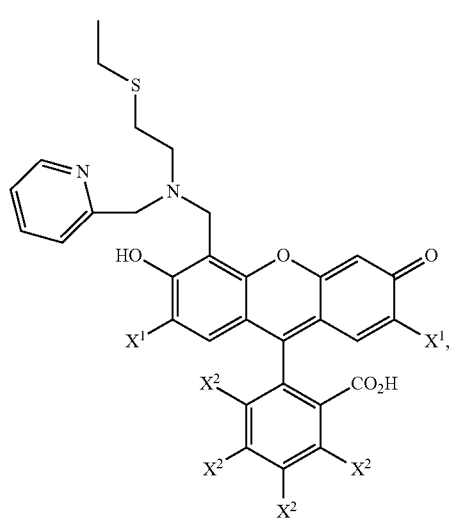

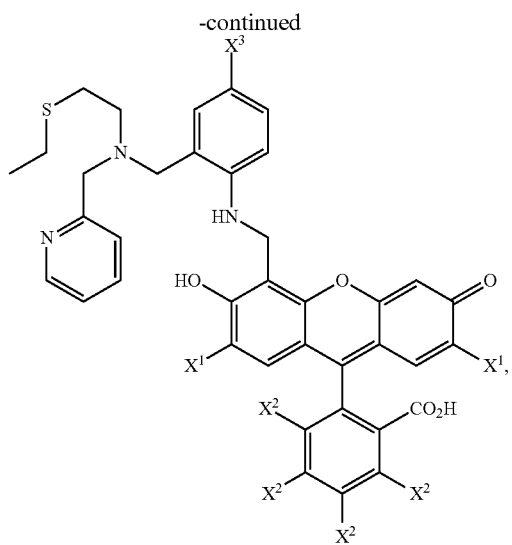

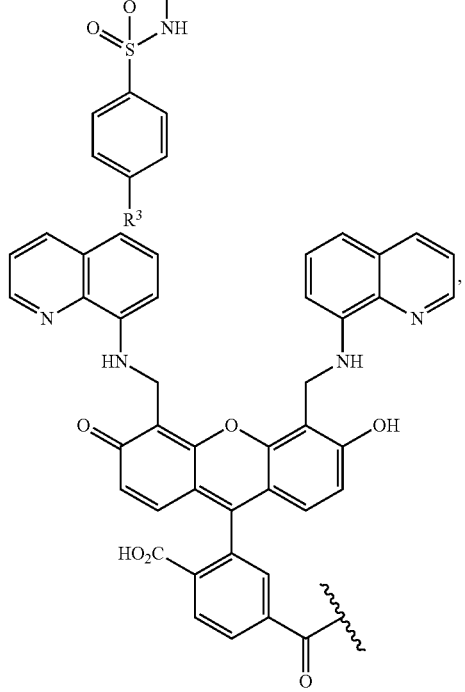

wherein, independently for each occurrence,
X$^1$ is —H, —F, or —Cl;
X$^2$ is —H, —F, —Cl, —CO$_2$R$^1$, —C(O)-(first linker), -(first linker), —NR$^1$-(first linker), or —S-(first linker), wherein at least one instance of X$^2$ is —C(O)-(first linker), -(first linker), —NR$^1$-(first linker), or —S-(first linker);
X$^3$ is —H, —F, —Cl, or —OR$^1$;
R$^1$ is —H or alkyl;
R$^2$ is —H or phenyl;
R$^3$ is H, alkyl, or —CO$_2$H;
R$^4$ is H or alkyl; and
X$^4$ is —C(O)-(first linker), -(first linker), —NR$^1$-(first linker), or —S-(first linker).

2. The compound of claim 1, wherein the first amino acid is lysine, 2,3-diaminopropionic acid, or glycine.

3. The compound of claim 1, wherein the first linker is an amide bond, a disulfide bond, a thioether bond, a thiourea, or a triazole.

4. The compound of claim 1, wherein the compound has the following formula:

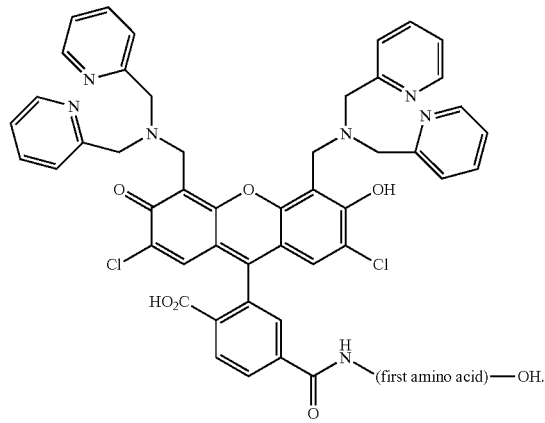

5. The compound of claim 1, wherein the compound has the following formula:

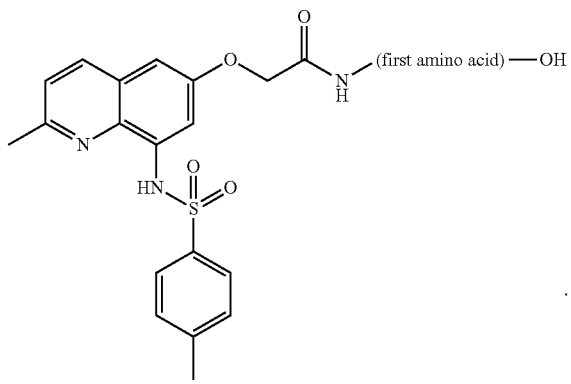

6. The amino acid compound of claim 1, wherein the compound is selected from the group consisting of

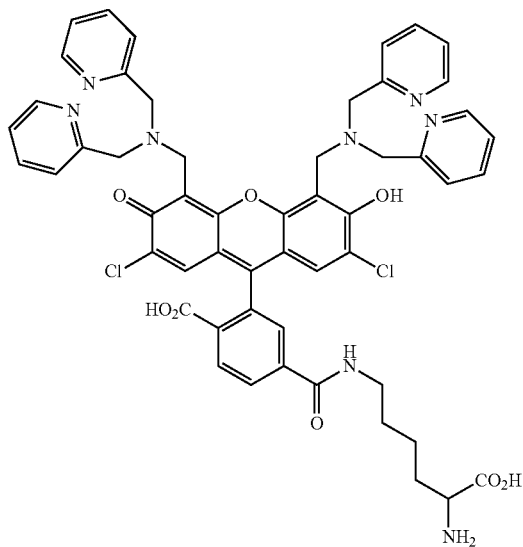

and

-continued

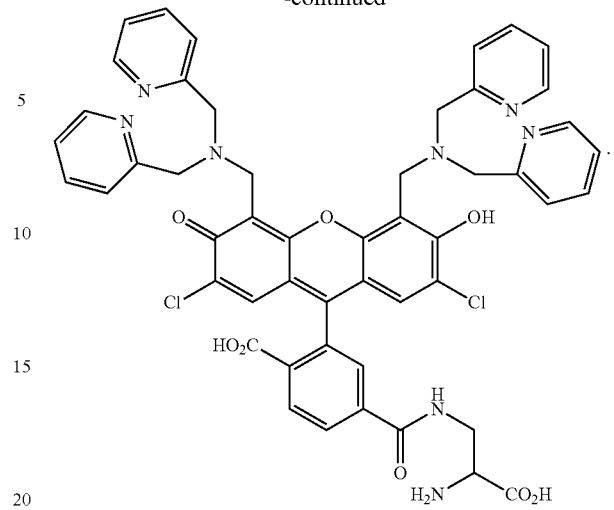

7. The compound of claim 1, further comprising a second amino acid, wherein the second amino acid is a natural amino acid or a non-natural amino acid.

8. The compound of claim 1, wherein the compound has the following formula (N-terminus→C-terminus):

$(Xaa)_p$-first amino acid-$(Xaa)_p$   (SEQ ID NO: 9)

wherein, independently for each occurrence,
the sensor moiety is covalently bonded to the side chain of the first amino acid via the first linker;
p is 0-10 inclusive;
at least one occurrence of p is not zero; and
Xaa is a natural amino acid or a non-natural amino acid.

9. The compound of claim 1, wherein the compound comprises the following formula:

RGD-first amino acid-first linker-sensor moiety   (SEQ ID NO: 10)

wherein
the sensor moiety is covalently bonded to the side chain of the first amino acid via the first linker;
the first amino acid is 2,3-diaminopropionic acid;
the first linker is an amide bond; and
the sensor moiety is

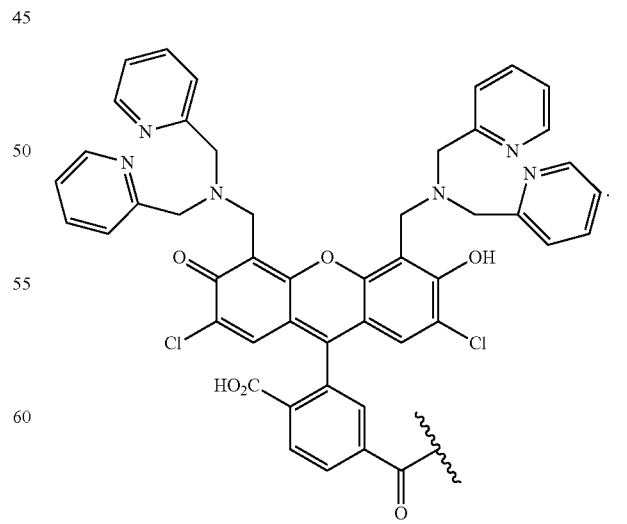

10. The compound of claim 1, wherein the compound has the following formula (N-terminus→C-terminus):

H₃C—(CH₂)₁₄—C(O)-(Xaa)$_p$-first amino acid-NH₂    (SEQ ID NO: 11)

wherein
  p is 0-10 inclusive;
  the sensor moiety is covalently bonded to the side chain of the first amino acid via the first linker;
  the first amino acid is lysine;
  the first linker is an amide bond; and
  the sensor moiety is

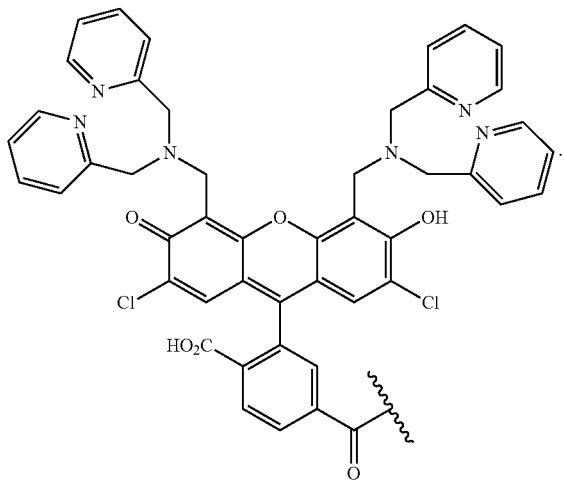 [SMILES: *C(=O)c1ccc(C(=O)O)c(-c2c3cc(Cl)c(=O)c(CN(Cc4ccccn4)Cc4ccccn4)c-3oc3c(CN(Cc4ccccn4)Cc4ccccn4)c(O)c(Cl)cc23)c1]

11. The compound of claim 1, wherein the compound has the following formula (N-terminus→C-terminus):

sensor moiety-first linker-first amino acid-(Xaa)$_p$-NH₂    (SEQ ID NO: 12)

wherein
  p is 0-10 inclusive;
  the sensor moiety is covalently bonded to the N-terminus of the first amino acid via the first linker;
  the first amino acid is cyclohexylalanine;
  the first linker is an amide bond; and
  the sensor moiety is

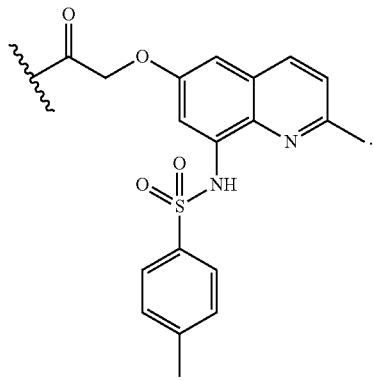 [SMILES: *C(=O)COc1cc(NS(=O)(=O)c2ccc(C)cc2)c2nc(C)ccc2c1]

12. The compound of claim 7, wherein the compound further comprises a detectable moiety.

13. The compound of claim 12, wherein the detectable moiety is a phosphorescent moiety or a fluorescent moiety.

14. The compound of claim 12, wherein the detectable moiety is coumarin or a coumarin derivative.

15. The compound of claim 12, wherein the detectable moiety is rhodamine or a rhodamine derivative.

16. The compound of claim 12, wherein the compound comprises the following formula:

sensor moiety-first linker-first amino acid-(Xaa)$_p$-second amino acid-(Xaa)$_p$    (SEQ ID NO: 13)

wherein, independently for each occurrence,
  the sensor moiety is covalently bonded to the N-terminus of the first amino acid via the first linker, or the sensor moiety is covalently bonded to the side chain of the first amino acid via the first linker;
  the detectable moiety is covalently bonded to the side chain of the second amino acid via a second linker;
  p is 0-10 inclusive; and
  Xaa is a natural amino acid or a non-natural amino acid.

17. The compound of claim 12, wherein the compound comprises the following formula:

detectable moiety-second linker-second amino acid-(Xaa)$_p$-first amino acid-(Xaa)$_p$    (SEQ ID NO: 14)

wherein, independently for each occurrence,
  the detectable moiety is covalently bonded to the N-terminus of the second amino acid via the second linker, or the detectable moiety is covalently bonded to the side chain of the second amino acid via the second linker;
  the sensor moiety is covalently bonded to the side chain of the first amino acid via the first linker;
  p is 0-10 inclusive; and
  Xaa is a natural amino acid or a non-natural amino acid.

18. The compound of claim 12, wherein the compound comprises the following formula:

(Xaa)$_p$-first amino acid-(Xaa)$_p$-second amino acid-(Xaa)$_p$    (SEQ ID NO: 15)

Or (Xaa)$_p$-second amino acid-(Xaa)$_p$-first amino acid-(Xaa)$_p$    (SEQ ID NO: 16)

wherein, independently for each occurrence,
  the sensor moiety is covalently bonded to the side chain of the first amino acid via the first linker;
  the detectable moiety is covalently bonded to the side chain of the second amino acid via a second linker;
  p is 0-10 inclusive; and
  Xaa is a natural amino acid or a non-natural amino acid.

19. The compound of claim 12, wherein the compound comprises the following formula:

sensor moiety-first linker-first amino acid-PPP -second amino acid-Xaa    (SEQ ID NO: 17)

wherein
the sensor moiety is

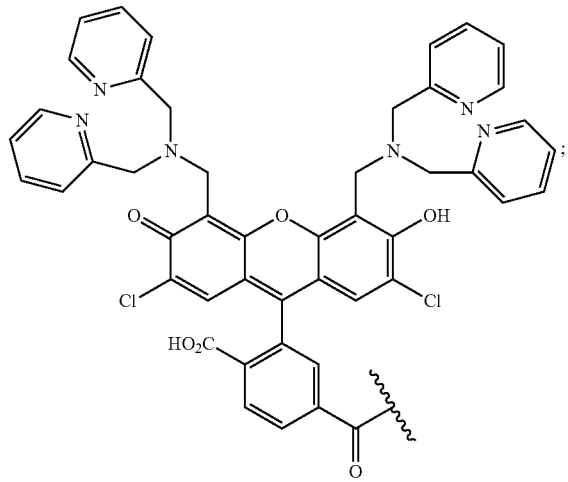 [SMILES: *C(=O)c1ccc(C(=O)O)c(-c2c3cc(Cl)c(=O)c(CN(Cc4ccccn4)Cc4ccccn4)c-3oc3c(CN(Cc4ccccn4)Cc4ccccn4)c(O)c(Cl)cc23)c1]

the first linker is an amide bond;
the first amino acid is glycine;
the second amino acid is lysine;
the detectable moiety is covalently bonded to the side chain of the second amino acid via a second linker;
the detectable moiety is a coumarin derivative;
the second linker is an amide bond; and
Xaa is a natural amino acid or a non-natural amino acid.

20. The compound of claim 12, wherein the compound comprises the following formula:

sensor moiety-first linker-first amino acid-PPP -second amino acid-DDD  (SEQ ID NO: 18)

wherein
the sensor moiety is

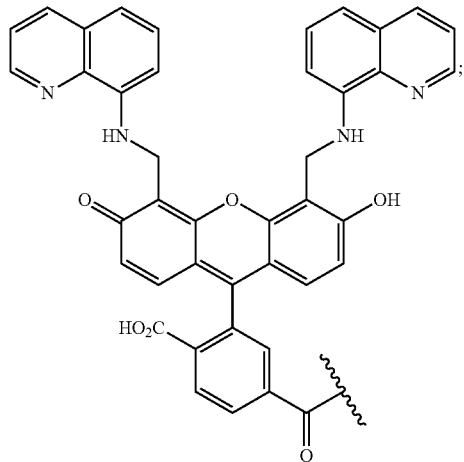 [SMILES: *C(=O)c1ccc(C(=O)O)c(-c2c3ccc(=O)c(CNc4cccc5cccnc45)c-3oc3c(CNc4cccc5cccnc45)c(O)ccc23)c1]

the first linker is an amide bond;
the first amino acid is 2,3-diaminopropionic acid;
the second amino acid is lysine;
the detectable moiety is covalently bonded to the side chain of the second amino acid via a second linker;
the detectable moiety is a coumarin derivative; and
the second linker is an amide bond.

21. A method of quantifying an amount of a substance in a cell, comprising the steps of:
contacting the cell with a detectable amount of a compound of claim 1; and
detecting a signal, wherein the signal emitted by the compound in the presence of the substance is different than the signal emitted by the compound in the absence of the substance.

22. The method of claim 21, wherein the method is a method of quantifying an amount of a substance in a specific locale of a cell, comprising the steps of:
contacting the cell with a detectable amount of a compound of claim 1; and
detecting a signal from the specific locale of the cell, wherein the signal emitted by the compound in the presence of the substance is different than the signal emitted by the compound in the absence of the substance.

23. The method of claim 22, wherein the specific locale in the cell is an intracellular probe, an extracellular probe, a trans-Golgi network, a mitochondrion, or an endoplasmic reticulum.

24. The method of claim 21, wherein the substance is selected from the group consisting of $Zn^{2+}$, nitric oxide, $Ca^+$, $Cu^+$, $Cu^{2+}$, $H^+$, hydrogen peroxide, hydrogen sulfide, and reactive oxygen species (ROS).

25. A method of quantifying an amount or determining a location of a substance in a subject, comprising the steps of:
administering to the subject a detectable amount of a compound of claim 1; and
detecting a signal, wherein the signal emitted by the compound in the presence of the substance is different than the signal emitted by the compound in the absence of the substance.

26. The method of claim 25, wherein the location of the substance is the synaptic cleft, the intracellular space of the hippocampus, mossy fiber buttons of the hippocampus, the pancreas, or the prostate.

27. The method of claim 25, wherein the subject is a mammal.

28. The method of claim 25, wherein the substance is selected from the group consisting of $Zn^{2+}$, nitric oxide, $Ca^{2+}$, $Cu^+$, $Cu^{2+}$, $H^+$, hydrogen peroxide, hydrogen sulfide, and reactive oxygen species (ROS).

* * * * *

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Leu Ala Lys Ala Leu Ala Lys Ala Leu Ala
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Lys Lys Arg Arg Gln Arg Arg Arg Pro Gln
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Ser Asp Tyr Gln Arg Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Asp Glu Leu
1

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gly Glu Gly Ala Ala Val Leu Leu Pro Val Leu Leu Ala Ala Pro
1               5                   10                  15

Gly

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Pro Pro Asp Asp
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Palmitic acid
<220> FEATURE:
<221> NAME/KEY: MOD_RES
<222> LOCATION: (6)..(6)
<223> OTHER INFORMATION: Lys(ZP1)
<220> FEATURE:
<223> OTHER INFORMATION: C-term CONH2

<400> SEQUENCE: 8

Pro Pro Pro Asp Asp Lys
1               5

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(10)
<223> OTHER INFORMATION: Any natural or non-natural amino acid and this
      region may encompass 0 to 10 residues in length
<220> FEATURE:
<221> NAME/KEY: MOD_RES
<222> LOCATION: (11)..(11)
<223> OTHER INFORMATION: Any amino acid with a sensor moiety covalently
      bonded to the side chain via the first linker
<220> FEATURE:
<221> NAME/KEY: MOD_RES
<222> LOCATION: (12)..(21)
<223> OTHER INFORMATION: Any natural or non-natural amino acid and this
      region may encompass 0 to 10 residues in length
<220> FEATURE:
<223> OTHER INFORMATION: see specification as filed for detailed
      description of substitutions and preferred embodiments

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2,3-diaminopropionic acid with a sensor moiety
      covalently bonded to the side chain via the first linker
<220> FEATURE:
<223> OTHER INFORMATION: see specification as filed for detailed
      description of substitutions and preferred embodiments

<400> SEQUENCE: 10

Arg Gly Asp Xaa
1

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H3C-(CH2)14-C(O)
<220> FEATURE:
<221> NAME/KEY: MOD_RES
<222> LOCATION: (1)..(10)
<223> OTHER INFORMATION: Any amino acid and this region may encompass
      0 to 10 residues in length
<220> FEATURE:
<221> NAME/KEY: MOD_RES
<222> LOCATION: (11)..(11)
<223> OTHER INFORMATION: Lys with a sensor moiety covalently bonded to
      the side chain via the first linker
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 11

Xaa Xaa Xaa Xaa Xaa Xaa Xaa Xaa Xaa Xaa Lys
1               5                   10
```

```
<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term cyclohexylamine with a sensor moiety
      covalently bonded to the N-term via the first linker
<220> FEATURE:
<221> NAME/KEY: MOD_RES
<222> LOCATION: (1)..(10)
<223> OTHER INFORMATION: Any natural or non-natural amino acid and this
      region may encompass 0 to 10 residues in length
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 12

Xaa Xaa Xaa Xaa Xaa Xaa Xaa Xaa Xaa Xaa
1               5                   10

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid with a sensor moiety covalently
      bonded to the N-term via the first linker or covalently bonded
      to the side chain via the first linker
<220> FEATURE:
<221> NAME/KEY: MOD_RES
<222> LOCATION: (2)..(11)
<223> OTHER INFORMATION: Any natural or non-natural amino acid and this
      region may encompass 0 to 10 residues in length
<220> FEATURE:
<221> NAME/KEY: MOD_RES
<222> LOCATION: (12)..(12)
<223> OTHER INFORMATION: Any amino acid with a detectable moiety
      covalently bonded to the side chain via the second linker
<220> FEATURE:
<221> NAME/KEY: MOD_RES
<222> LOCATION: (13)..(22)
<223> OTHER INFORMATION: Any natural or non-natural amino acid and this
      region may encompass 0 to 10 residues in length
<220> FEATURE:
<223> OTHER INFORMATION: see specification as filed for detailed
      description of substitutions and preferred embodiments

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid with a detachable moiety
```

```
       covalently bonded to the N-term via the second linker or
       covalently bonded to the side chain via the second linker
<220> FEATURE:
<221> NAME/KEY: MOD_RES
<222> LOCATION: (2)..(11)
<223> OTHER INFORMATION: Any natural or non-natural amino acid and this
       region may encompass 0 to 10 residues in length
<220> FEATURE:
<221> NAME/KEY: MOD_RES
<222> LOCATION: (12)..(12)
<223> OTHER INFORMATION: Any amino acid with a sensor moiety covalently
       bonded to the side chain via the first linker
<220> FEATURE:
<221> NAME/KEY: MOD_RES
<222> LOCATION: (13)..(22)
<223> OTHER INFORMATION: Any natural or non-natural amino acid and this
       region may encompass 0 to 10 residues in length
<220> FEATURE:
<223> OTHER INFORMATION: see specification as filed for detailed
       description of substitutions and preferred embodiments

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (1)..(10)
<223> OTHER INFORMATION: Any natural or non-natural amino acid and this
       region may encompass 0 to 10 residues in length
<220> FEATURE:
<221> NAME/KEY: MOD_RES
<222> LOCATION: (11)..(11)
<223> OTHER INFORMATION: Any amino acid with a sensor moiety covalently
       bonded to the side chain via the first linker
<220> FEATURE:
<221> NAME/KEY: MOD_RES
<222> LOCATION: (12)..(21)
<223> OTHER INFORMATION: Any natural or non-natural amino acid and this
       region may encompass 0 to 10 residues in length
<220> FEATURE:
<221> NAME/KEY: MOD_RES
<222> LOCATION: (22)..(22)
<223> OTHER INFORMATION: Any amino acid with a detectable moiety
       covalently bonded to the side chain via the second linker
<220> FEATURE:
<221> NAME/KEY: MOD_RES
<222> LOCATION: (23)..(32)
<223> OTHER INFORMATION: Any natural or non-natural amino acid and this
       region may encompass 0 to 10 residues in length
<220> FEATURE:
<223> OTHER INFORMATION: see specification as filed for detailed
       description of substitutions and preferred embodiments

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 16
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any natural or non-natural amino acid and this
      region may encompass 0 to 10 residues in length
<220> FEATURE:
<221> NAME/KEY: MOD_RES
<222> LOCATION: (11)..(11)
<223> OTHER INFORMATION: Any amino acid with a detectable moiety
      covalently bonded to the side chain via the second linker
<220> FEATURE:
<221> NAME/KEY: MOD_RES
<222> LOCATION: (12)..(21)
<223> OTHER INFORMATION: Any natural or non-natural amino acid and this
      region may encompass 0 to 10 residues in length
<220> FEATURE:
<221> NAME/KEY: MOD_RES
<222> LOCATION: (22)..(22)
<223> OTHER INFORMATION: Any amino acid with a sensor moiety covalently
      bonded to the side chain via the first linker
<220> FEATURE:
<221> NAME/KEY: MOD_RES
<222> LOCATION: (23)..(32)
<223> OTHER INFORMATION: Any natural or non-natural amino acid and this
      region may encompass 0 to 10 residues in length
<220> FEATURE:
<223> OTHER INFORMATION: see specification as filed for detailed
      description of substitutions and preferred embodiments

<400> SEQUENCE: 16

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly with a sensor moiety covalently bonded to
      the side chain via the first linker
<220> FEATURE:
<221> NAME/KEY: MOD_RES
<222> LOCATION: (5)..(5)
<223> OTHER INFORMATION: Lys with a detectable moiety covalently bonded
      to the side chain via the second linker
<220> FEATURE:
<221> NAME/KEY: MOD_RES
<222> LOCATION: (6)..(6)
<223> OTHER INFORMATION: Any natural or non-natural amino acid
<220> FEATURE:
<223> OTHER INFORMATION: see specification as filed for detailed
      description of substitutions and preferred embodiments

<400> SEQUENCE: 17

Gly Pro Pro Pro Lys Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 2,3-diaminopropionic acid with a sensor moiety
      covalently bonded to the side chain via the first linker
<220> FEATURE:
<221> NAME/KEY: MOD_RES
<222> LOCATION: (5)..(5)
<223> OTHER INFORMATION: Lys with a detectable moiety covalently bonded
      to the side chain via the second linker
<220> FEATURE:
<223> OTHER INFORMATION: see specification as filed for detailed
      description of substitutions and preferred embodiments

<400> SEQUENCE: 18

Xaa Pro Pro Pro Lys Asp Asp Asp
1               5

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid with a sensor moiety covalently
      bonded to the N-term via the first linker or covalently bonded
      to the side chain via the first linker
<220> FEATURE:
<221> NAME/KEY: MOD_RES
<222> LOCATION: (2)..(11)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (12)..(12)
<223> OTHER INFORMATION: Any amino acid with a detectable moiety
      covalently bonded to the side chain via the second linker
<220> FEATURE:
<221> NAME/KEY: MOD_RES
<222> LOCATION: (13)..(22)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<223> OTHER INFORMATION: see specification as filed for detailed
      description of substitutions and preferred embodiments

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid with a detachable moiety
      covalently bonded to the N-term via the second linker or
      covalently bonded to the side chain via the second linker
<220> FEATURE:
```

```
<221> NAME/KEY: MOD_RES
<222> LOCATION: (2)..(11)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (12)..(12)
<223> OTHER INFORMATION: Any amino acid with a sensor moiety covalently
      bonded to the side chain via the first linker
<220> FEATURE:
<221> NAME/KEY: MOD_RES
<222> LOCATION: (13)..(22)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<223> OTHER INFORMATION: see specification as filed for detailed
      description of substitutions and preferred embodiments

<400> SEQUENCE: 20

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (11)..(11)
<223> OTHER INFORMATION: Any amino acid with a sensor moiety covalently
      bonded to the side chain via the first linker
<220> FEATURE:
<221> NAME/KEY: MOD_RES
<222> LOCATION: (12)..(21)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (22)..(22)
<223> OTHER INFORMATION: Any amino acid with a detectable moiety
      covalently bonded to the side chain via the second linker
<220> FEATURE:
<221> NAME/KEY: MOD_RES
<222> LOCATION: (23)..(32)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<223> OTHER INFORMATION: see specification as filed for detailed
      description of substitutions and preferred embodiments

<400> SEQUENCE: 21

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
```

```
                   20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (11)..(11)
<223> OTHER INFORMATION: Any amino acid with a detectable moiety
      covalently bonded to the side chain via the second linker
<220> FEATURE:
<221> NAME/KEY: MOD_RES
<222> LOCATION: (12)..(21)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<221> NAME/KEY: MOD_RES
<222> LOCATION: (22)..(22)
<223> OTHER INFORMATION: Any amino acid with a sensor moiety covalently
      bonded to the side chain via the first linker
<220> FEATURE:
<221> NAME/KEY: MOD_RES
<222> LOCATION: (23)..(32)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid and this
      region may encompass 0 to 10 residues in length
<220> FEATURE:
<223> OTHER INFORMATION: see specification as filed for detailed
      description of substitutions and preferred embodiments

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly with a sensor moiety covalently bonded to
      the side chain via the first linker
<220> FEATURE:
<221> NAME/KEY: MOD_RES
<222> LOCATION: (5)..(5)
<223> OTHER INFORMATION: Lys with a detectable moiety covalently bonded
      to the side chain via the second linker
<220> FEATURE:
<221> NAME/KEY: MOD_RES
<222> LOCATION: (6)..(6)
<223> OTHER INFORMATION: Arg, His, Lys, Asp, Glu, Ser, Thr, Asn, Gln,
      Cys, Selenocys, Gly, Pro, Ala, Val, Ile, Leu, Met, Phe,
      Tyr, Trp or 2,3-diaminopropionic acid
<220> FEATURE:
<223> OTHER INFORMATION: see specification as filed for detailed
``` description of substitutions and preferred embodiments
<400> SEQUENCE: 23
Gly Pro Pro Pro Lys Xaa
1               5